United States Patent
Shinagawa et al.

(10) Patent No.: US 7,285,572 B2
(45) Date of Patent: *Oct. 23, 2007

(54) CASR ANTAGONIST

(75) Inventors: Yuko Shinagawa, Osaka (JP); Teruhiko Inoue, Osaka (JP); Toshihiro Kiguchi, Osaka (JP); Taku Ikenogami, Osaka (JP); Naoki Ogawa, Osaka (JP); Takashi Nakagawa, Osaka (JP); Masanori Shindo, Osaka (JP); Yuki Soejima, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/286,378

(22) Filed: Nov. 25, 2005

(65) Prior Publication Data

US 2006/0135572 A1    Jun. 22, 2006

Related U.S. Application Data

(63) Continuation of application No. PCT/JP2004/007758, filed on May 28, 2004.

(30) Foreign Application Priority Data

May 28, 2003  (JP) ............................. 2003-151610

(51) Int. Cl.
 A61K 31/19    (2006.01)
 A61K 31/195   (2006.01)
 A61K 31/185   (2006.01)
 C07C 61/00    (2006.01)
 C07C 211/00   (2006.01)

(52) U.S. Cl. .................. 514/529; 514/557; 514/567; 514/576; 562/400; 564/305

(58) Field of Classification Search ............... 514/529, 514/557, 567, 576; 562/400; 564/305
See application file for complete search history.

(56) References Cited

U.S. PATENT DOCUMENTS

| | | | |
|---|---|---|---|
| 6,022,894 A | 2/2000 | Del Mar et al. | 514/524 |
| 6,291,459 B1 | 9/2001 | Bhatnagar | 514/237.8 |
| 6,294,531 B1 | 9/2001 | Barmore et al. | 514/275 |
| 6,335,338 B1 | 1/2002 | Bhatnagar | 514/259.2 |
| 6,395,919 B1 | 5/2002 | Bhatnagar | 558/414 |
| 6,417,215 B1 | 7/2002 | Lago | 514/381 |
| 6,916,956 B2 * | 7/2005 | Shinagawa et al. | 564/88 |

FOREIGN PATENT DOCUMENTS

| | | |
|---|---|---|
| EP | 901459 A | 3/1999 |
| EP | 973730 A | 1/2000 |
| EP | 1070048 A | 1/2001 |
| JP | 2001-501584 | 2/2001 |
| JP | 2001-523223 | 11/2001 |
| JP | 2002-510671 | 4/2002 |
| JP | 2002-522499 | 7/2002 |
| JP | 2002-522532 | 7/2002 |
| JP | 2002-536330 | 10/2002 |
| WO | 97/37967 | 10/1997 |
| WO | 98/45255 | 10/1998 |
| WO | 99/51241 | 10/1999 |
| WO | 99/51569 | 10/1999 |
| WO | 00/09132 | 2/2000 |
| WO | 00/09491 | 2/2000 |
| WO | 00/45816 | 8/2000 |
| WO | 02/07673 | 1/2002 |
| WO | 02/14259 | 2/2002 |
| WO | 02/34204 | 5/2002 |
| WO | 02/38106 | 5/2002 |

OTHER PUBLICATIONS

Co-pending U.S. Appl. No. 10/830,480.*

C.S. Tam, et al., Parathyroid Hormone Stimulates the Bone Apposition Rate Independently of its Resorptive Action: Differential Effects of Intermittent and Continuous Administration, *Endocrinology*, 110, 506-512 (1982).

T. Uzawa, et al., Comparison of the Effects of Intermittent and Continuous Administration of Human Parathyroid Hormone (1-34) on Rat Bone, *Bone*, 16, 477-484 (1995).

A. Scott, et al., Time Dependent Effects of Parathyroid Hormone and Prostaglandin E2 on DNA Synthesis by Periosteal Cells from Embryonic Chick *Calvaria*, *Calcified Tissue International*, 55, 208-215 (1994).

(Continued)

*Primary Examiner*—Kamal A. Saeed
*Assistant Examiner*—Susannah Chung
(74) *Attorney, Agent, or Firm*—Fitzpatrick, Cella, Harper & Scinto

(57) ABSTRACT

The present invention provides a compound having a calcium-sensitive receptor antagonistic action, a pharmaceutical composition containing the compound, particularly a calcium receptor antagonist and a therapeutic drug for osteoporosis. A compound represented by the following formula (1), a pharmaceutically acceptable salt thereof or an optically active form thereof:

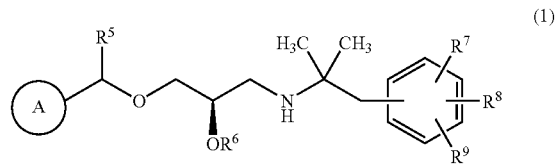

wherein each symbol is as defined in the description.

10 Claims, No Drawings

OTHER PUBLICATIONS

T.J. Wronski, et al., Parathyroid Hormone is More Effective Than Estrogen or Bisphosphonates for Restoration of Lost Bone Mass in Ovariectomized Rats, *Endocrinology*, 132, 823-831 (1993).

T. J. Wronski, et al., Anabolic effects of parathyroid hormone on cortical bone in ovari-ectomized rats, *Bone*, 15, 51-58 (1994).

L. Mosekilde, et al., The Anabolic Effects of Human Parathyroid Hormone (hPTH) on Rat Vertebral Body Mass Are also Reflected in the Quality of Bone, Assessed by Biomechanical Testing: A Comparison Study between hPTH-1(1-34) and hPTH(1-84), *Endocrinology*, 129, 421-428 (1991).

E.M. Brown, et al., Cloning and characterization of an extracellular Ca2+-sensing receptor from bovine parathyroid, *Nature*, 366, 575-580 (1993).

T.M. Gowen, et al., Antagonizing the parathyroid calcium receptor stimulates parathyroid hormone secretion and bone formation in osteopenic rats, *The Journal of Clinical Investigation*, vol. 105, pp. 1595-1604 (2000).

C. Ejersted, et al., Human parathyroid hormone (1-34) and (1-84) increase the mechanical strength and thickness of cortical bone in rats, *Journal of Bone and Mineral Research*, 8, 1097-1101 (1993).

* cited by examiner

CASR ANTAGONIST

This application is a continuation of International Application No. PCT/JP2004/007758, filed May 28, 2004, which is incorporated by reference in its entirety.

TECHNICAL FIELD

The present invention relates to a compound having a calcium-sensing receptor (CaSR, hereinafter to be simply referred to as a calcium receptor) antagonistic action, a pharmaceutical composition containing the compound, particularly a calcium receptor antagonist and a therapeutic agent of osteoporosis.

BACKGROUND ART

Calcium receptors sense extracellular $Ca^{2+}$ concentration and increase intracellular $Ca^{2+}$, thereby acting to suppress the production of parathyroid hormone (PTH) involved in the control of $Ca^{2+}$ metabolism and bone metabolism.

The serum calcium concentration of healthy mammal is strictly maintained at about 9-10 mg/100 ml (ca. 2.5 mM), which is referred to as calcium homeostasis of living organisms. When this value falls to not more than 50%, tetania occurs, and conversely, when it increases by 50%, consciousness is clouded, both cases threatening the lives. For maintaining calcium homeostasis, duodenum acts as a $Ca^{2+}$ uptake organ, bone acts as a $Ca^{2+}$ storage organ, and kidney acts as a $Ca^{2+}$ excretory organ. These $Ca^{2+}$ kinetics are controlled by various hormones generally referred to as "calcium controlling hormone". Representative hormone includes active vitamin D [$1\alpha$, $25(OH)_2D_3$], PTH, calcitonin, Parathyroid Hormone-Related Protein (PTH-related Protein (PTHrP)) and the like.

Bone plays an important role not only as a supporting framework and motor organ of the body, but also as a storage organ of $Ca^{2+}$, which is its constituent component. To fulfill such functions, bone tissues repeat formation thereof (osteogenesis) and absorption thereof (bone resorption) throughout the entire life. For osteogenesis, osteoblast derived from mesenchymal cell plays a major role, and for bone resorption, osteoclast derived from hematopoietic cell plays a major role. The mechanism of osteogenesis includes osteoid formation by bone organic matrix (bone matrix proteins such as type I collagen and the like) produced by osteoblast present on the osteogenesis surface, and subsequent calcification. On the other hand, the mechanism of bone resorption includes adhesion of osteoclast to the bone surface, intracellular absorption of $Ca^{2+}$ via protease acid secretion and ion transport, and excretion of absorbed $Ca^{2+}$ to the bone marrow side, thereby releasing $Ca^{2+}$ into blood. The deficient part of the bone absorbed by osteoclast is repaired by osteogenesis by osteoblast. This series of phenomena are called remodeling of bone, and by the remodeling, old bones are replaced by new bones, thus maintaining the strength of the entire bone while maintaining calcium homeostasis.

PTH is a hormone that plays a key role in maintaining the calcium homeostasis. When blood $Ca^{2+}$ concentration decreases, secretion of PTH from the parathyroid gland is promoted immediately, which, in the bone, acts on osteoblast (activation of osteoclast by osteoblast, production of bone organic matrix decomposition enzyme and the like) to promote osteoclastic bone resorption, whereby $Ca^{2+}$ is transferred from the bone into the blood. In kidney, PTH promotes resorption of $Ca^{2+}$ in the distal convulted tubule, and hydroxylates 25(OH) vitamin $D_3$ at $1\alpha$ position in the proximal tubule, thereby promoting the production of active vitamin $D_3$ [$1\alpha$, $25(OH)_2D_3$] having a function of promoting absorption of $Ca^{2+}$ from the intestine. It also suppresses resorption of phosphorus in kidney. As mentioned above, PTH directly or indirectly increases blood $Ca^{2+}$ concentration.

When blood $Ca^{2+}$ concentration increases, calcium receptor senses it, immediately suppresses secretion of PTH from the parathyroid gland to decrease the amount of $Ca^{2+}$ to be supplied into the blood [see, Brown, E. M., Homeostatic mechanisms regulating extracellular and intracellular calcium metabolism, in the parathyroids, p. 19, (1994), Raven press, New York]. Secretion of PTH is also suppressed by active vitamin D [$1\alpha$, $25(OH)_2D_3$].

Because PTH is a hormone assuming an important role in controlling $Ca^{2+}$ metabolism and bone metabolism, attempts have been made to apply PTH to the treatment of osteoporosis. In 1982, Tam et al. found that sustained administration of bovine PTH (1-84) to thyroid/parathyroid gland enucleated rat results in promotion of both osteogenesis and bone resorption of femoral cancellous bone, leading to a decrease in net bone mass, but subcutaneous intermittent administration thereof does not result in promotion of bone resorption but in promotion of osteogenesis alone, leading to an increase in the bone mass [see, Endocrinology, 110, 506-512 (1982)]. Furthermore, Uzawa et al. compared the actions of sustained administration and intermittent administration of PTH with regard to epiphyseal long bone and metaphyseal cancellous bone of young rat. As a result, they clarified that sustained administration of PTH results in remarkable increase in bone mass in metaphyseal cancellous bone highly susceptible to the effect of enchondral ossification, though associated with abnormal findings such as hyperplasia of epiphyseal plate cartilage, fibrous ostitis and the like, and in marked promotion of bone resorption and decrease in bone mass accompanied by rarefaction of cortical bone, in epiphyseal cancellous bone where the effect is small [see, Bone, 16, 477-484 (1995)]. In addition, it has been reported that intermittent administration of PTH results in significant increases in bone mass and bone trabecula in both epiphyseal and metaphyseal cancellous bones without increase in osteoclast or decrease of cortical bone.

Moreover, Scutt et al. have reported that, in chicken calvaria derived osteoblast, a short time (10-20 min) treatment with PTH promotes cell growth as compared to a long time (18 hr) treatment [Calcified Tissue International, 55, 208-215 (1994)]. This suggests that some of the actions of PTH on osteoblast are temporary and that expression of the action by the treatment for an extremely short time may be related to the fact that sustained administration and intermittent administration of PTH in vivo show different actions on bone tissues.

Ishizuya et al. further clarified through investigation of the action of PTH on differentiation of osteoblast using an in vitro experiment system that the action of PTH varies depending on the treatment time. They have reported that sustained action of PTH on osteoblast derived from rat calvaria resulted in strong inhibition of differentiation of osteoblast and nearly complete inhibition of osteogenesis in vitro, but repeated PTH action for the first 6 hr of 48 hr as one cycle resulted in significant promotion of differentiation of osteoblast and promotion of osteogenesis in vitro.

PTH is considered to not only prevent decrease in bone mass of osteoporosis model, but also has a bone mass recovery effect even on an animal already suffering from marked decrease in bone mass. Wronski et al. intermittently administered human PTH (1-34) to 90-day-old SD rat at 4 weeks post-ovariectomy and showing an obvious decrease in cancellous bone, for 15 weeks from 4 weeks post-ovariectomy. As a result, promotion of osteogenesis and inhibition of bone resorption were observed during the period of from week 5 to week 10 after the start of the administration, showing increased bone mass of about twice the bone mass of sham operation group [see, Endocrinology, 132, 823-831 (1993)]. They have also reported that, in this experiment, estrogen and bisphosphonate prevented decrease in bone mass caused by ovariectomy but did not show increase in bone mass, unlike PTH. They analyzed in detail the cortical bone of this experiment system and found images showing promoted osteogenesis and bone mass increase on the periost side and endosteum side by intermittent administration of human PTH (1-34), based on which they have clarified that the increase in cancellous bone due to PTH did not accompany decrease in cortical bone [see, Bone, 15, 51-58 (1994)].

Furthermore, Mosekilde et al. have reported that intermittent administration of human PTH (1-34) or human PTH (1-84) causes not only an increase in bone mass but also a dose-dependent increase in compression strength and bending strength, which are indices of bone substance, of cancellous bone [see, Endocrinology, 129, 421-428 (1991)] and cortical bone [see, Journal of Bone and Mineral Research, 8, 1097-1101 (1993)] of rat vertebral bone. As discussed above, since PTH shows an obvious bone mass increasing action in experimental animals, various investigations are ongoing as regards the restrictive conditions expected in actual clinical applications. Mizoguchi studied whether or not a pharmacological effect is observed by intermittent administration of PTH, even when PTH in blood, which is considered to be one of the factors responsible for osteoporosis, has significantly increased, and concluded that the bone mass increased as usual [see, Journal of Japanese Society of Bone Morphometry, vol. 5, pp. 33-39 (1995)]. Takao et al. have studied the frequency of PTH administration and reported that administration of once a week for 12 weeks to healthy rat scarcely promoted bone resorption but dose-dependently increased the bone mass [see, Japanese Journal of Bone Metabolism, vol. 12 (Suppl.), p. S343 (1994)], suggesting possible effectiveness of clinically useful low frequency administration. The foregoing achievements suggest the possibility of PTH for making a potent and promising therapeutic drug for the treatment of postmenopausal osteoporosis or postovariectomy osteoporosis, which increases bone mass and decreases bone fracture rate.

These results clearly indicate that intermittent administration of PTH would enable treatment of osteoporosis. On the other hand, PTH problematically requires injection as an administration route, which is painful for many patients. However, an orally administrable pharmaceutical agent that can intermittently increase PTH concentration in blood is greatly expected to become a therapeutic drug of osteoporosis, which is based on a new action mechanism different from that of the above-mentioned PTH and conventional calcitonin.

Calcium receptor is a G protein coupled receptor, which is cloned as a molecule essential for controlling PTH secretion, and which penetrates cell membrane 7 times. Human calcium receptor consists of 1078 amino acids, and shows 93% amino acid homology with bovine calcium receptor. Human calcium receptor consists of a large N terminal extracellular region consisting of 612 amino acids, a cell membrane penetration region consisting of 250 amino acids and a C terminal intracellular region consisting of 216 amino acids. Expression of calcium receptor has been found in parathyroid gland, kidney, thyroid C cell, brain and the like, as well as in bone (bone marrow cells).

When calcium receptor is bound with a ligand such as $Ca^{2+}$ and the like, it activates phospholipase C in conjugation with G protein, causes production of inositol triphosphate and increase in intracellular $Ca^{2+}$ concentration, and as a result, suppresses secretion of PTH [see, Nature, 366, 575-580 (1993)].

As mentioned above, a pharmaceutical agent that inhibits activation of calcium receptor, or a pharmaceutical agent that antagonizes calcium receptor, removes suppression of PTH secretion in parathyroid gland cells, and promotes secretion of PTH. It is considered that, if the antagonistic action can increase blood PTH concentration discontinuously and intermittently, its antagonist is expected to show the same effect as that provided by intermittent administration of PTH, and a pharmaceutical agent extremely effective for the treatment of osteoporosis can be provided.

In contrast, cytochrome (cytochrome P450, hereinafter P450) is a protein having a molecular weight of about 50,000, which contains protoheme, and its physical functions vary over a wide range. For example, it has a function of an enzyme catalyzing various reactions in the drug metabolism. CYP2D6 belonging to the family of P450 (CYP) is an important enzyme for human drug metabolism, and is involved in the metabolism of many compounds. When a drug inhibiting the metabolic function of CYP2D6 is administered, the drug is accumulated in the body and may exert a strong influence. Accordingly, a compound having a weak inhibitory action on the metabolic function of CYP2D6 is desirable as a drug.

Heretofore, various compounds useful as CaSR antagonists have been reported.

Specifically, for example, a compound represented by the following formula

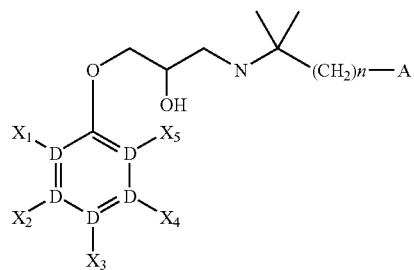

[wherein A is aryl etc., D is C or N, $X_1$ and $X_5$ are each hydrogen, cyano etc., and $X_2$, $X_3$ and $X_4$ are each hydrogen, halogen, $C_{1-4}$ alkyl etc.] (WO 02/38106) is mentioned.

In addition, a compound represented by the following formula

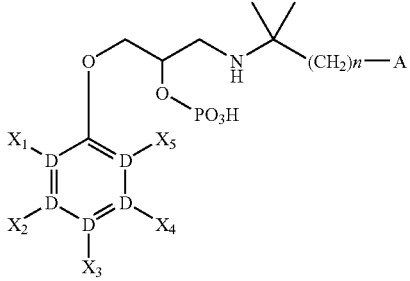

[wherein A is aryl etc., D is C or N, $X_1$ and $X_5$ are each hydrogen, cyano etc., $X_2$ is hydrogen etc., and $X_3$ and $X_4$ are each hydrogen, $C_{1-4}$ alkyl etc.] (WO 02/34204) is mentioned.

Furthermore, a compound represented by the following formula

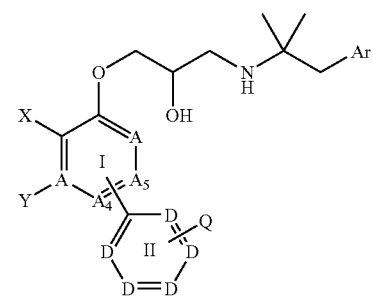

[wherein A is C or N, D is C or N, X is cyano, nitro etc., Y is chlorine, fluorine etc., and Ar is phenyl, naphthyl etc.] (WO 02/07673) is mentioned.

In addition, a compound represented by the following formula

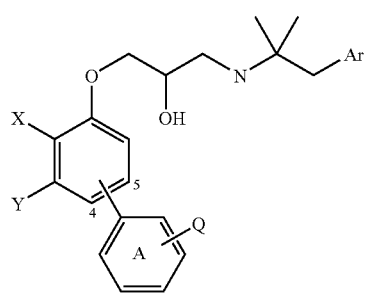

[wherein X is cyano, nitro etc., Y is chlorine, fluorine etc., and Ar is phenyl, naphthyl etc.] (JP 2002-536330-T, WO 00/45816, EP 1148876-A, U.S. Pat. No. 6,417,215), and a compound represented by the following formula

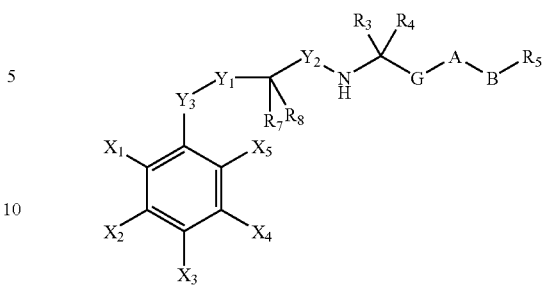

[wherein $X_1$, $X_2$, $X_3$, $X_4$ and $X_5$ are each H, halogen and the like, $Y_1$ is a covalent bond, or a non-substituted, etc., $Y_2$ is a non-substituted or $C_{1-4}$ alkyl etc., $Y_3$ is a covalent bond, O etc., $R_3$ and $R_4$ are each independently methyl, ethyl etc., $R_5$ is aryl, fused aryl etc., $R_7$ is H, OH etc., $R_8$ is H, $C_{1-4}$ alkyl etc., A and B are independently a bond, $CH_2$ etc., G is a covalent bond, $CHR_6$ ($R_6$ is H etc.) etc.] (JP 2002-510671-T, WO 99/51569, EP 1070048-A, U.S. Pat. No. 6,395,919) are described.

As a CaSR antagonist, a compound represented by the following formula

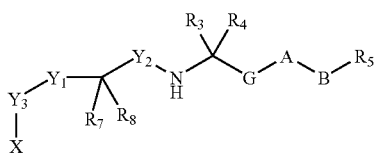

[wherein X is represented by the following formua

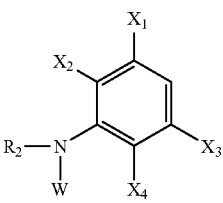

(wherein $X_1$, $X_2$, $X_3$ and $X_4$ are each independently CN, $NO_2$ etc., then W is $R_1$, $SO_2R_1$ etc., $R_2$ is H, $C_{1-4}$ alkyl etc.) and the like, $Y_1$ is a covalent bond, or a non-substituted etc., $Y_2$ is a non-substituted or $C_{1-4}$ alkyl etc., $Y_3$ is a covalent bond, O etc., $R_3$ and $R_4$ are independently methyl, ethyl etc., $R_5$ is heteroaryl, fused heteroaryl etc., $R_7$ is H, OH etc., $R_8$ is H, $C_{1-4}$ alkyl etc., A and B are each independently a bond, $CH_2$ etc., and G is a covalent bond, $CHR_6$ ($R_6$ is H etc.) etc.] (JP 2002-510636-T, WO 99/51241, EP 1069901-A, US 2002052509-A) is described.

As a CaSR antagonist, a compound represented by the following formula

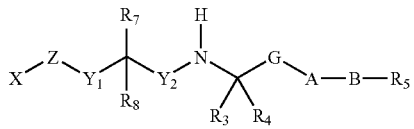

[wherein $Y_1$ is a covalent bond or a non-substituted etc., $Y_2$ is a non-substituted or $C_{1-4}$ alkyl etc., Z is a covalent bond, O etc., $R_3$ and $R_4$ are each independently methyl, ethyl etc., $R_5$ is phenyl, naphthyl etc., G is a covalent bond or C—$R_6$ (wherein $R_6$ is H, OH etc.), $R_7$ is H, OH etc., $R_8$ is H, $C_{1-4}$ alkyl etc., A-B moiety is $CH_2CH_2$, a covalent bond etc., and X is a following formula

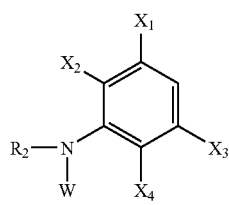

(wherein W is $R_1$, $SO_2R_1$ (wherein $R_1$ is hydrogen, $C_{1-4}$ alkyl etc.), and the like, $X_1$, $X_2$, $X_3$ and $X_4$ are each independently CN, $NO_2$ etc., $R_2$ is hydrogen, $C_{1-4}$ alkyl etc.), and the like] (JP 2001-523223-T, WO 98/45255, EP 973730-A, U.S. Pat. No. 6,294,531), as a CaSR antagonist, a compound represented by the following formula

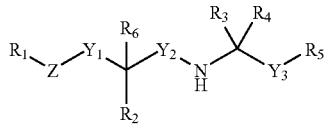

[wherein $R_1$ is aryl etc., $R_2$ is hydroxyl group etc., $R_3$ and $R_4$ are each lower alkyl etc., $R_5$ is substituted naphthyl, substituted phenyl etc., $Y_1$ is alkylene etc., $Y_2$ is alkylene, $Y_3$ is alkylene and Z is oxygen etc.] (JP 2001-501584-T, WO 97/37967, EP 901459-A, U.S. Pat. No. 6,022,894), a compound represented by the following formula

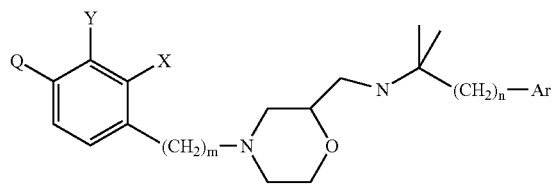

[wherein X is nitro etc., Y is hydrogen etc., Q is $C_{1-4}$ alkyl etc., Ar is phenyl, naphthyl etc., m is 0-2 and n is 1-3] (JP 2002-522499-T, WO 00/09132, EP 1112073-A), and a compound represented by the following formula

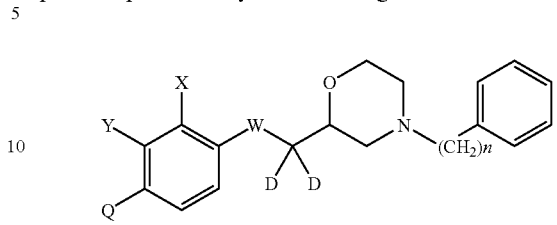

[wherein X is cyano etc., Y is chlorine etc., Q is hydrogen is etc., W is oxygen etc., D is hydrogen etc. and n is 2-4] (JP 2002-522532-T, WO 00/09491, EP 1104411-A) are described.

Maxine Gowen et al. administered a compound having a CaSR antagonistic action, which is called NPS-2143,

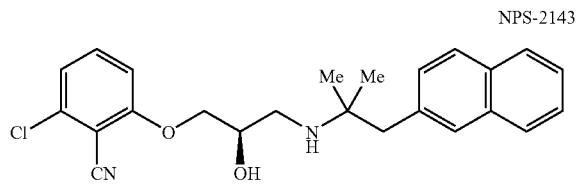

to OVX rats orally and measured blood concentration and bone density thereof, thereby testing the effect of NPS-2143 on osteogenesis, and reported the results thereof (see, The Journal of Clinical Investigation, vol. 105, pp. 1595-1604 (2000)).

According to the report, NPS-2143 significantly promotes release of PTH, but it did not show any direct effect on osteoblast and osteoclast in vitro and was free of bone decrease or bone increase. One of the reasons pointed out therefor is too long a half-life of NPS-2143 in blood. That is, when rat PTH (1-34) was administered to OVX rat at the dose of 5 μg/kg, blood PTH concentration reached the peak of about 175 pg/ml in 30 minutes and returned to the original level in 2 hours, but when NPS-2143 was administered at the dose of 100 μmol/kg, the blood PTH concentration reached about 115 pg/ml in 30 minutes and kept increasing and showed about 140 pg/ml even 4 hours later (see, The Journal of Clinical Investigation, vol. 105, p. 1595-1604 (2000), especially p. 1598, FIG. 3).

At that time, the blood concentration of NPS-2143 itself was maintained at the level of not less than 100 ng/ml even 8 hours after the administration. It was 24 hours later when the concentration became 10 ng/ml or below the undetectable level.

The above-mentioned Maxine Gowen et al. reference teaches that a calcium receptor antagonist having a too long blood half-life provides results as in continuous administration of PTH, where a bone mass increase cannot be expected. Thus, most of the conventional calcium receptor antagonists continuously increase the blood PTH concentration and cannot be expected to provide a sufficient osteogenesis promoting action. Of the conventional calcium receptor antagonists, a compound represented by the following formula [I]

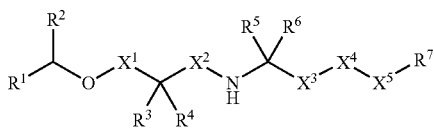

[wherein R¹ is optionally substituted aryl group etc., R² is $C_{1-6}$ alkyl group, $C_{3-7}$ cycloalkyl group etc., R³ is hydroxyl group etc., R⁴ is hydrogen atom etc., R⁵ and R⁶ are $C_{1-6}$ alkyl group etc., R⁷ is optionally substituted aryl group etc., X¹ is a single bond, $C_{1-6}$ alkylene etc., X² is optionally substituted $C_{1-6}$ alkylene, X³ is a single bond or optionally substituted $C_{1-6}$ alkylene, and X⁴ and Xs are linked to form a single bond, methylene etc.], which has a superior calcium receptor antagonistic action, which can be administered orally and intermittently, and which can increase blood PTH concentration discontinuously and intermittently, is disclosed (WO02/14259). By comparison of the activities of a compound within the scope disclosed in this publication and the compound of the present invention, the compound of the present invention was surprisingly found to have a higher activity and to be a compound having a lower inhibitory action on the metabolic enzyme CYP2D6.

However, there are not many reports on such an effective compound, and further study is desired.

The present invention aims at providing a compound having a superior calcium receptor antagonistic action, which can be administered orally, and which can increase blood PTH concentration discontinuously and intermittently. The present invention also aims at providing a pharmaceutical composition permitting oral administration and intermittent administration, which comprises this compound, and which is effective as a therapeutic drug for a disease accompanying abnormal calcium homeostasis, or osteoporosis, hypoparathyroidism, osteosarcoma, periodontitis, bone fracture, osteoarthrisis, chronic rheumatoid arthritis, Paget's disease, humoral hypercalcemia syndrome, autosomal dominant hypocalcemia and the like, particularly a therapeutic drug for osteoporosis.

DISCLOSURE OF THE INVENTION

To solve the above-mentioned problems, the present inventors have conducted intensive studies and, as a result, found that a compound represented by the following formula (1) or (1') has a superior calcium receptor antagonistic action, and can be administered orally, which resulted in the completion of the present invention. A compound represented by the following formula (1) or (1') can surprisingly increase the blood PTH concentration discontinuously and intermittently, and is greatly expected to have practicality as a superior therapeutic drug for osteoporosis.

As is clear from the following Experimental Examples, the compound of the present invention is superior in calcium receptor antagonistic action, and also has a noncontinuous and transitional PTH secretagogue action. Accordingly, by administration of the compound of the present invention, a similar effect as in the intermittent administration of the PTH can be achieved, which is considered to be extremely effective for the treatment of osteoporosis. In addition, as shown in the Experimental Examples below, the compound of the present invention shows a weak inhibitory action on the metabolic function of CYP2D6, which is desirable as a pharmaceutical product. The PTH secretagogue action of the present invention was shown even low dose compared with a compound as known before. The compound of the present invention was improved a property of oral absorption and solubility. It is also clear that the compound of the present invention has a weak side effect.

The present invention relates to a compound represented by the following formula (1) or (1)', a calcium receptor antagonist and a therapeutic drug for osteoporosis, which comprise this compound as an active ingredient. More particularly, the present invention provides the following [1] to [12].

[1] A compound represented by the following formula (1), an optically active form thereof, or a pharmaceutically acceptable salt thereof:

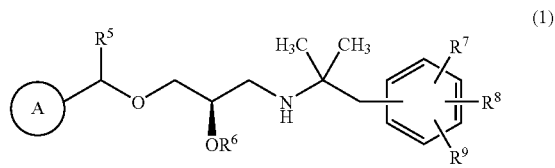

ring A is a $C_{3-6}$ cycloalkyl group,

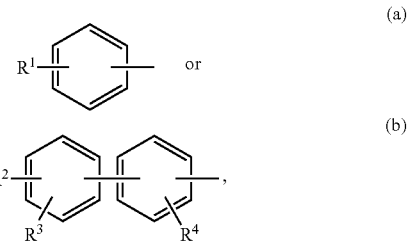

wherein R¹ is a $C_{1-6}$ alkyl group or $R^4O—C(=O)—X—(O)n-$[wherein $R^A$ is a hydrogen atom, a $C_{1-6}$ alkyl group or $R^BO—C(=O)O—C_{1-6}$ alkylene- (wherein $R^B$ is a $C_{1-6}$ alkyl group or a $C_{3-6}$ cycloalkyl group), X is a $C_{1-6}$ alkylene group, a $C_{2-4}$ alkenylene group, a $C_{2-4}$ alkynylene group,

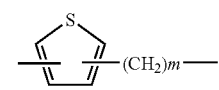

(wherein m is an integer of 0 to 6) or

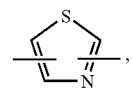

and n is 0 or 1],

R² is a hydroxy-$C_{1-6}$ alkyl group, a carboxy-$C_{3-6}$ alkyl group, a $C_{1-6}$ alkoxy-carbonyl-$C_{1-6}$ alkyl group, a carbamoyl-$C_{1-6}$ alkyl group, a $C_{1-7}$ acylamino-$C_{1-6}$ alkyl group, a carbamoyl group, a hydroxycarbamoyl group, a $C_{1-6}$ alkyl-sulfonyl-carbamoyl group, a nitro group, an amino group, an oxalo group, a phosphoric acid group optionally esterified by a $C_{1-6}$ alkyl group, $R^4O\!-\!C(\!=\!O)\!-\!$ ($R^4$ is as defined above) or a 5- or 6-membered heterocyclic residue having 1 to 4 hetero atoms selected from the group consisting of a nitrogen atom, an oxygen atom and a sulfur atom (said heterocyclic residue is optionally substituted by an oxo group), $R^3$ and $R^4$ are the same or different and each is a hydrogen atom, a cyano group, a halogen atom, a $C_{1-6}$ alkyl group, a $C_{1-6}$ alkoxy group, a halo $C_{1-6}$ alkyl group or a halo $C_{1-6}$ alkoxy group, $R^5$ is a $C_{1-6}$ alkyl group or a $C_{3-6}$ cycloalkyl group, $R^6$ is a hydrogen atom or $R^C$ (wherein $R^C$ is a $C_{1-7}$ acyl group optionally substituted by a carboxyl group), $R^7$, $R^8$ and $R^9$ are the same or different and each is a hydrogen atom, a $C_{1-6}$ alkyl group, a $C_{2-4}$ alkenyl group, a halogen atom, a halo $C_{1-6}$ alkyl group, a $C_{1-6}$ alkoxy group, a halo $C_{1-6}$ alkoxy group, or a carboxyl group, or the adjacent $R^7$ and $R^8$ are joined to form —CH=CH—CH=CH—, provided that (1) when ring A is a group of the formula (a) and $R^1$ is a $C_{1-6}$ alkyl group, then $R^6$ is $R^C$, (2) when ring A is a group of the formula (b) and $R^2$ is a carboxyl group or a $C_{1-6}$ alkoxy-carbonyl group, then $R^7$ is a $C_{2-4}$ alkenyl group, (3) when ring A is a group of the formula (b) and $R^2$ is a hydroxycarbamoyl group, then $R^3$ is a hydrogen atom, or (4) when ring A is a group of the formula (a), $R^1$ is $R^4O\!-\!C(\!=\!O)\!-\!X\!-\!(O)n\!-$ and X is

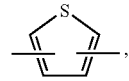

then n is 0.

[2] The compound of the above-mentioned [1], wherein ring A is

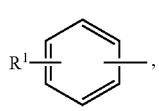
(a)

$R^1$ is a $C_{1-6}$ alkyl group or $R^4O\!-\!C(\!=\!O)\!-\!X\!-\!(O)n\!-$ [wherein $R^4$ is a hydrogen atom, X is a $C_{1-6}$ alkylene group, a $C_{2-4}$ alkenylene group, a $C_{2-4}$ alkynylene group,

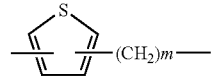

(wherein m is an integer of 0 to 6) or

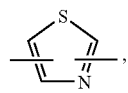

and n is 0], $R^5$ is a $C_{1-6}$ alkyl group or a $C_{3-6}$ cycloalkyl group, $R^6$ is a hydrogen atom, $R^7$, $R^8$ and $R^9$ are the same or different and each is a hydrogen atom, a $C_{1-6}$ alkyl group, a $C_{2-4}$ alkenyl group, a halogen atom, a halo $C_{1-6}$ alkyl group, a $C_{1-6}$ alkoxy group, a halo $C_{1-6}$ alkoxy group, or a carboxyl group, or the adjacent $R^7$ and $R^8$ are joined to form —CH=CH—CH=CH—, an optically active form thereof, or a pharmaceutically acceptable salt thereof.

[3] The compound of the above-mentioned [1], wherein ring A is

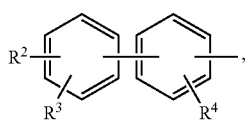
(b)

$R^2$ is a hydroxy-$C_{1-6}$ alkyl group, a carboxy-$C_{1-6}$ alkyl group, a $C_{1-6}$ alkoxy-carbonyl-$C_{1-6}$ alkyl group, a carbamoyl-$C_{1-6}$ alkyl group, a $C_{1-7}$ acylamino-$C_{1-6}$ alkyl group, a carbamoyl group, a hydroxycarbamoyl group or an amino group, $R^3$ and $R^4$ are the same or different and each is a hydrogen atom, a cyano group, a halogen atom, a $C_{1-6}$ alkyl group, a $C_{1-6}$ alkoxy group, a halo $C_{1-6}$ alkyl group or a halo $C_{1-6}$ alkoxy group, $R^5$ is a $C_{1-6}$ alkyl group or a $C_{3-6}$ cycloalkyl group, $R^6$ is a hydrogen atom, $R^7$, $R^8$ and $R^9$ are the same or different and each is a hydrogen atom, a $C_{1-6}$ alkyl group, a $C_{2-4}$ alkenyl group, a halogen atom, a halo $C_{1-6}$ alkyl group, a $C_{1-6}$ alkoxy group, a halo $C_{1-6}$ alkoxy group, or a carboxyl group, or the adjacent $R^7$ and $R^8$ are joined to form —CH=CH—CH=CH—, an optically active form thereof, or a pharmaceutically acceptable salt thereof.

[4] The compound of the above-mentioned [1], which is selected from the group consisting of the following structural formulas, an optically active form thereof, or a pharmaceutically acceptable salt thereof:
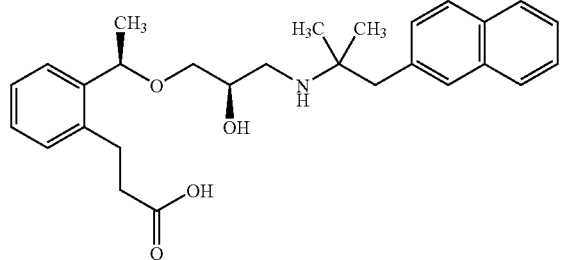
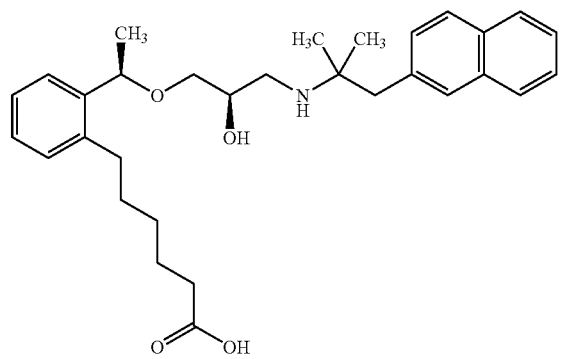
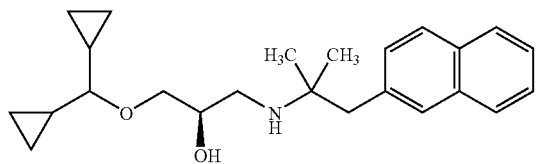
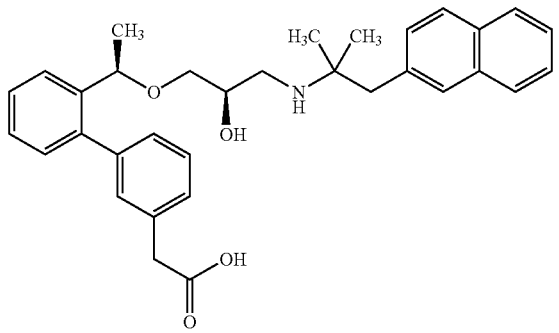
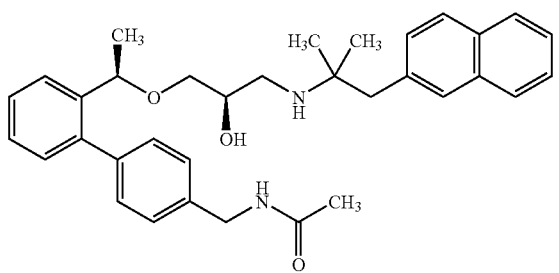
-continued
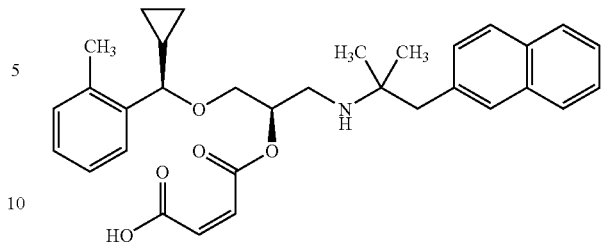
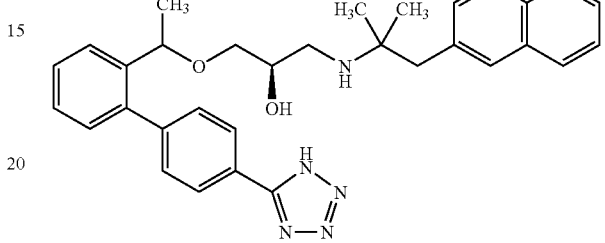
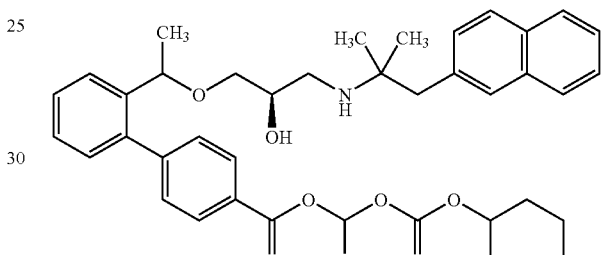
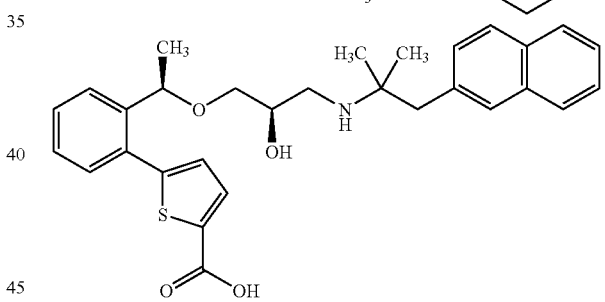
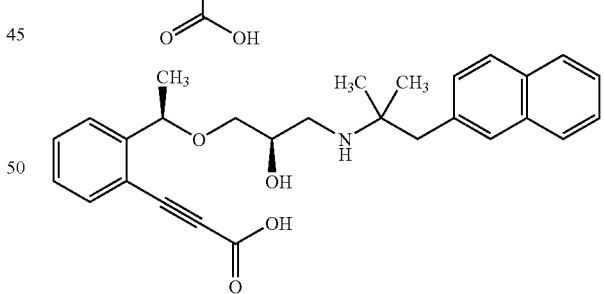
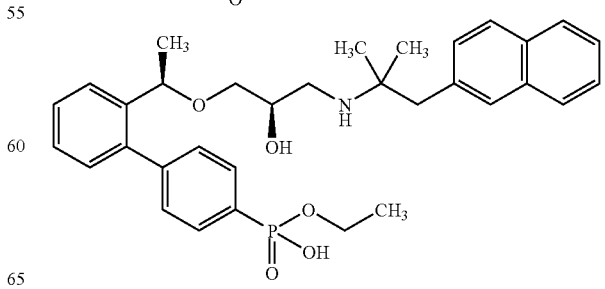

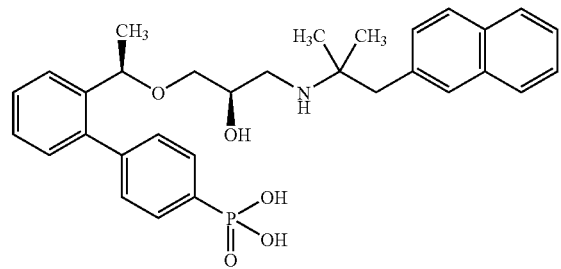
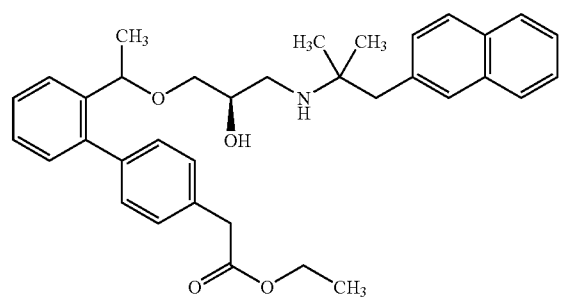
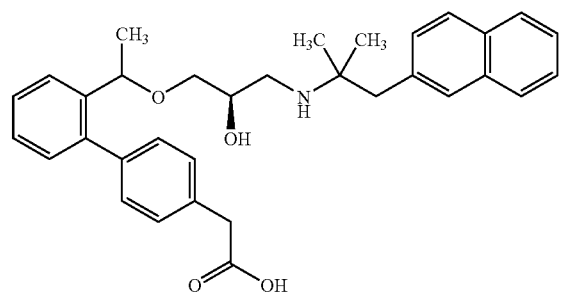
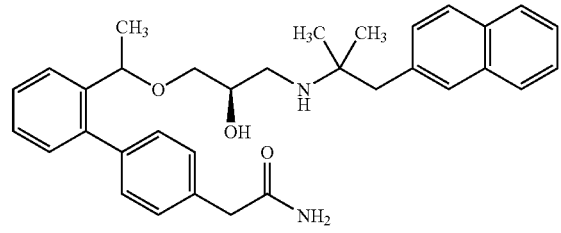
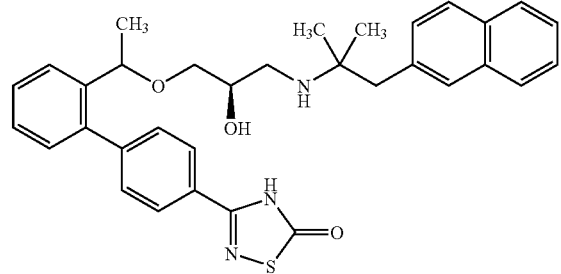
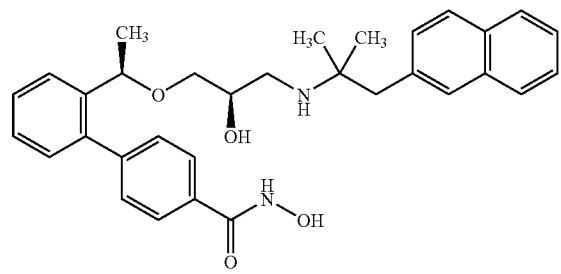
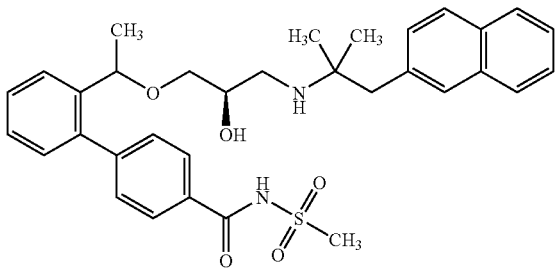
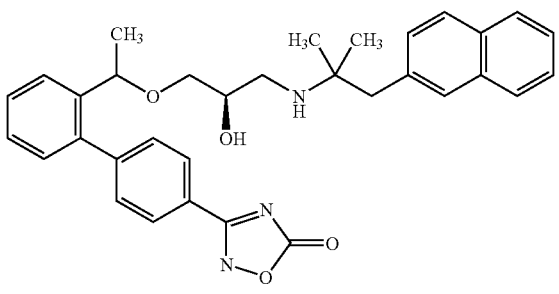
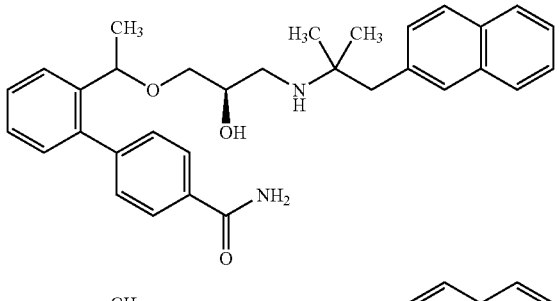
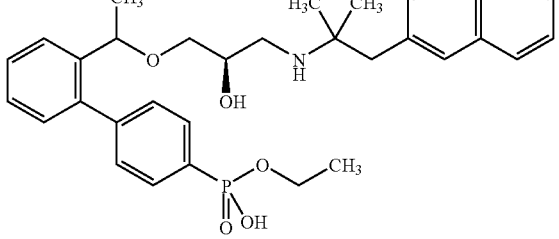
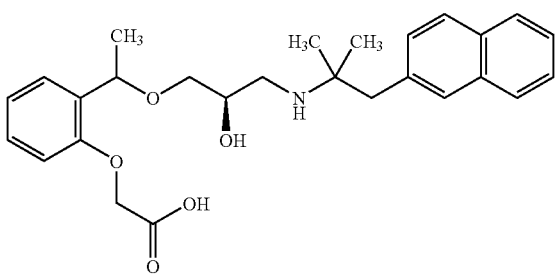
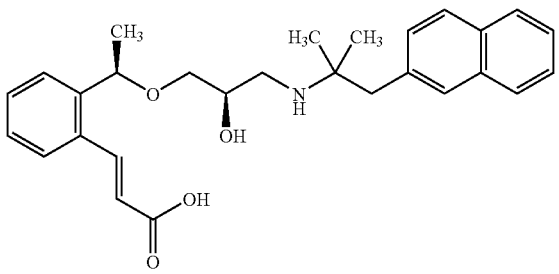

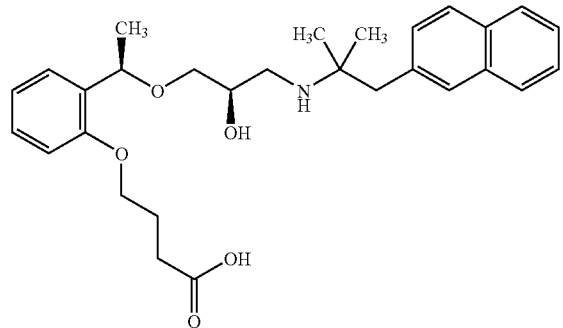
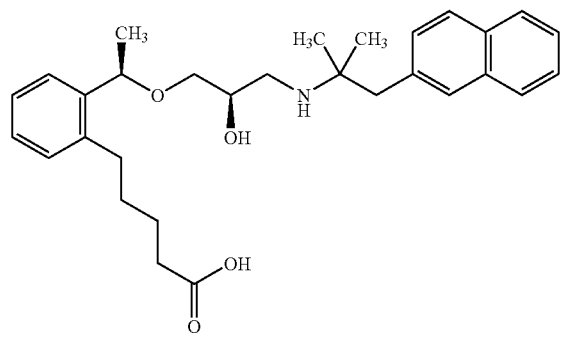
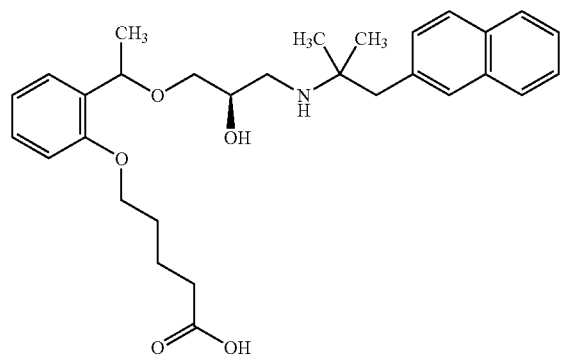
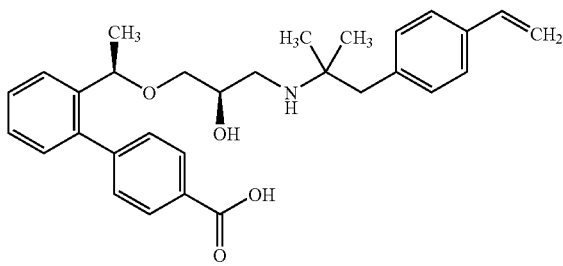
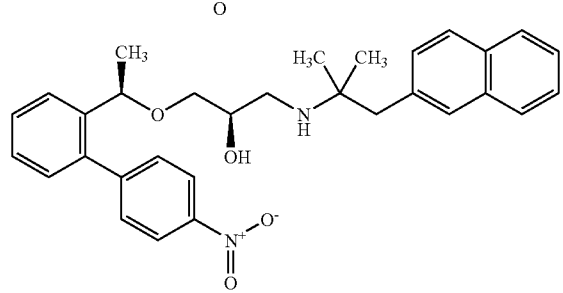
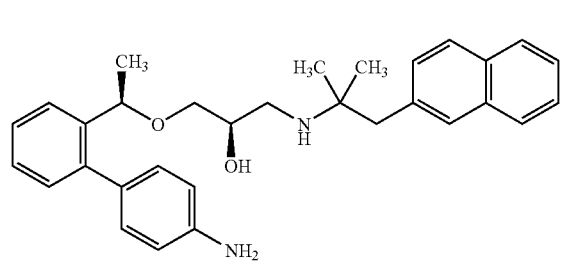
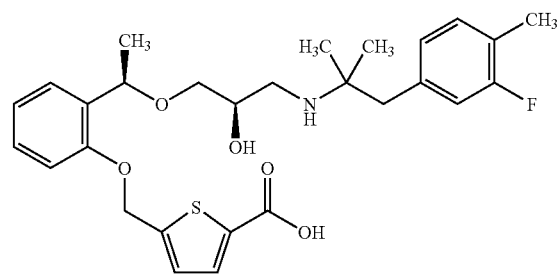
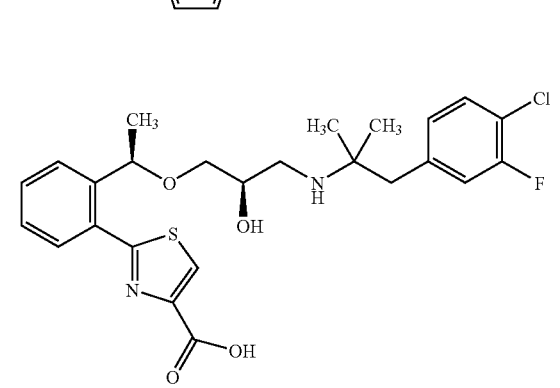
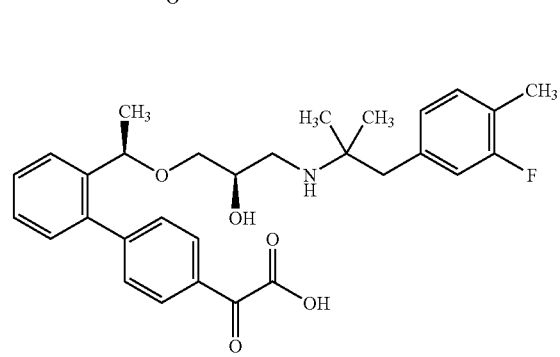
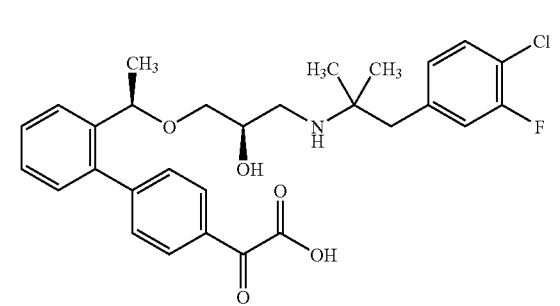

[5] A compound represented by the following formula (1'), a pharmaceutically acceptable salt thereof or an optically active form thereof:

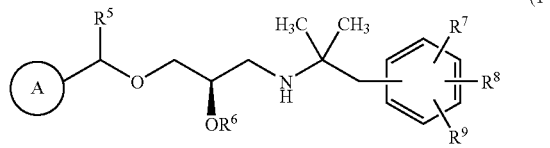

ring A is a $C_{3-6}$ cycloalkyl group,

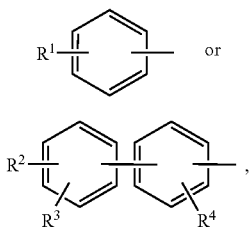

$R^1$ is a $C_{1-6}$ alkyl group or $R^AO—C(=O)—X—(O)n-$ [wherein $R^A$ is a hydrogen atom, a $C_{1-6}$ alkyl group or $R^BO—C(=O)O—C_{1-6}$ alkylene- (wherein $R^B$ is a $C_{1-6}$ alkyl group or a $C_{3-6}$ cycloalkyl group), X is a $C_{1-6}$ alkylene group, a $C_{2-4}$ alkenylene group, a $C_{2-4}$ alkynylene group, or

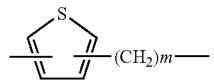

(wherein m is an integer of 0 to 6), and n is 0 or 1], $R^2$ is a hydroxy-$C_{1-6}$ alkyl group, a carboxy-$C_{1-6}$ alkyl group, a $C_{1-6}$ alkoxy-carbonyl-$C_{1-6}$ alkyl group, a carbamoyl-$C_{1-6}$ alkyl group, a $C_{1-7}$ acylamino-$C_{1-6}$ alkyl group, a carbamoyl group, a hydroxycarbamoyl group, a $C_{1-6}$ alkylsulfonyl-carbamoyl group, a nitro group, an amino group, a phosphoric acid residue optionally esterified by a $C_{1-6}$ alkyl group, $R^AO—C(=O)—$ ($R^A$ is as defined above) or a 5- or 6-membered heterocyclic residue having 1 to 4 hetero atoms selected from the group consisting of a nitrogen atom, an oxygen atom and a sulfur atom (said heterocyclic residue is optionally substituted by an oxo group), $R^3$ and $R^4$ are the same or different and each is a hydrogen atom, a cyano group, a halogen atom, a $C_{1-6}$ alkyl group or a $C_{1-6}$ alkoxy group, $R^5$ is a $C_{1-6}$ alkyl group or a $C_{3-6}$ cycloalkyl group, $R^6$ is a hydrogen atom or $R^C$ (wherein $R^C$ is a $C_{1-7}$ acyl group optionally substituted by a carboxyl group), $R^7$, $R^8$ and $R^9$ are the same or different and each is a hydrogen atom, a $C_{1-6}$ alkyl group, a $C_{2-4}$ alkenyl group, a halogen atom, a halo $C_{1-6}$ alkyl group, a $C_{1-6}$ alkoxy group, a halo $C_{1-6}$ alkoxy group, or a carboxyl group, or the adjacent $R^7$ and $R^8$ are joined to form —CH=CH—CH=CH—, provided that (1) when ring A is a group of the formula (a) and $R^1$ is a $C_{1-6}$ alkyl group, then $R^6$ is $R^C$, (2) when ring A is a group of the formula (b) and $R^2$ is a carboxyl group or a $C_{1-6}$ alkoxy-carbonyl group, then $R^7$ is a $C_{2-4}$ alkenyl group, (3) when ring A is a group of the formula (b) and $R^2$ is a hydroxycarbamoyl group, then $R^3$ is a hydrogen atom, or (4) when ring A is a group of the formula (a), $R^1$ is $R^AO—C(=O)—X—(O)n-$ and X is

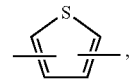

then n is 0.

[6] A pharmaceutical composition comprising a compound of the above-mentioned [1] to [5], an optically active form thereof, or a pharmaceutically acceptable salt thereof.

[7] A pharmaceutical composition comprising a pharmaceutically acceptable carrier, and a compound of the above-mentioned [1] to [5], an optically active form thereof, or a pharmaceutically acceptable salt thereof as an active ingredient.

[8] A therapeutic drug for osteoporosis, which comprises a pharmaceutically acceptable carrier, and a compound of the above-mentioned [1] to [5], an optically active form thereof, or a pharmaceutically acceptable salt thereof as an active ingredient.

[9] The therapeutic drug of the above-mentioned [8], which is used in combination with other therapeutic drug for osteoporosis.

[10] The therapeutic drug of the above-mentioned [9], wherein said other therapeutic drug for osteoporosis is selected from the group consisting of a calcium agent, a vitamin D preparation, a vitamin K preparation, a female hormone preparation, an estrogen antagonist preparation, an anabolic steroid preparation, a parathyroid hormone preparation, a calcitonin preparation, a bisphosphonate preparation and an ipriflavone preparation.

[11] A method of treating osteoporosis, which comprises administering an effective amount of a compound of the above-mentioned [1] to [5], an optically active form thereof, or a pharmaceutically acceptable salt thereof to a patient with osteoporosis.

[12] A calcium receptor antagonist comprising a pharmaceutically acceptable carrier, and a compound of the above-mentioned [1] to [5], an optically active form thereof, or a pharmaceutically acceptable salt thereof as an active ingredient.

DETAILED DESCRIPTION OF THE INVENTION

The terms used in the present specification are defined as follows.

The "halogen atom" is fluorine atom, chlorine atom, bromine atom or iodine atom, which is preferably fluorine atom or chlorine atom, particularly preferably chlorine atom.

The "$C_{1-6}$ alkyl group" is straight chain or branched chain alkyl group having 1 to 6, preferably 1 to 4, carbon atoms. Examples thereof include $C_{1-4}$ alkyl group selected from methyl group, ethyl group, propyl group, isopropyl group, butyl group, isobutyl group, tert-butyl group, pentyl group, isopentyl group, tert-pentyl group or hexyl group and the like, preferably methyl group, ethyl group, propyl group, isopropyl group, butyl group, isobutyl group and tert-butyl group. As $R_1$, methyl group is preferable. As $R_3$ and $R_4$, methyl group and ethyl group are preferable, and methyl group is particularly preferable. As $R_5$, methyl group is preferable. As $R_6$, $R_7$ and $R_8$, methyl group is preferable. As $R_B$, methyl group, ethyl group, propyl group, isopropyl group and butyl group are preferable, and methyl group and ethyl group are particularly preferable.

The "halo $C_{1-6}$ alkyl group" is a haloalkyl group wherein the aforementioned "$C_{1-6}$ alkyl group" is substituted by one or more halogen atoms, and the position of substitution is free of any particular limitation as long as it is chemically acceptable. Examples of the "halo $C_{1-6}$ alkyl group" include fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, 2-fluoroethyl group, 2,2-difluoroethyl group, 2,2,2-trifluoroethyl group, 2-chloroethyl group, 2,2-dichloroethyl group, 2,2,2-trichloroethyl group, 2-bromomethyl group, 2,2-dibromoethyl group, 2,2,2-tribromoethyl group, 3-chloropropyl group or 4-chlorobutyl group and the like, preferably halo $C_{1-2}$ alkyl group such as trifluoromethyl group and 2,2,2-trichloroethyl group, particularly preferably trifluoromethyl group.

The "hydroxy-$C_{1-6}$ alkyl group" is a hydroxyalkyl group wherein the aforementioned "$C_{1-6}$ alkyl group" is substituted by hydroxyl group, and the position of substitution is not particularly limited as long as it is chemically acceptable. As the "hydroxy-$C_{1-6}$alkyl group", for example, hydroxymethyl group, 1-hydroxyethyl group, 2-hydroxyethyl group, 1-hydroxypropyl group, 2-hydroxypropyl group, 3-hydroxypropyl group, 2-hydroxy-1-methylethyl group, 1-hydroxybutyl group, 2-hydroxybutyl group, 3-hydroxybutyl group, 4-hydroxybutyl group, 3-hydroxy-2-methylpropyl group, 2-hydroxy-1,1-dimethylethyl group, 5-hydroxypentyl group or 6-hydroxyhexyl group and the like can be mentioned, with preference given to a hydroxy-$C_{1-4}$ alkyl group selected from hydroxymethyl group, 2-hydroxyethyl group, 3-hydroxypropyl group and 4-hydroxybutyl group.

The "$C_{1-6}$ alkoxy group" is a straight chain or branched chain alkoxy group having 1-6, preferably 1 to 4, carbon atoms, such as methoxy group, ethoxy group, propoxy group, isopropoxy group, butoxy group, tert-butoxy group, pentyloxy group, tert-pentyloxy group or hexyloxy group and the like, with preference given to $C_{1-4}$ alkoxy group selected from methoxy group, ethoxy group, propoxy group, isopropoxy group, butoxy group and tert-butoxy group.

The "halo $C_{1-6}$ alkoxy group" is a haloalkoxy group wherein the aforementioned "$C_{1-6}$ alkoxy group" is substituted by one or more halogen atoms, and the position of substitution is not particularly limited as long as it is chemically acceptable. As the "halo $C_{1-6}$ alkoxy group", for example, fluoromethoxy group, difluoromethoxy group, trifluoromethoxy group, chloromethoxy group, dichloromethoxy group, trichloromethoxy group, bromomethoxy group, dibromomethoxy group, tribromomethoxy group, iodomethoxy group, diiodomethoxy group, triiodomethoxy group, 2-fluoroethoxy group, 2,2-difluoroethoxy group, 2,2,2-trifluoroethoxy group, 2-chloroethoxy group, 2,2-dichloroethoxy group, 2,2,2-trichloroethoxy group, 2-bromoethoxy group, 2,2-dibromoethoxy group, 2,2,2-tribromoethoxy group, 3-chloropropoxy group or 4-chlorobutoxy group and the like can be mentioned. Preferred is halo $C_{1-2}$ alkoxy group such as trifluoromethoxy group and 2,2,2-trichloroethoxy group, and particularly preferred is trifluoromethoxy group.

The "$C_{1-6}$ alkoxy-carbonyl group" is alkoxy-carbonyl group wherein the $C_{1-6}$ alkoxy moiety is the aforementioned "$C_{1-6}$ alkoxy group". For example, methoxycarbonyl group, ethoxycarbonyl group, propoxycarbonyl group, isopropoxycarbonyl group, butoxycarbonyl group, isobutoxycarbonyl group, tert-butoxycarbonyl group, pentyloxycarbonyl group, hexyloxycarbonyl group and the like can be mentioned. Preferred are methoxycarbonyl group, ethoxycarbonyl group, propoxycarbonyl group, isopropoxycarbonyl group, butoxycarbonyl group, isobutoxycarbonyl group and tert-butoxycarbonyl group.

The "$C_{1-7}$ acyl group" is alkanoyl group, alkenoyl group or aroyl group having 1 to 7 carbon atoms, such as formyl group, acetyl group, propionyl group, butyryl group, pivaloyl group, ethenoyl group, propenoyl group, butenoyl group, benzoyl group and the like, with preference given to formyl group, acetyl group, pivaloyl group and benzoyl group. The acyl group may be substituted by carboxyl group. Examples thereof include carboxyacetyl group, 3-carboxypropionyl group, 4-carboxybutyryl group, 3-carboxypropenoyl group and the like.

The "$C_{3-6}$ cycloalkyl group" is a cyclic alkyl group having 3 to 6 carbon atoms, such as cyclopropyl group, cyclobutyl group, cyclopentyl group, cyclohexyl group, cycloheptyl group and the like, preferably $C_{3-5}$ cycloalkyl group such as cyclopropyl group, cyclobutyl group, cyclopentyl group and the like, more preferably cyclopropyl group and cyclobutyl group, particularly preferably cyclopropyl group.

The "$C_{2-4}$ alkenyl group" is an alkenyl group having 2 to 4 carbon atoms, such as vinyl group, 1-propenyl group, 2-methyl-1-propenyl group, allyl group, 1-butenyl group, 2-butenyl group, 3-butenyl group and the like can be mentioned, preferably vinyl group.

The "$C_{1-6}$ alkylene group" is a linear or branched chain alkylene group having 1 to 6, preferably 1 to 4, carbon atoms, and, for example, methylene group, ethylene group, propylene group, butylene group, pentylene group, hexylene group

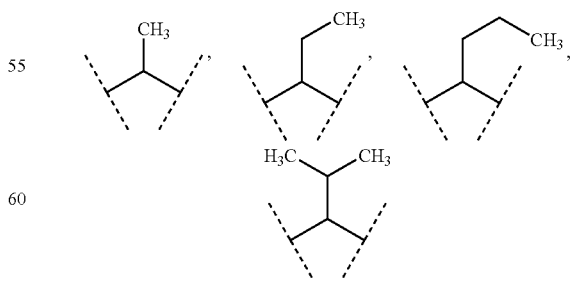

and the like can be mentioned. Preferred are methylene group, propylene group and butylenes group.

As the "$C_{1-6}$ alkylene group" contained in $R^4$,

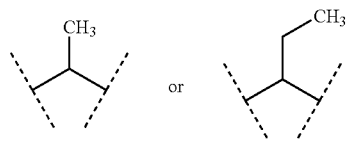

is preferable, and

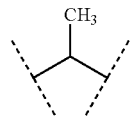

is particularly preferable.

The "$C_{2-4}$ alkenylene group" is an alkenylene group having 2 to 4, preferably 2 or 3, carbon atoms, such as vinylene group, 1-propenylene group, 2-propenylene group, 1-butenylene group, 2-butenylene group, 3-butenylene group and the like, preferably vinylene group, 1-propenylene or 2-propenylene group, particularly vinylene group.

The "$C_{2-4}$ alkynylene group" is an alkynylene group having 2 to 4, preferably 2 or 3, carbon atoms. For example, ethynylene, 1-propynylene, 2-propynylene, 1-butynylene, 2-butynylene, 3-butynylene, 1-pentynylene, 2-pentynylene, 3-pentynylene, 4-pentynylene, 1-hexynylene, 2-hexynylene, 3-hexynylene, 4-hexynylene or 5-hexynylene and the like can be mentioned. Preferred are ethynylene, 1-propynylene and 2-propynylene.

The "$C_{1-7}$ acylamino-$C_{1-6}$ alkyl group" is a group wherein the aforementioned "$C_{1-6}$ alkyl group" is substituted by "$C_{1-7}$ acylamino group". Examples thereof include alkanoylamino-$C_{1-6}$ alkyl group such as formylaminomethyl group, acetylaminomethyl group, propionylaminomethyl group, butyrylaminomethyl group, pivaloylaminomethyl group, formylaminoethyl group, acetylaminoethyl group, propionylaminoethyl group, butyrylaminoethyl group, pivaloylaminoethyl group, formylaminopropyl group, acetylaminopropyl group, propionylaminopropyl group, butyrylaminopropyl group, pivaloylaminopropyl group, formylaminobutyl group, acetylaminobutyl group, propionylaminobutyl group, butyrylaminobutyl group, pivaloylaminobutyl group, formylaminopentyl group, acetylaminopentyl group, propionylaminopentyl group, butyrylaminopentyl group, pivaloylaminopentyl group, formylaminohexyl group, acetylaminohexyl group, propionylaminohexyl group, butyrylaminohexyl group, pivaloylaminohexyl group and the like, and aroylamino-$C_{1-6}$ alkyl group such as benzoylaminomethyl group, benzoylaminoethyl group, benzoylaminopropyl group, benzoylaminobutyl group, benzoylaminopentyl group, benzoylaminohexyl group and the like, with preference given to acetylaminomethyl group and acetylaminoethyl group.

The "carboxy-$C_{1-6}$ alkyl group" is a group wherein the aforementioned "$C_{1-6}$ alkyl group" is substituted by carboxyl group. For example, carboxymethyl group, carboxyethyl group, carboxypropyl group, carboxybutyl group, carboxypentyl group, carboxyhexyl group and the like can be mentioned. Of these, carboxymethyl group is preferable.

The "$C_{1-6}$ alkoxy-carbonyl-$C_{1-6}$ alkyl group" is a group wherein the aforementioned "$C_{1-6}$ alkyl group" is substituted by the aforementioned "$C_{1-6}$ alkoxy-carbonyl group". For example, methoxycarbonylmethyl group, ethoxycarbonylmethyl group, propoxycarbonylmethyl group, butoxycarbonylmethyl group, pentyloxycarbonylmethyl group, hexyloxycarbonylmethyl group and the like can be mentioned. Preferred are methoxycarbonylmethyl group, ethoxycarbonylmethyl group, methoxycarbonylethyl group, ethoxycarbonylethyl group and the like, and particularly preferred is ethoxycarbonylmethyl group.

The "carbamoyl-$C_{1-6}$ alkyl group" is a group wherein the aforementioned "$C_{1-6}$ alkyl group" is substituted by carbamoyl group. For example, carbamoylmethyl group, carbamoylethyl group, carbamoylpropyl group, carbamoylbutyl group, carbamoylpentyl group, carbamoylhexyl group and the like can be mentioned, with preference given to carbamoylmethyl group.

As the "$C_{1-6}$ alkylsulfonyl-carbamoyl group", methylsulfonylcarbamoyl group, ethylsulfonylcarbamoyl group, propylsulfonylcarbamoyl group, butylsulfonylcarbamoyl group, pentylsulfonylcarbamoyl group, hexylsulfonylcarbamoyl group and the like can be mentioned, with preference given to methylsulfonylcarbamoyl group.

The "phosphoric acid residue optionally esterified by $C_{1-6}$ alkyl group" is a group wherein phosphoric acid group ($-PO_3H_2$) is optionally substituted by the aforementioned "$C_{1-6}$ alkyl group". For example, phosphono group, hydroxymethoxyphosphoryl group, ethoxyhydroxyphosphoryl group, hydroxypropoxyphosphoryl group, butoxy hydroxyphosphoryl group, hydroxypentyloxyphosphoryl group, hexyloxyhydroxyphosphoryl group, dimethoxyphosphoryl group, diethoxyphosphoryl group, dipropoxyphosphoryl group, dibutoxyphosphoryl group, ethoxymethoxyphosphoryl group, methoxypropoxyphosphoryl group, butoxy methoxyphosphoryl group and the like can be mentioned. Of these, phosphono group, hydroxymethoxyphosphoryl group and ethoxyhydroxyphosphoryl group are preferable and phosphono group and ethoxyhydroxyphosphoryl group are particularly preferable.

The "5- or 6-membered heterocyclic residue having 1 to 4 hetero atoms selected from the group consisting of nitrogen atom, oxygen atom and sulfur atom" is, for example, an unsaturated 5-membered ring such as thienyl group, dihydrothienyl group, furyl group, dihydrolyl group, pyrrolyl group, pyrrolinyl group, imidazolyl group, imidazolinyl group, pyrazolyl group, pyrazolinyl group, thiazolyl group, thiazolinyl group, isothiazolyl group, isothiazolinyl group, oxazolyl group, oxazolinyl group, isoxazolyl group, isoxazolinyl group, triazolyl group, triazolinyl group, thiadiazolyl group, thiadiazolinyl group, oxadiazolyl group, oxadiazolinyl group, dithiazolyl group, dithiazolinyl group, dioxazolyl group, dioxazolinyl group, tetrazolyl group and the like; an unsaturated 6-membered ring such as pyridinyl group, pyrazinyl group, pyrimidinyl group, pyranyl group and the like; a saturated 5-membered ring such as pyrrolidinyl group, oxoranyl group, dioxoranyl group, thioranyl group, dithioranyl group, pyrazolidinyl group, imidazolidinyl group, oxazolidinyl group, thiazolidinyl group, isoxazolidinyl group, isothiazolidinyl group and the like; piperidinyl group, oxanyl group, thianyl group, piperazinyl group, morpholinyl group, thiomorpholinyl group, dioxanyl group, dithianyl group and the like can be mentioned, with preference given to oxadiazolyl group, thiadiazolyl group and tetrazolyl group. The heterocyclic residue is optionally substituted by oxo group.

As the "salt" of the compound of the present invention, there can be mentioned, but not limited to, inorganic acid addition salts such as hydrochloride, hydrobromide, sulfate, phosphate or nitrate and the like; organic acid addition salts such as acetate, propionate, succinate, glycolate, lactate, malate, oxalate, tartrate, citrate, maleate, fumarate, methanesulfonate, benzenesulfonate, p-toluenesulfonate or ascorbate and the like; amino acid addition salts such as aspartate or glutamate and the like; inorganic base salts with sodium, potassium, calcium, magnesium or zinc and the like; organic base salts with methylamine, dimethylamine, ethylamine, diethylamine, triethylamine, triethanolamine, trishydroxymethylaminomethane, dicyclohexylamine, ethylenediamine, guanidine, meglumine, 2-aminoethanol and the like; and base salts with amino acids such as asparagine, glutamine, arginine, histidine, lysin and the like. Preferable salts are hydrochloride, sodium salt, potassium salt and calcium salt, and hydrochloride and sodium salt are particularly preferable.

The compound of the present invention includes solvate. As used herein, a "solvate" of a compound includes the compound of the present invention bonded with solvent molecules such as water, alcohol and the like in a solid state such as crystal, amorphous and the like or in a solution by a comparatively weak bond based on Van der Waals force, static interaction, hydrogen bond, charge transfer bond, coordinate bond and the like. In some cases, solvent may be incorporated into a solid state to form hydrate, alcoholate and the like. Preferable solvate is hydrate.

A "prodrug" of a compound is a derivative of the compound of the present invention, which has a chemically or metabolically decomposable group, which decomposes by hydrolysis or solvolysis, or under physiological conditions to show pharmaceutical activity. A substituent represented by $R^A$ and a substituent represented by $R^B$ in the formula (1) or (1') of the present invention are substituents directed to a prodrug, and —$COR^A$ and/or —$OR^B$ are/is substituent(s) converted to —$CO_2H$ and/or —OH in the living organism.

The compound represented by the formula (1) or (1') of the present invention has various isomers, such as optical isomers, stereoisomers, geometric isomers, tautomers and the like. The present invention encompasses all these isomers and mixtures thereof.

The form of the compound of the present invention to be used as a pharmaceutical product is a compound itself (free form), a salt of the compound, a solvate of the compound or a prodrug of the compound. Preferable form is a free form, a salt of the compound or a solvate of the compound, particularly preferably a salt of the compound.

A therapeutic drug for osteoporosis, which contains the compound of the present invention as an active ingredient, can be used along with a different therapeutic drug for osteoporosis. The different therapeutic drug for osteoporosis includes, for example, a calcium agent (calcium lactate, calcium gluconate, calcium aspartate, calcium chloride, calcium hydrogen phosphate etc.), a vitamin D preparation (Alfacalcidol, Calcitriol, Maxacalcitol, Falecalcitriol etc.), a vitamin K preparation (Menatetrenone etc.), a female hormone preparation (Estradiol, Estriol etc.), an estrogen antagonist preparation (Raloxifen etc.), an anabolic steroid preparation, a parathyroid hormone preparation (Teriparatide, PTH(1-84) etc.), a calcitonin preparation (Elcatonin, Calcitonin salmon etc.), a bisphosphonate preparation (Alendronate sodium hydrate, Sodium risedronate hydrate, Etidronate disodium, Pamidronate disodium, Incadronate disodium etc.), an ipriflavone preparation (Ipriflavone), other therapeutic drugs for osteoporosis, such as Strontium Ranelate, WNT inhibitor, PPARγ agonist, Osteopontin, Statin preparation, RANK/RANKL inhibitor, Src inhibitor, Pyk2 inhibitor, Osteoprotegerin and the like. A therapeutic drug for osteoporosis containing the compound of the present invention and a different therapeutic drug for osteoporosis can be administered to osteoporosis patients in an effective amount.

The production methods of the compound of the formula (1) or (1') of the present invention are concretely explained in the following. It is needless to say that the present invention is not limited to these production methods. For construction of the compound of the present invention, the construction may start from a moiety easily synthesized. When a reactive functional group is contained in a step, appropriate protection and deprotection may be performed, and to facilitate the reaction, any reagent other than those exemplified may be appropriately used.

The all compound obtained in each Step may be isolated and purified by conventional methods. In some cases, the compound may be used in the next step without isolation and purification.

A compound wherein $R^6$ is a hydrogen atom is explained in the following.

<Production Method 1 of Compound Wherein Ring A is Biphenyl Substituted by Heterocyclic Reside>

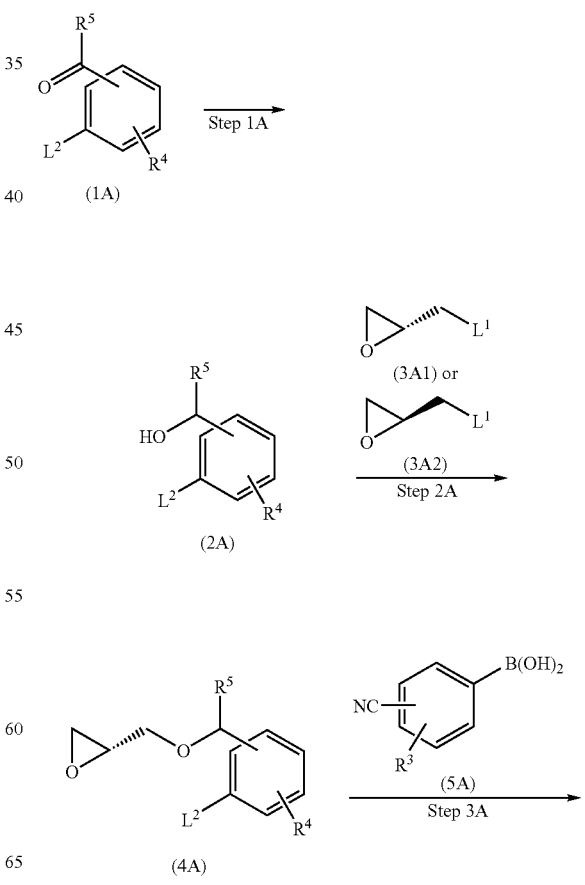

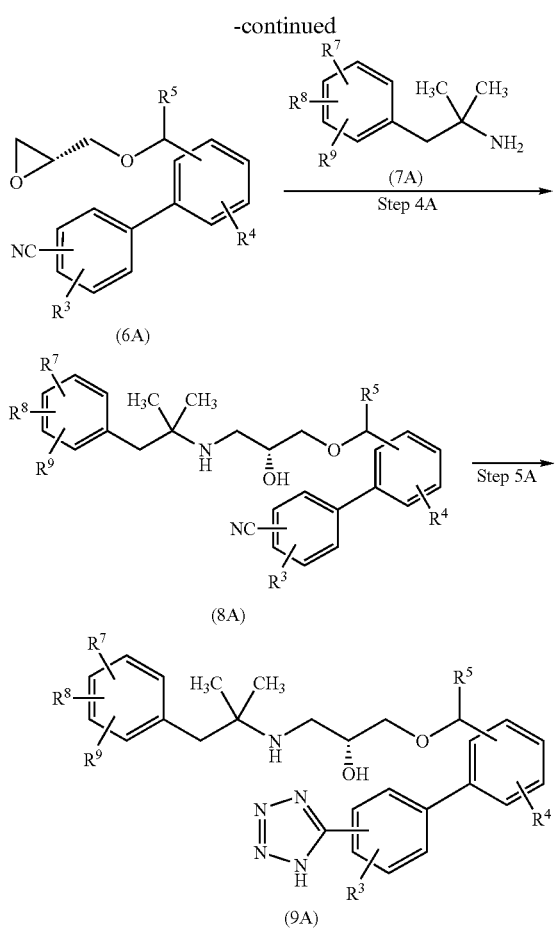

(6A)

(8A)

(9A)

wherein $L^2$ is a halogen atom (as defined above), $L^1$ is a leaving group, such as a halogen atom (as defined above) or a sulfonyloxy group such as a 3-nitrobenzenesulfonyloxy group, a p-toluenesulfonyloxy group, a benzenesulfonyloxy group, a p-bromobenzenesulfonyloxy group, a methanesulfonyloxy group or a trifluoromethanesulfonyloxy group and the like, and other symbols are as defined above.

Step 1A

In isopropanol, tetrahydrofuran, toluene, methanol, ethanol and the like or a mixed solvent thereof, Compound (1A) is reduced with a reducing agent such as lithium aluminum hydride, sodium borohydride, lithium borohydride and the like at −10° C. to room temperature to give compound (2A). By subjecting compound (1A) to reduction reaction using an asymmetric reducing agent such as (+)-B-chlorodiisopinocampheylborane, (S)-5,5-diphenyl-2-methyl-3,4-propano-1,3,2-oxazaborolidine-borane-dimethyl sulfide complex salt and the like, or asymmetric hydrogenation reaction using a ruthenium complex such as dichloro[(S)-2,2'-bis(diphenylphosphino)-1,1'-binaphthyl][(S)-1,1'-bis(p-methoxyphenyl)-2-isopropylethane-1,2-diamine]ruthenium (II) and the like and potassium-tert-butoxide, a stereoselective reaction proceeds to give an R form of compound (2A).

Step 2A

The compound (2A) obtained in step 1A is reacted with compound (3A1) or compound (3A2) in N,N-dimethylformamide, dimethyl sulfoxide, tetrahydrofuran, water etc. or a mixed solvent thereof, in the presence of a base such as sodium hydride, sodium hydroxide, potassium hydroxide, sodium carbonate, potassium carbonate, sodium hydrogen carbonate, potassium hydrogen carbonate, triethylamine, N,N-diisopropylethylamine, N-methylmorpholine, pyridine, 4-dimethylaminopyridine etc. at 0° C. to room temperature to give compound (4A). In this case, alkyl ammonium hydrogen sulfate such as tetrabutyl ammonium hydrogen sulfate and the like may be added.

A stereoselective reaction can be carried out by selecting a reagent and a leaving group to be used.

For example, compound (2A) is reacted with (R)-glycidyl nosylate in N,N-dimethylformamide in the presence of sodium hydride to give compound (IVA).

Step 3A

The compound (4A) obtained in step 2A is reacted with compound (5A) in toluene, ethanol, benzene, acetone, 1,4-dioxane, tetrahydrofuran, acetonitrile, N,N-dimethylformamide, 1,2-dimethoxyethane, dimethyl sulfoxide, water and the like or a mixed solvent thereof, using a palladium catalyst such as [bis(diphenylphosphino)ferrocene]dichloropalladium(II), tetrakis(triphenylphosphine)palladium(0) and the like and a base such as sodium carbonate, tripotassium phosphate ($K_3PO_4$), potassium carbonate, sodium hydrogen carbonate, potassium hydrogen carbonate and the like, whereby compound (6A) is obtained (by Suzuki coupling).

Step 4A

The compound (6A) obtained in Step 3A is reacted with compound (7A) in methanol, ethanol, n-propanol, isopropanol, tetrahydrofuran, 1,4-dioxane, acetonitrile, toluene and the like or a mixed solvent thereof at room temperature to reflux temperature to give compound (8A). In this case, alkali perchlorate such as lithium perchlorate and the like is preferably added.

Step 5A

Compound (8A) obtained in Step 4A is reacted with ammonium chloride and sodium azide in N,N-dimethylformamide, toluene, xylene, water and the like or a mixed solvent thereof at room temperature to refluxing temperature to give compound (9A).

<Production Method 2 of Compound Wherein Ring A is Biphenyl Substituted by Heterocyclic Residue>

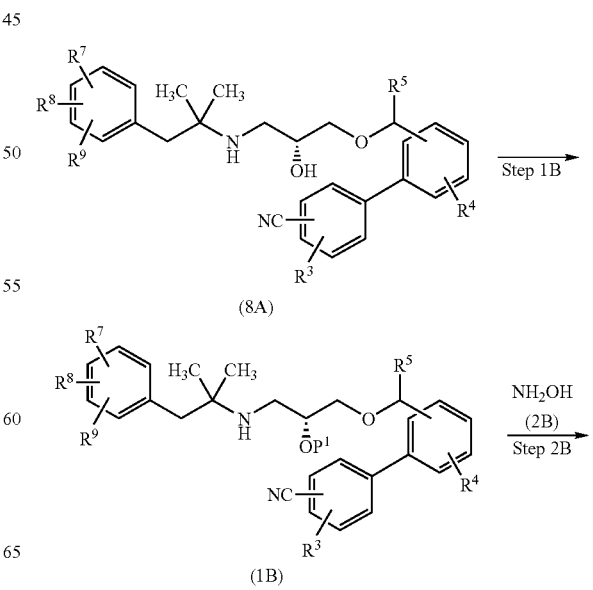

(8A)

(1B)

Step 4B

Compound (5B) is obtained by removing the hydroxyl-protecting group of compound (4B) obtained in Step 3B by a conventional method. For example, when the hydroxyl group of compound (5B) is protected with t-butyldimethylsilyl group (TBS), compound (5B) is obtained by reacting compound (4B) with tetrabutylammonium fluoride (TBAF) in tetrahydrofuran, water and the like or a mixed solvent thereof. When protected with other protecting group, a method generally employed for removing the protecting group only needs to be used.

<Production Method 3 of Compound Wherein Ring A is Biphenyl Substituted by Heterocyclic Residue>

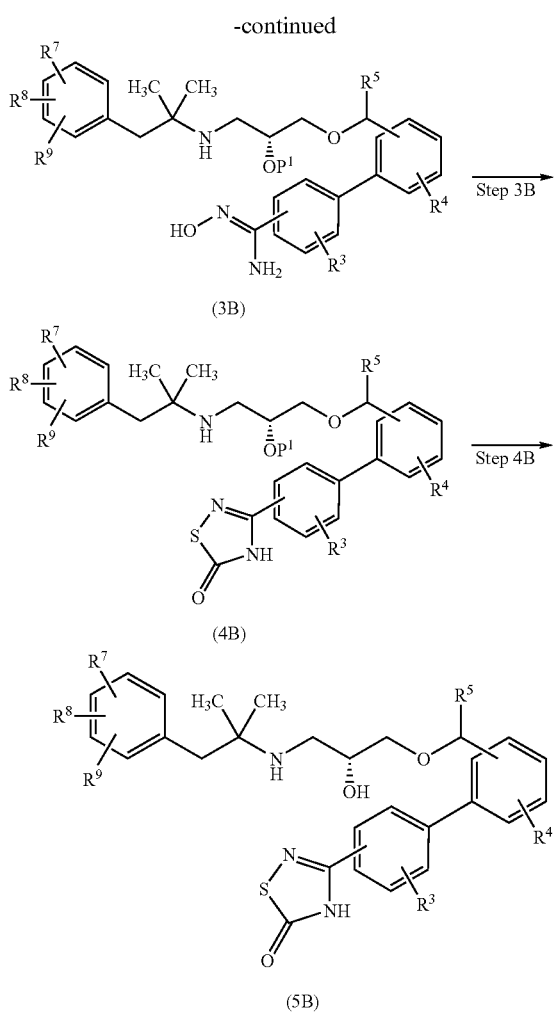

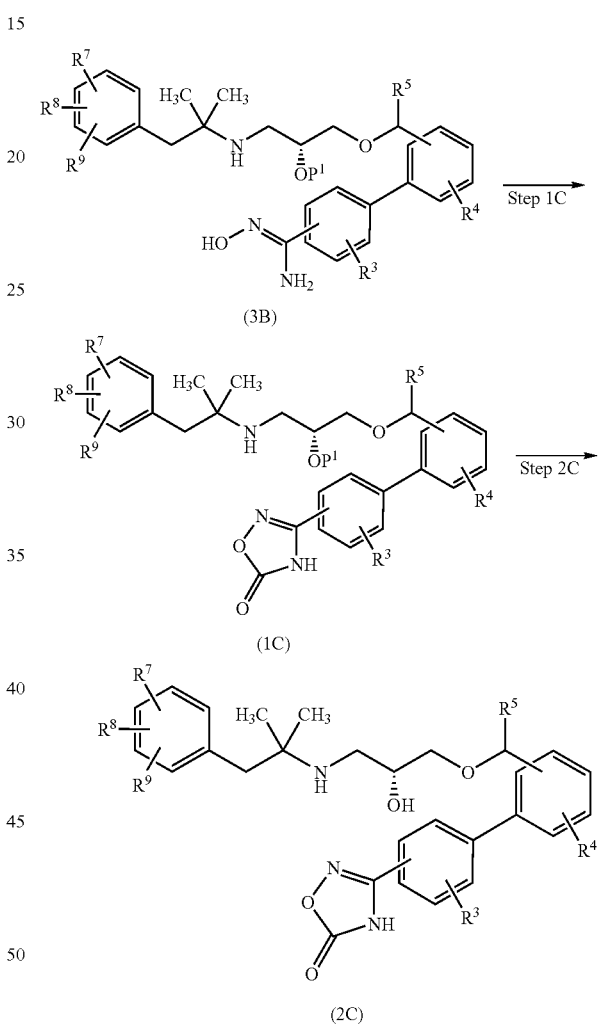

wherein $P^1$ is a hydroxyl-protecting group, and other symbols are defined above.

Step 1B

Compound (1B) is obtained by protecting hydroxyl group of compound (8A) by a conventional method. For example, when the hydroxyl group is protected by tert-butyldimethylsilyl group (TBS), compound (1B) is obtained by reacting compound (8A) with tert-butyldimethylsilyl chloride in a solvent such as N,N-dimethylformamide and the like in the presence of a base such as imidazole and the like. When a compound protected with other protecting group is desired, a method generally employed for introducing the protecting group only needs to be used.

Step 2B

Compound (1B) obtained in Step 1B and compound (2B) are reacted in dimethylsulfoxide, ethanol, water and the like or a mixed solvent thereof at room temperature to refluxing temperature to give compound (3B).

Step 3B

Compound (3B) obtained in Step 2B is reacted with 1,1'-thiocarbonyldiimidazole(TCDI) in tetrahydrofuran, diethyl ether and the like or a mixed solvent thereof, and treated with boron trifluoride ether complex salt in tetrahydrofuran, diethyl ether and the like or a mixed solvent thereof to give compound (4B).

wherein each symbol is as defined above.

Step 1C

Compound (3B) obtained in Step 2B is reacted with alkyl chlorocarbonate such as ethyl chlorocarbonate and the like in a solvent such as chloroform, methylene chloride and the like in the presence of a base such as pyridine, triethylamine, diisopropylethylamine, and the like, and then cyclized in a solvent such as xylene, toluene and the like at room temperature to refluxing temperature to give compound (1C).

Step 2C

Compound (2C) is obtained by subjecting compound (1C) obtained in Step 1C to a reaction similar to Step 4B.

When a compound wherein ring A is biphenyl substituted by a hetero ring other than those exemplified here is desired, a method generally employed for constructing a desired hetero ring is used to give a compound wherein ring A is biphenyl substituted by the hetero ring.

<Production Method of Compound Wherein Ring A is Phenyl Substituted by —O—X—CO₂H>

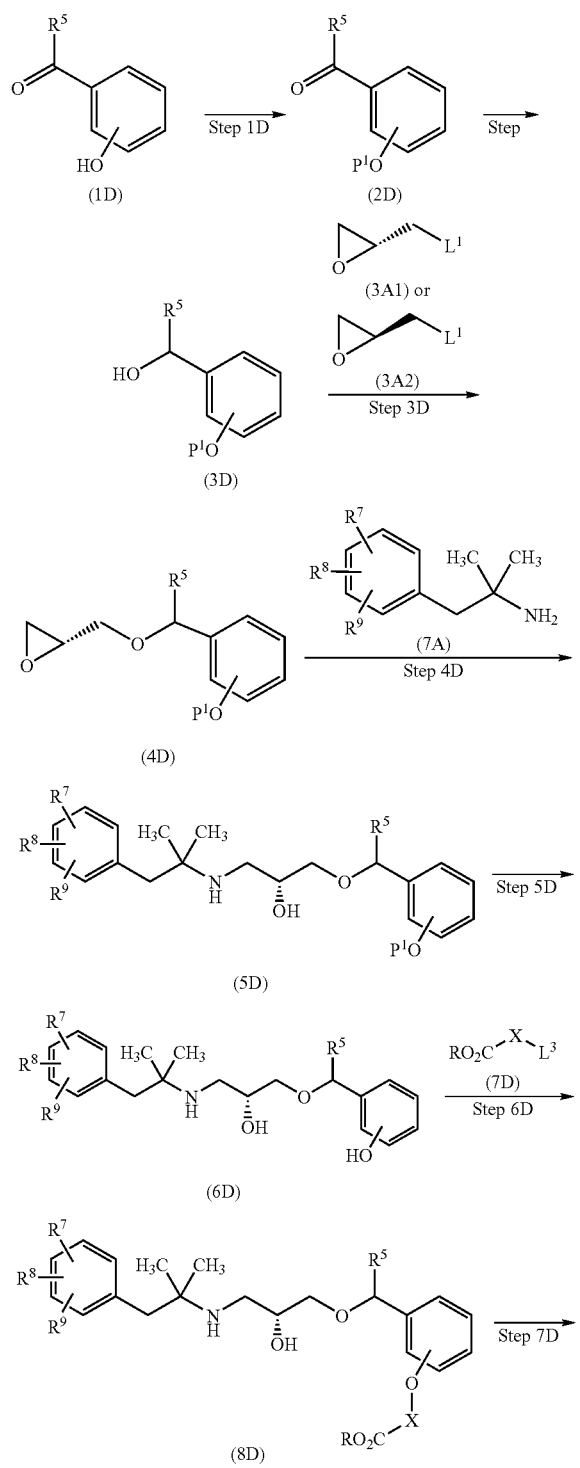

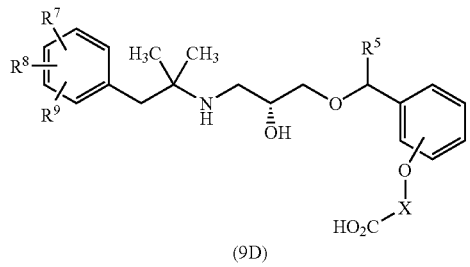

wherein $L^3$ is a halogen atom (as defined above), R is a $C_{1-6}$ alkyl group (as defined above), and other symbols are defined above.

Step 1D

Compound (2D) is obtained by protecting hydroxyl group of compound (1D) by a conventional method. For example, when hydroxyl group is to be protected by 2-(trimethylsilyl)ethoxymethyl (SEM) group, compound (2D) is obtained by reacting with 2-(trimethylsilyl)ethoxymethyl halide (e.g., 2-(trimethylsilyl)ethoxymethyl chloride (SEMCl)) in a solvent such as chloroform, methylene chloride and the like, in the presence of a base such as diisopropylethylamine and the like. When protection with other protecting group is desired, a method generally employed for introducing the protecting group only needs to be used.

Step 2D

Compound (3D) is obtained by subjecting compound (2D) obtained in Step 1D to a reaction similar to Step 1A.

Step 3D

Compound (4D) is obtained by subjecting compound (3D) obtained in Step 2D to a reaction similar to Step 2A together with compound (3A1) or compound (3A2).

Step 4D

Compound (5D) is obtained by subjecting compound (4D) obtained in Step 3D to a reaction similar to Step 4A together with compound (7A).

Step 5D

Compound (6D) is obtained by removing the hydroxyl-protecting group of compound (5D) obtained in Step 4D by a conventional method. For example, when the hydroxyl group of compound (5D) is protected by 2-(trimethylsilyl)ethoxymethyl group, compound (6D) is obtained by deprotection in 1,3-dimethyl-3,4,5,6-tetrahydro-2(1H)-pyrimidinone in the presence of tetrabutylammonium halide (e.g., tetrabutylammonium fluoride and the like) and MS4A. When the hydroxyl group of compound (5D) protected with other protecting group, a method generally employed for removing the protecting group only needs to be used.

Step 6D

Compound (6D) obtained in Step 5D is reacted with compound (7D) in N,N-dimethylformamide, tetrahydrofuran, diethyl ether, dimethyl sulfoxide, acetone, acetonitrile and the like or a mixed solvent thereof, in the presence of a base such as sodium hydride, potassium carbonate, sodium carbonate and the like to give compound (8D).

Step 7D

Compound (8D) obtained in Step 6D is hydrolyzed by a conventional method to give compound (9D). For example, compound (8D) is hydrolyzed in tetrahydrofuran-methanol-water in the presence of sodium hydroxide to give compound (9D).

<Production Method of Compound Wherein Ring A is Phenyl Substituted by —$C_{2-4}$ alkynylene-$CO_2H$> and the like, a catalyst such as copper iodide and the like, and a base such as potassium carbonate, triethylamine and the like to give compound (2F).

Step 2F

By subjecting compound (2F) obtained in Step 1F and compound (7A) to a reaction similar to Step 4A, compound (3F) is obtained.

Step 3F

By subjecting compound (3F) obtained in Step 2F to a reaction similar to Step 7D, compound (4F) is obtained.

<Production Method of Compound Wherein Ring A is Biphenyl Substituted by $C_{1-6}$ alkylsulfonyl-carbamoyl Group>

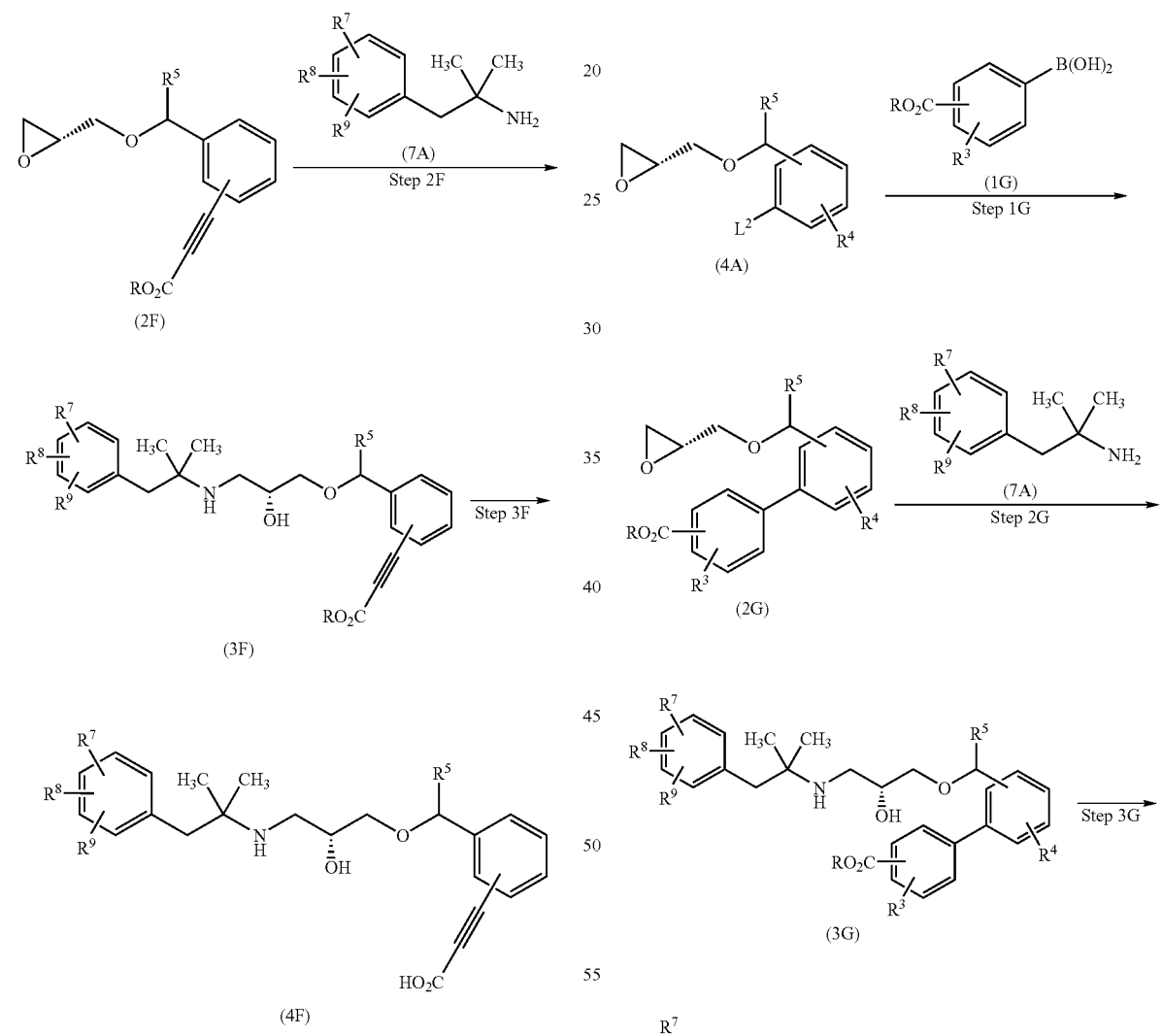

wherein each symbol is as defined above.

Step 1F

Compound (4A') obtained in the same manner as in Step 2A is reacted with compound (1F) in a solvent such as tetrahydrofuran, diethyl ether, N,N-dimethylformamide, dimethyl sulfoxide, acetonitrile and the like, in the presence of a palladium catalyst such as dichlorobis(triphenylphosphine)palladium, tetrakis(triphenylphosphine)palladium(0)

-continued

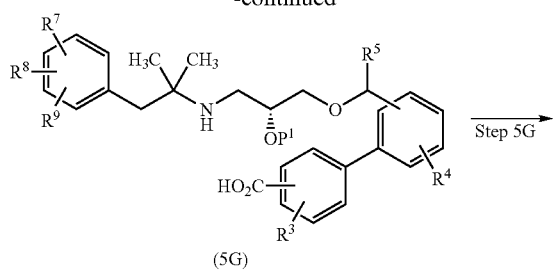

(5G)

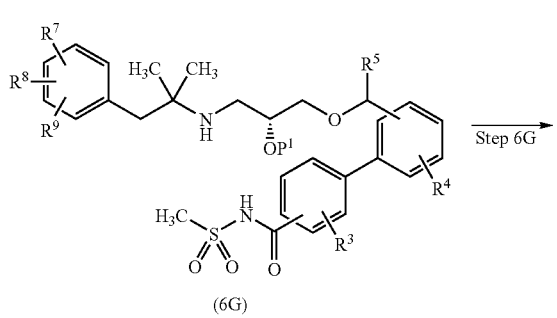

(6G)

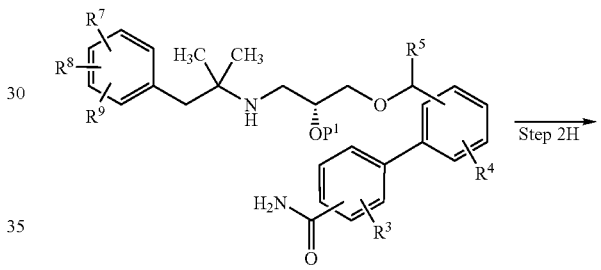

(7G)

wherein each symbol is as defined above.

Step 1G

By subjecting compound (4A) and compound (1G) to a reaction similar to Step 3A, compound (2G) is obtained.

Step 2G

By subjecting compound (2G) obtained in Step 1G and compound (7A) to a reaction similar to Step 4A to give compound (3G).

Step 3G

By subjecting compound (3G) obtained in Step 2G to a reaction similar to Step 1B, compound (4G) is obtained.

Step 4G

By subjecting compound (4G) obtained in Step 3G to a reaction similar to Step 7D, compound (5G) is obtained.

Step 5G

By reacting compound (5G) obtained in Step 4G with methanesulfonamide in a solvent such as N,N-dimethylformamide, methylene chloride and the like, in the presence of a base such as 4-(dimethylamino)pyridine and the like and a condensing agent such as 1-ethyl-3-(3-dimethylaminopropyl)carbodiimide and the like, compound (6G) can be obtained.

Step 6G

By subjecting compound (6G) obtained in Step 5G to a reaction similar to Step 4B, compound (7G) is obtained.

<Production Method of Compound Wherein Ring A is Biphenyl Substituted by Caramoyl Group>

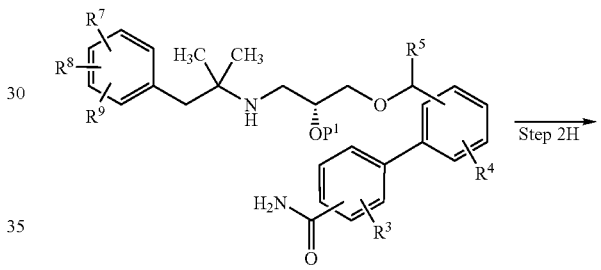

(5G)

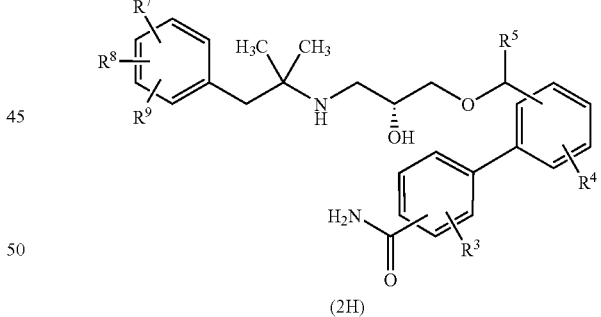

(1H)

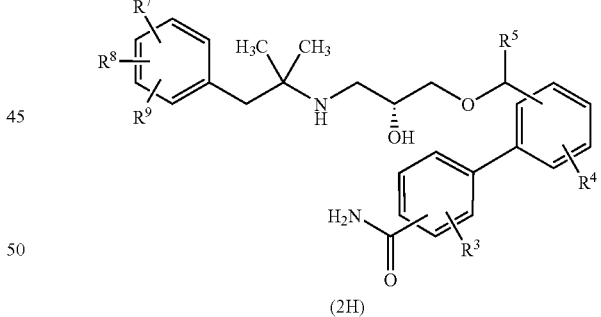

(2H)

wherein each symbol is as defined above.

Step 1H

By reacting compound (5G) obtained in Step 4G with ammonium chloride or aqueous ammonia in N,N-dimethylformamide in the presence of a condensing agent such as 1-ethyl-3-(3-dimethylaminopropyl)carbodiimide and the like, an additive such as 1-hydroxybenzotriazole and the like and triethylamine, compound (1H) is obtained.

Step 2H

By subjecting compound (1H) obtained in Step 1 to a reaction similar to Step 4B, compound (2H) is obtained.

<Production Method of Compound Wherein Ring A is Biphenyl Substituted by Hydroxycarbamoyl Group>

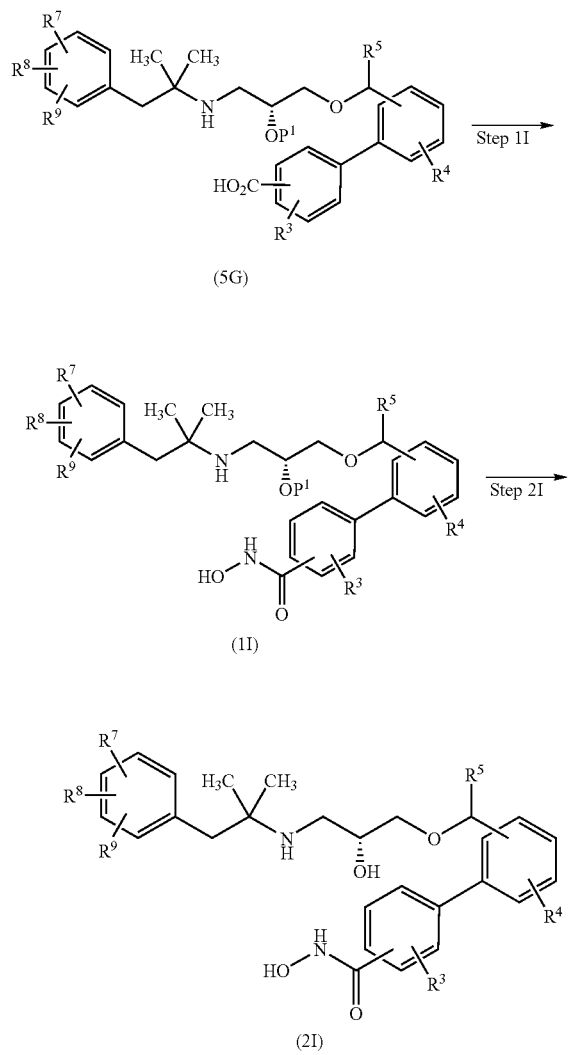

wherein each symbol is as defined above.

Step 1I

Compound (5G) obtained in Step 4G is reacted with O-(trimethylsilyl)hydroxylamine in N,N-dimethylformamide, tetrahydrofuran, diethyl ether, dimethyl sulfoxide, acetone, acetonitrile and the like or a mixed solvent thereof, in the presence of a condensing agent such as dicyclohexylcarbodiimide, 1-ethyl-3-(3-dimethylaminopropyl)carbodiimide, diisopropylcarbodiimide, diphenylphosphoryl azide, 2-ethoxy-1-ethoxycarbonyl-1,2-dihydroquinoline (EEDQ) and the like and an additive such as 1-hydroxybenzotriazole, 4-dimethylaminopyridine and the like to give compound (1I).

Step 2I

By subjecting compound (1I) obtained in Step 1I to a reaction similar to Step 4B, compound (2I) is obtained.

<Production Method of Compound Wherein Ring A is Phenyl Group Substituted by Carboxythienyl Group>

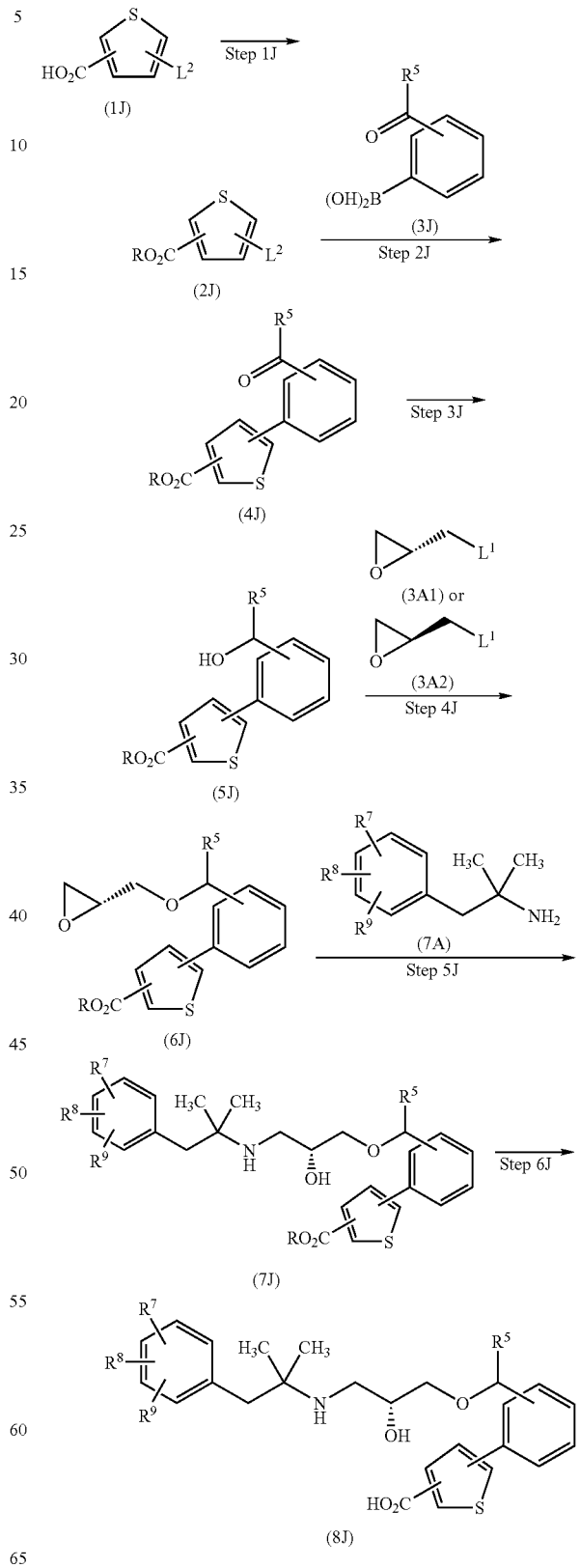

wherein each symbol is as defined above.

Step 1J

Compound (2J) is obtained by esterifying carboxyl group of compound (1J) by a conventional method. For example, the compound (1J) is reacted with alcohol such as methanol, ethanol, propanol and the like in a solvent such as N,N-dimethylformamide, methylene chloride and the like, in the presence of a base such as 4-(dimethylamino)pyridine and the like and a condensing agent such as 1-ethyl-3-(3-dimethylaminopropyl)carbodiimide and the like, to give compound (2J). In addition, by reacting compound (1J) with alcohol such as methanol, ethanol, propanol and the like in the presence of an acid catalyst such as sulfuric acid and the like to give compound (2J).

Step 2J

By subjecting compound (2J) obtained in Step 1J and compound (3J) to a reaction similar to Step 3A, compound (4J) is obtained.

Step 3J

By subjecting compound (4J) obtained in Step 2J to a reaction similar to Step 1A, compound (5J) is obtained.

Step 4J

By subjecting compound (5J) obtained in Step 3J and compound (3A1) or compound (3A2) to a reaction similar to Step 2A, compound (6J) is obtained.

Step 5J

By subjecting compound (6J) obtained in Step 4J and compound (7A) to a reaction similar to Step 4A, compound (7J) is obtained.

Step 6J

By subjecting compound (7J) obtained in Step 5J to a reaction similar to Step 7D, compound (8J) is obtained.

<Production Method of Compound Wherein Ring A is Nitrobiphenyl Group and Aminobiphenyl Group>

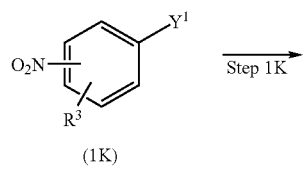

(1K)

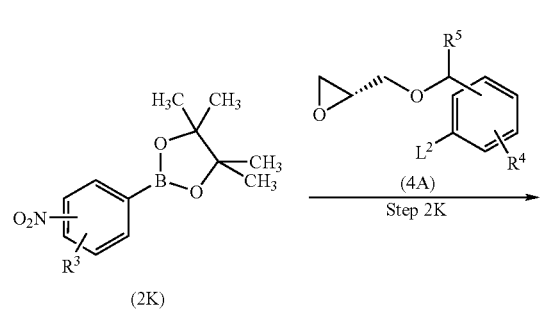

(2K)

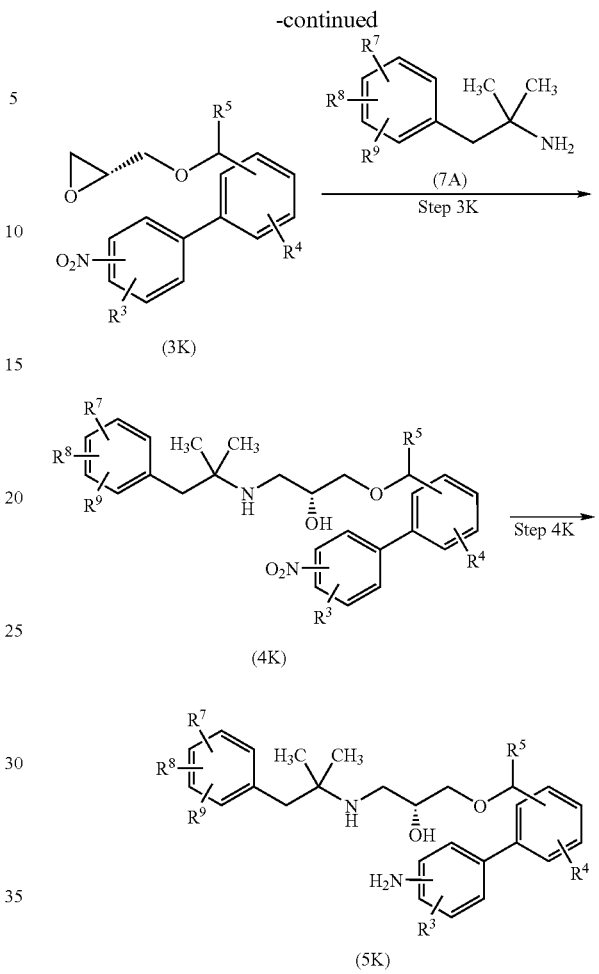

wherein $Y^1$ is a halogen atom (as defined above) or a trifluoromethanesulfonyloxy group, and other symbols are as defined above.

Step 1K

Compound (1K) is reacted with bispinacholato diboron in dimethyl sulfoxide, N,N-dimethylformamide, 1,4-dioxane and the like or a mixed solvent thereof, using [bis(diphenylphosphino)ferrocene]dichloropalladium(II) or a dichloromethane complex thereof and a base such as potassium acetate and the like to give compound (2K).

Step 2K

Compound (2K) obtained in Step 1K is reacted with compound (4A) in toluene, ethanol, benzene, acetone, 1,4-dioxane, tetrahydrofuran, acetonitrile, N,N-dimethylformamide, 1,2-dimethoxyethane, dimethyl sulfoxide, water and the like or a mixed solvent thereof, using a palladium catalyst such as [bis(diphenylphosphino)ferrocene]dichloropalladium(II), tetrakis(triphenylphosphine)palladium(0) and the like, and a base such as sodium carbonate, tri-potassium phosphate ($K_3PO_4$), potassium carbonate, sodium hydrogen carbonate, potassium hydrogen carbonate and the like to give compound (3K).

Step 3K

By subjecting compound (3K) obtained in Step 2K and compound (7A) to a reaction similar to Step 4A, compound (4K) is obtained.

Step 4K compound (4K) obtained in Step 3K is reacted with iron and ammonium chloride in tetrahydrofuran, ethanol, water, methanol and the like or a mixed solvent thereof to give compound (5K).

<Production Method of Compound Wherein Ring A is Biphenyl Group Substituted by $C_{1-7}$ Acylamino-$C_{1-6}$ Alkyl Group>

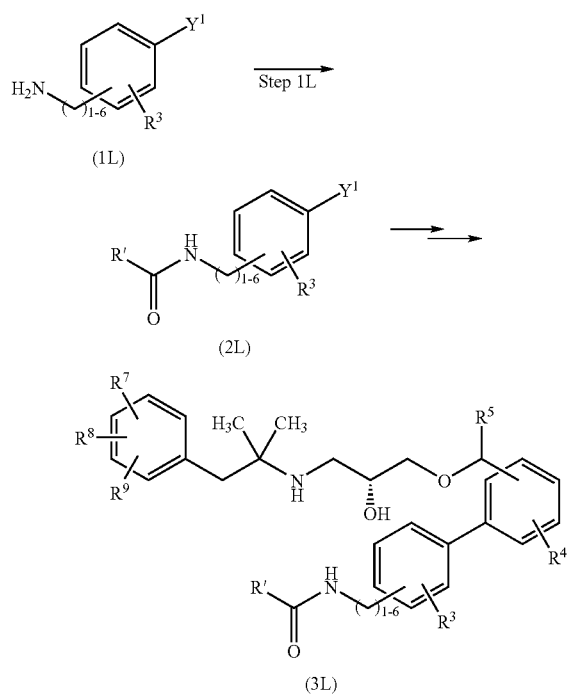

wherein —CO—R' group is a $C_{1-7}$ acyl group (as defined above), and other symbols are defined above.

Step 1L

Compound (1L) is reacted with a compound represented by R'—CO$_2$H or a reactive derivative thereof by a conventional method to give compound (2L). For example, compound (1L) is reacted with acid anhydride of a compound represented by R'—CO$_2$H in chloroform, dichloromethane, tetrahydrofuran, toluene, ethyl acetate and the like or a mixed solvent thereof, in the presence of a base such as pyridine, triethylamine and the like to give compound (2L).

By subjecting compound (2L) obtained in Step 1L to a method similar to Step 1K-Step 3K to give compound (3L).

<Production Method of Compound Wherein Ring A is Biphenyl Group Substituted by Carboxy-$C_{1-6}$ Alkyl Group>

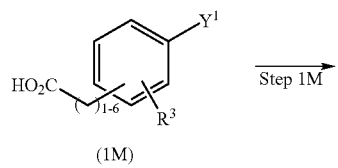

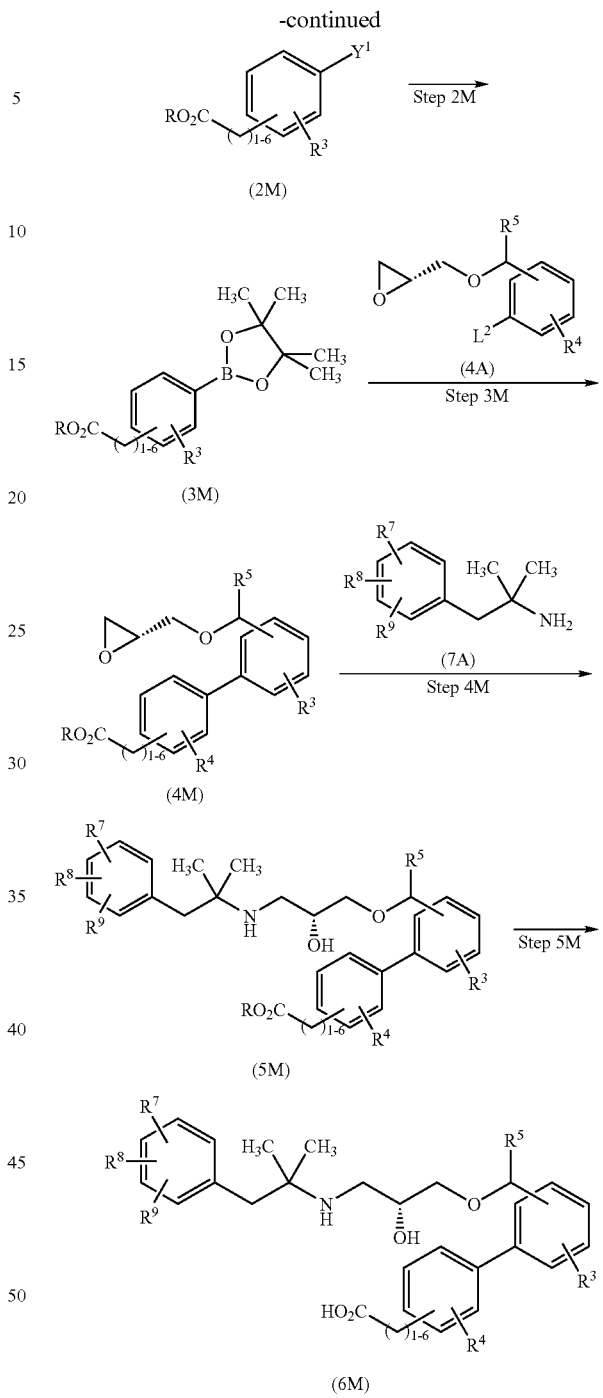

wherein each symbol is as defined above.

Step 1M

By subjecting compound (1M) to a reaction similar to Step 1J to give compound (2M).

Step 2M, Step 3M

Compound (2M) obtained in Step 1M is subjected to a reaction similar to Step 1K to give compound (3M), which is then subjected to a reaction similar to Step 2K to give compound (4M).

Step 4M

By subjecting compound (4M) obtained in Step 3M and compound (7A) to a reaction similar to Step 4A, compound (5M) is obtained.

Step 5M

By subjecting compound (5M) obtained in Step 4M to a reaction similar to Step 7D, compound (6M) is obtained.

<Production Method of Compound Wherein Ring A is Biphenyl Group Substituted by Carbamoyl-$C_{1-6}$ Alkyl Group>

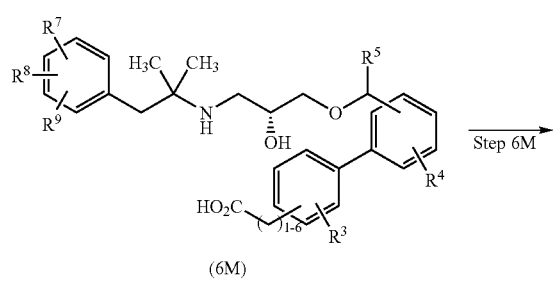

(6M)

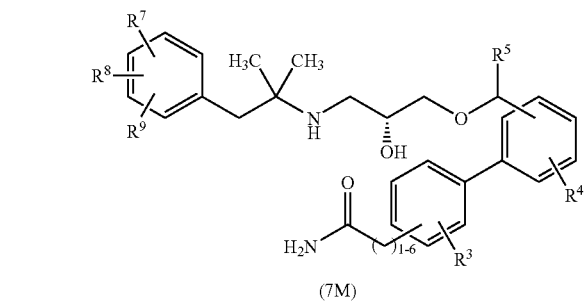

(7M)

wherein each symbol is as defined above.

Step 6M

By subjecting compound (6M) obtained in Step 5M to a reaction similar to Step 1H, compound (7M) is obtained.

<Production Method of Compound Wherein Ring A is Biphenyl Group Substituted by Phosphoric Acid Residue Esterified by $C_{1-6}$ Alkyl Group>

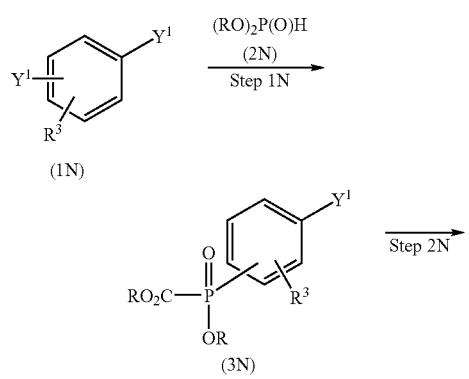

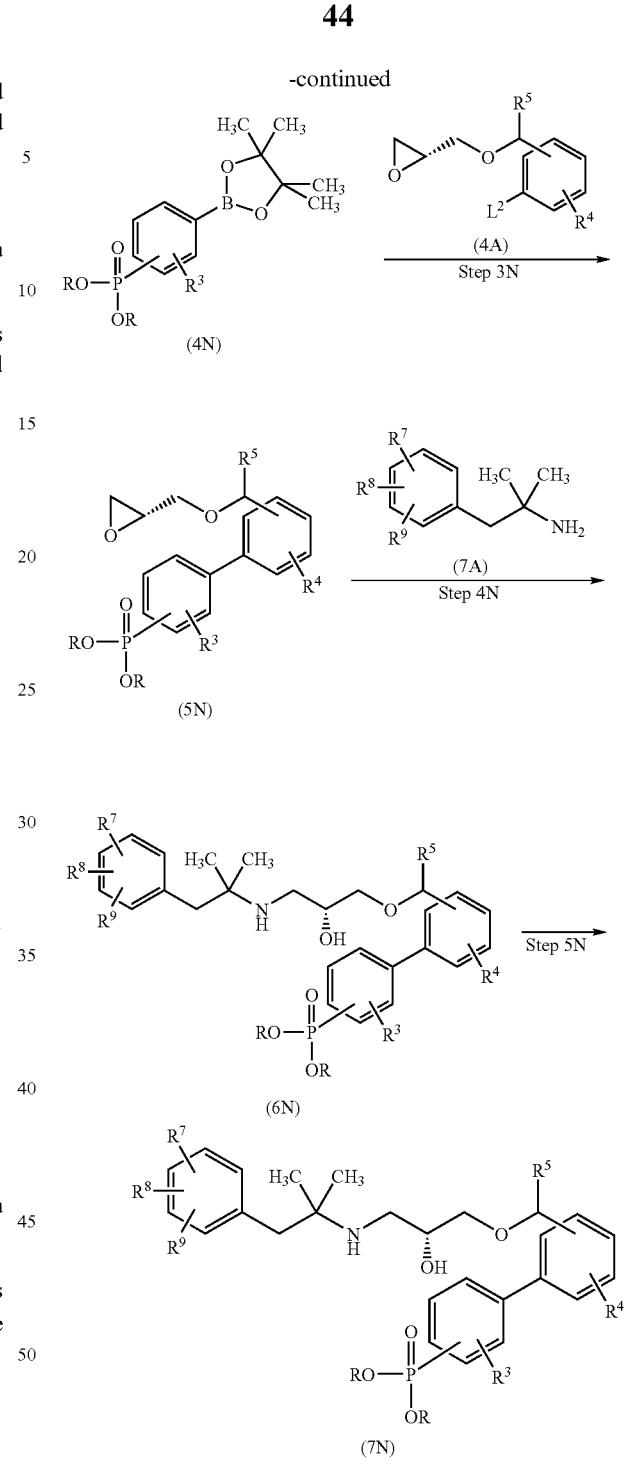

wherein each symbol is as defined above.

Step 1N

Compound (1N) is reacted with compound (2N) in a solvent such as toluene and the like in the presence of a catalyst such as tetrakis(triphenylphosphine)palladium(0) and the like, and a base such as triethylamine and the like at room temperature to refluxing temperature to give compound (3N).

Step 2N

By subjecting compound (3N) obtained in Step 1N to a reaction similar to Step 1K, compound (4N) is obtained.

Step 3N

By subjecting compound (4N) obtained in Step 2N and compound (4A) to a reaction similar to Step 2K, compound (5N) is obtained.

Step 4N

By subjecting compound (5N) obtained in Step 3N and compound (7A) to a reaction similar to Step 4A, compound (6N) is obtained.

Step 5N

Compound (6N) obtained in Step 4N is reacted in dichloromethane in the presence of N,O-bis(trimethylsilyl)trifluoroacetamide (BSTFA) and trimethylsilyl halide (e.g., trimethylsilyl chloride, trimethylsilyl bromide) to give compound (7N). In this case, trimethylsilyl halide is preferably added in about 2.5 equivalents.

<Production Method of Compound Wherein Ring A is Biphenyl Group Substituted by Phosphoric Acid Residue>

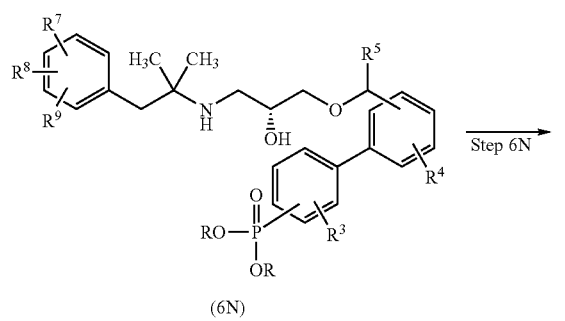

(6N)

(8N)

wherein each symbol is as defined above.

Step 6N

Compound (6N) obtained in Step 4N is subjected to a reaction similar to Step 5N to give compound (8N). In this case, trimethylsilyl halide is preferably added in about 4 equivalents.

Compound (8N) can be converted to a salt by a conventional method. For example, disodium salt of compound (8N) can be obtained by adding sodium hydroxide in water.

<Production Method of Compound Wherein Ring A is Biphenyl Group Substituted by $R^B O—C(=O)O—C_{1-6}$ Alkoxy-carbonyl Group>

(3G)

(1P)

(3P)

wherein $R^D$ is $R^B O—C(=O)O—C_{1-6}$ alkyl group, and other symbols are defined above.

Step 1P

By subjecting compound (3G) to a reaction similar to Step 7D, compound (1P) is obtained.

Step 2P

By reacting compound (1P) obtained in Step 1P with compound (2P) in N,N-dimethylformamide, tetrahydrofuran, diethyl ether, dimethyl sulfoxide, acetone, acetonitrile and the like or a mixed solvent thereof, in the presence of a base such as sodium hydride, potassium carbonate, sodium carbonate and the like and potassium iodide, compound (3P) is obtained.

<Production Method of Compound Wherein Ring A is Phenyl Group Substituted by Carboxy-$C_{2-6}$ Alkyl Group>

(1Q)

-continued

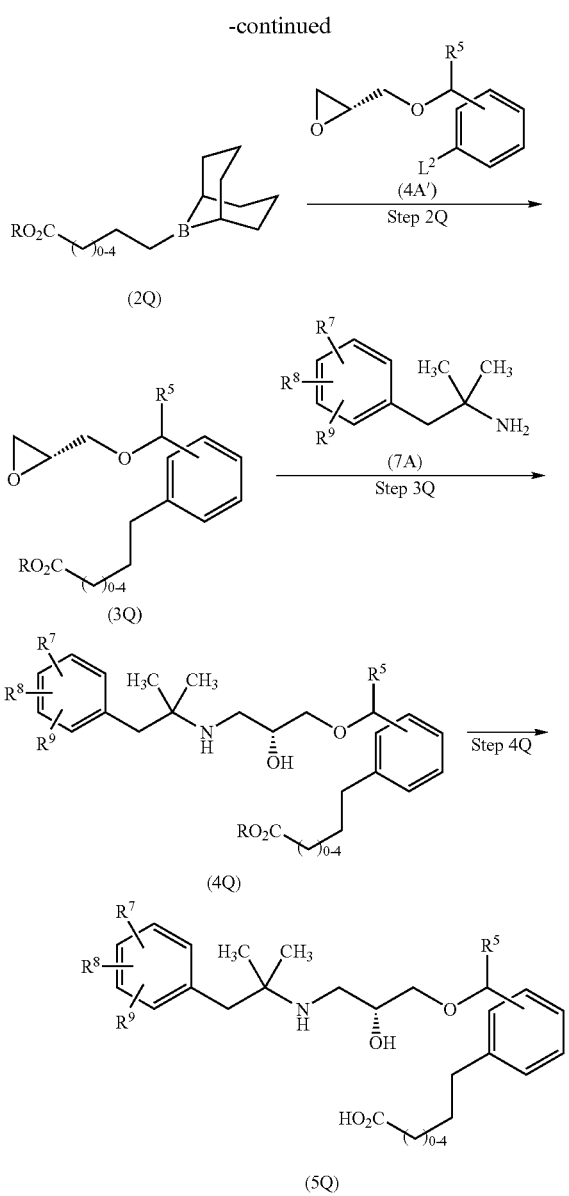

wherein each symbol is as defined above.

Step 1Q compound (2Q) is obtained by reacting compound (1Q) with 9-borabicyclo[3.3.1]nonane in tetrahydrofuran.

Step 2Q

Compound (3Q) is obtained by reacting compound (4A') obtained in the same manner as in Step 2A with compound (2Q) obtained in Step 1Q in a solvent such as tetrahydrofuran, diethyl ether, N,N-dimethylformamide, dimethyl sulfoxide, acetonitrile and the like in the presence of [bis(diphenylphosphino)ferrocene]dichloropalladium(II) (or dichloromethane complex thereof) and a base such as tripotassium phosphate and the like.

Step 3Q

By subjecting compound (3Q) obtained in Step 2Q and compound (7A) to a reaction similar to Step 4A, compound (4Q) is obtained.

Step 4Q

By subjecting compound (4Q) obtained in Step 3Q to a reaction similar to Step 7D, compound (5Q) is obtained.

A compound wherein ring A is a phenyl group substituted by carboxyethyl group can also be produced by the following method.

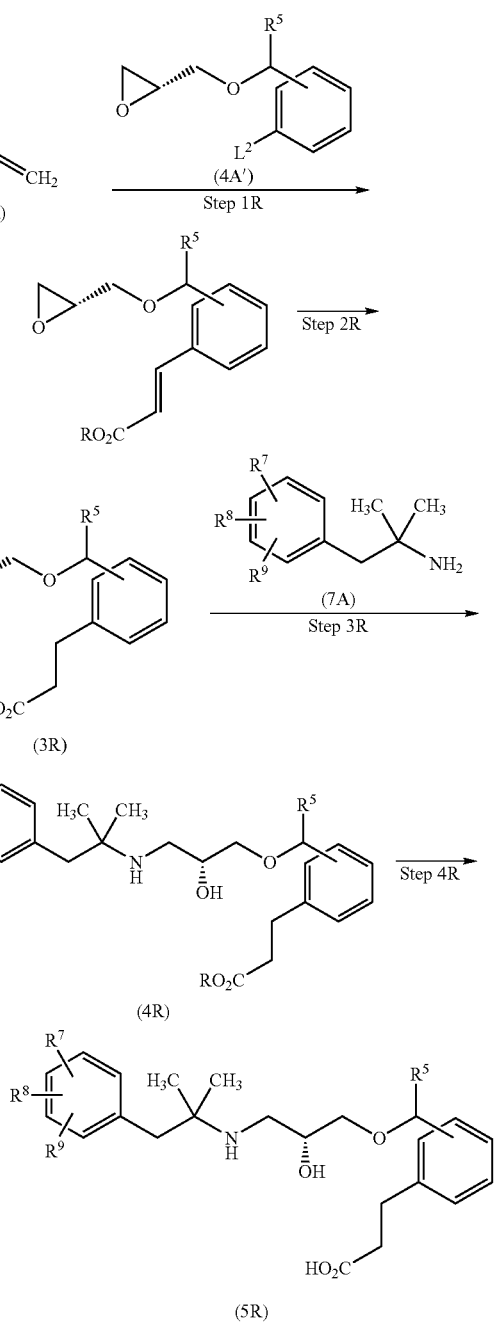

wherein each symbol is as defined above.

Step 1R

Compound (1R) is reacted with compound (4A') in a solvent such as tetrahydrofuran, diethyl ether, N,N-dimethylformamide, dimethyl sulfoxide, acetonitrile and the like, in the presence of a catalyst such as palladium (II) is acetate, tri-o-tolylphosphine and the like and a base such as triethylamine and the like at room temperature to refluxing temperature to give compound (2R).

Step 2R

By subjecting compound (2R) obtained in Step 1 to a catalytic reduction by a conventional method, compound (3R) is obtained. For example, compound (3R) is obtained by reducing compound (2R) in a methanol solvent in the presence of a catalyst such as rhodium-alumina and the like.

Step 3R

By subjecting compound (3R) obtained in Step 2R and compound (7A) to a reaction similar to Step 4A, compound (4R) is obtained.

Step 4R

By subjecting compound (4R) obtained in Step 3R to a reaction similar to Step 7D, compound (5R) is obtained.

<Production Method of Compound Wherein Ring A is $C_{3-6}$ Cycloalkyl Group>

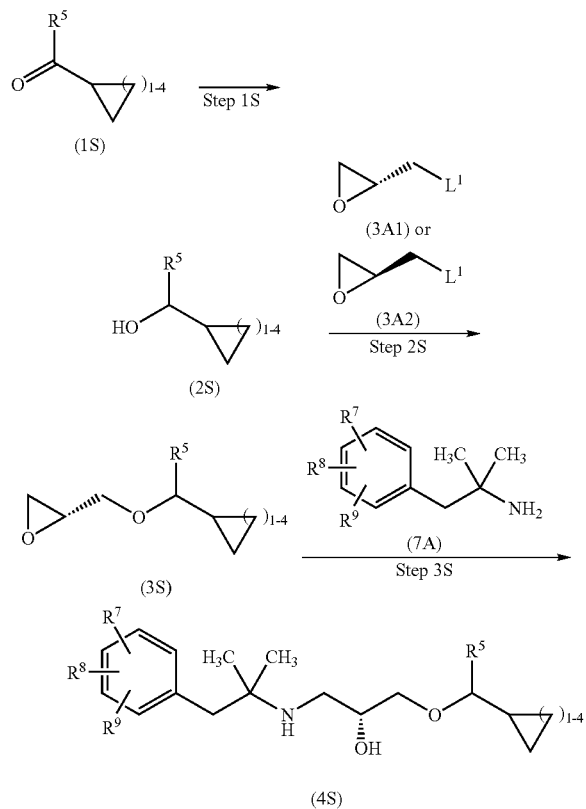

wherein each symbol is as defined above.

Step 1S

By subjecting compound (1S) to a reaction similar to Step 1A, compound (2S) is obtained.

Step 2S

By subjecting compound (2S) obtained in Step 1S and compound (3A1) or compound (3A2) to a reaction similar to Step 2A, compound (3S) is obtained.

Step 3S

By subjecting compound (3S) obtained in Step 2S and compound (7A) to a reaction similar to Step 4A, compound (4S) is obtained.

The compound of the present invention wherein $R^6$ is $R^C$ is obtained by reacting a compound of the present invention wherein $R^6$ is a hydrogen atom with a compound such as acid anhydride represented by $(R^C)_2O$ ($R^C$ is as defined above) or acyl halide represented by $R^C$-$L^1$ (each symbol is as defined above) and the like in chloroform, methylene chloride, tetrahydrofuran, toluene, ethyl acetate and the like or a mixed solvent thereof, in the presence of a base such as pyridine, triethylamine, dimethylaminopyridine and the like.

When a salt of a compound represented by the formula (1) or (1') is desired, known methods can be used. For example, when an acid addition salt is desired, a compound represented by the formula (1) or (1') is dissolved in water, methanol, ethanol, n-propanol, isopropanol, diethyl ether, tetrahydrofuran, 1,4-dioxane, ethyl acetate, dichloromethane, 1,2-dichloroethane, chloroform and the like or a mixed solvent thereof, the above-mentioned solvent wherein the desired acid has been dissolved is added and the precipitated crystals are collected by filtration, or concentrated under reduced pressure.

When a basic salt is desired, a compound represented by the formula (1) or (1') is dissolved in water, methanol, ethanol, n-propanol, isopropanol, tetrahydrofuran, 1,4-dioxane, and the like or a mixed solvent thereof, the above-mentioned solvent wherein the equivalent weight of desired base has been dissolved is added and the precipitated crystals are collected by filtration, or concentrated under reduced pressure.

When an acid addition salt of a compound represented by the formula (1) or (1') is to be converted to a free form, acid addition salt of a compound represented by the formula (1) or (1') is added to an aqueous solution of a base such as sodium hydrogencarbonate, potassium hydrogen carbonate, sodium carbonate, potassium carbonate, sodium hydroxide, potassium hydroxide, lithium hydroxide and the like to adjust pH of the aqueous solution to neutral-weakly acidic, and the compound is partitioned into two layers consisting of the aqueous solution and a solvent such as ethyl acetate, dichloromethane, 1,2-dichloroethane, chloroform, methyl ethyl ketone or toluene and the like, whereby a free form of the compound represented by the formula (1) or (1') can be obtained.

When a basic salt of a compound represented by the is formula (1) or (1') is to be converted to a free form, an aqueous solution of acid such as hydrochloric acid, hydrobromic acid, sulfuric acid, acetic acid, citric acid and the like is added to an aqueous solution of a basic salt of a compound represented by the formula (1) or (1') and the precipitated solid is collected by filtration, or the compound is partitioned into two layers consisting of the aqueous solution and a solvent such as ethyl acetate, dichloromethane, 1,2-dichloroethane, chloroform, methyl ethyl ketone or toluene and the like, whereby a free form of the compound represented by the formula (1) or (1') can be obtained.

The thus-obtained compound of the formula (1) or (1') of the present invention has a superior calcium receptor antagonistic action. When the compound of the present invention is to be used as a therapeutic agent of osteoporosis, hypoparathyreosis, osteosarcoma, periodontal disease, bone fracture, osteoarthrisis, chronic rheumatoid arthritis, Paget's disease, humoral hypercalcemia, autosomal dominant hypocalcemia and the like, it is generally administered systemically or topically, and orally or parenterally.

While the dose varies depending on age, body weight, condition, treatment effect, administration method, treatment period and the like, it is generally 0.01 mg to 10 g for an adult per day, which is given once or in several portions a day by oral or parenteral administration.

When the compound of the present invention is prepared into a solid composition for oral administration, a dosage form of tablet, pill, powder, granule and the like can be employed. In such a solid composition, one or more active ingredient is admixed with at least one inert diluent, dispersing agent, absorbent and the like, such as lactose, mannitol, glucose, hydroxypropyl cellulose, crystalline cellulose, starch, polyvinyl hydrin, magnesium aluminometasilicate, anhydrous silicic acid powder and the like. The composition may contain an additive other than diluent according to a conventional method.

For preparation of tablets or pills, film of gastric or enteric material such as sucrose, gelatin, hydroxypropyl cellulose, hydroxymethylcellulose phthalate and the like may be optionally applied or two or more layers may be formed. In addition, they may be prepared into capsules of gelatin or ethylcellulose.

For preparation of liquid composition for oral administration, a dosage form such as pharmaceutically acceptable emulsion, solution, suspension, syrup, elixir and the like can be employed. The diluent to be used is, for example, purified water, ethanol, vegetable oil, emulsifier and the like. This composition may contain diluent and an adjuvant other than the diluent, such as wetting agent, suspending agent, sweetener, flavor, perfume, preservative and the like.

For preparation of parenteral injection, sterile aqueous or nonaqueous solution, solubilizer, suspending agent or emulsifier is used. Examples of the aqueous solution, solubilizer and suspending agent include distilled water for injection, physiological saline, cyclodextrin and derivatives thereof, organic amines such as triethanolamine, diethanolamine, monoethanolamine, triethylamine and the like, inorganic alkali solution and the like.

When a water-soluble solution is to be prepared, for example, propylene glycol, polyethylene glycol, vegetable oil such as olive oil, alcohol such as ethanol, and the like may be used. As the solubilizer, for example, surfactant (forming a mixed micelle) such as polyoxyethylene hydrogenated castor oil, sucrose fatty acid ester and the like, lecithin or hydrogenated lecithin (forming a liposome) and the like can be used. In addition, an emulsion preparation consisting of a water-insoluble solubilizer such as vegetable oil and the like, and lecithin, polyoxyethylene hydrogenated castor oil, polyoxyethylene polyoxypropylene glycol and the like may be formed.

As other compositions for parenteral administration, an external liquid, liniment such as ointment, suppository, pessary and the like, containing one or more active ingredients and prepared by a method known per se may be formulated.

The form of the compound of the present invention for use as a pharmaceutical product is a compound itself (free form), a salt of the compound, a solvate of the compound or a prodrug of the compound, wherein preferred form is a free form, a salt of the compound or a solvate of the compound, particularly preferably a salt of the compound.

EXAMPLES

The compound represented by the formula (1) or (1') and a production method thereof of the present invention are explained in detail by referring to the following Examples, which are not to be construed as limitative.

Example 1

3-[2-[(1R)-1-[(2R)-2-hydroxy-3-[[2-methyl-1-(naphthalen-2-yl)propan-2-yl]amino]propoxy]ethyl]phenyl]propionic acid Step 1

(2R)-2-[[(1R)-1-(2-bromophenyl)ethoxy]methyl]oxirane

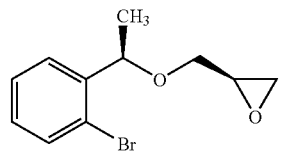

(R)-1-(2-Bromophenyl)ethanol (30.0 g) and (R)-glycidyl nosylate (50.3 g) were dissolved in N,N-dimethylformamide (300 ml), sodium hydride (7.76 g, 60% in oil) was added and the mixture was stirred at room temperature for 2 hr. 10% Aqueous citric acid (600 ml) was added to the reaction mixture, and the mixture was extracted with ethyl acetate. The organic layer was washed successively with water and saturated brine, dried over anhydrous sodium sulfate, and concentrated under reduced pressure. The obtained residue was purified by silica gel column chromatography (hexane:ethyl acetate=6:1) to give the title compound (32.9 g).

$^1$H-NMR (300 MHz, δppm, CDCl$_3$) 7.53-7.49 (2H, m), 7.37-7.32 (1H, m), 7.16-7.10 (1H, m), 4.89 (1H, q, J=6.4 Hz), 3.62-3.57 (1H, m), 3.34-3.28 (1H, m), 3.18-3.12 (1H, m), 2.79-2.76 (1H, m), 2.58-2.55 (1H, m), 1.44 (3H, d, J=6.4 Hz).

Step 2

Methyl 3-[2-[(1R)-1-(((2R)-oxiranyl)methoxy)ethyl]phenyl]acrylate

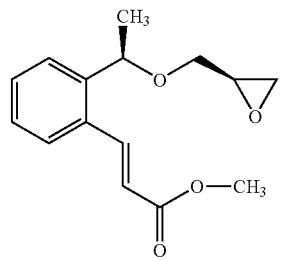

(2R)-2-[[(1R)-1-(2-Bromophenyl)ethoxy]methyl]oxirane (1.00 g) obtained in Step 1 was dissolved in acetonitrile (10 ml), palladium acetate (II) (45 mg), tri-o-tolylphosphine (63 mg), triethylamine (0.65 ml) and methyl acrylate (0.42 ml) were added, and the mixture was heated under reflux for 3 hr. The reaction mixture was cooled to room temperature, and, after filtration through celite, concentrated under reduced pressure. The obtained residue was purified by silica gel column chromatography (hexane:ethyl acetate=5:1) to give the title compound (203 mg).

Step 3 methyl 3-[2-[(1R)-1-(((2R)-oxiranyl)methoxy)ethyl]phenyl]propionate

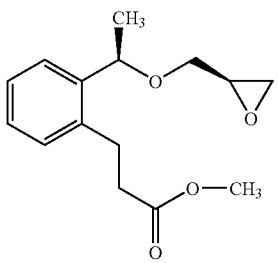

Methyl 3-[2-[(1R)-1-(((2R)-oxiranyl)methoxy)ethyl]phenyl]acrylate (330 mg) obtained in Step 2 was dissolved in methanol (10 ml), 5% rhodium-alumina (43 mg) was added, and the mixture was hydrogenated at atmospheric pressure overnight. The reaction mixture was filtered through Celite, and concentrated under reduced pressure. The obtained residue was purified by silica gel column chromatography (hexane:ethyl acetate=4:1) to give the title compound (291 mg).

Step 4

Methyl 3-[2-[(1R)-1-[(2R)-2-hydroxy-3-[[2-methyl-1-(naphthalen-2-yl)propan-2-yl]amino]propoxy]ethyl]phenyl]propionate

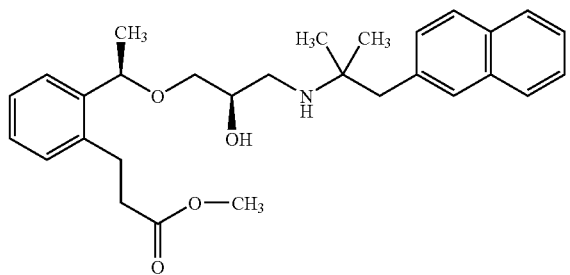

Methyl 3-[2-[(1R)-1-(((2R)-oxiranyl)methoxy)ethyl]phenyl]propionate (286 mg) obtained in Step 3 was dissolved in acetonitrile (10 ml), [2-methyl-1-(naphthalen-2-yl)propan-2-yl]amine (218 mg) and lithium perchlorate (157 mg) were successively added, and the mixture was heated under reflux overnight. The reaction mixture was concentrated under reduced pressure. The obtained residue was purified by silica gel column chromatography (chloroform:methanol=10:1) to give the title compound (539 mg).

Step 5

3-[2-[(1R)-1-[(2R)-2-hydroxy-3-[[2-methyl-1-(naphthalen-2-yl)propan-2-yl]amino]propoxy]ethyl]phenyl]propionic acid

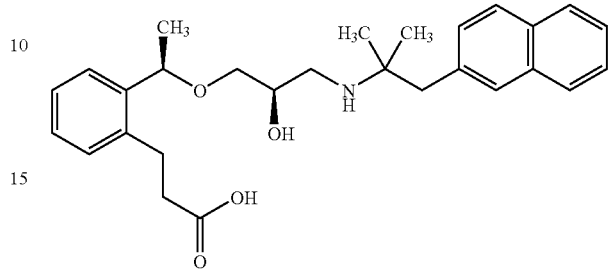

Methyl 3-[2-[(1R)-1-[(2R)-2-hydroxy-3-[[2-methyl-1-(naphthalen-2-yl)propan-2-yl]amino]propoxy]ethyl]phenyl]propionate (539 mg) obtained in Step 4 was dissolved in methanol (20 ml) and tetrahydrofuran (20 ml), 4N aqueous sodium hydroxide (2.5 ml) was added and the mixture was stirred at 50° C. for 8 hr. The reaction mixture was concentrated under reduced pressure. The obtained residue was diluted with water, neutralized with 10% aqueous citric acid, and the mixture was extracted with ethyl acetate. The organic layer was washed successively with water and brine, dried over anhydrous sodium sulfate, and concentrated under reduced pressure to give the title compound (332 mg).

$^1$H-NMR (300 MHz, δppm, DMSO-$d_6$) 7.92-7.86 (3H, m), 7.75 (1H, s), 7.54-7.47 (2H, m), 7.39-7.37 (2H, m), 7.27-7.20 (3H, m), 4.78 (1H, q, J=6.3 Hz), 3.96-3.94 (1H, m), 3.36-3.34 (1H, m), 3.26-3.10 (2H, m), 3.10 (2H, s), 2.92-2.86 (3H, m), 2.49-2.52 (2H, m), 1.36 (3H, d, J=6.3 Hz), 1.22 (6H, s).

MS(ESI, m/z) 450(M+H)$^+$.

Example 2

6-[2-[(1R)-1-[(2R)-2-hydroxy-3-[[2-methyl-1-(naphthalen-2-yl)propan-2-yl]amino]propoxy]ethyl]phenyl]hexanoic acid

Step 1

Methyl 6-[2-[(1R)-1-(((2R)-oxiranyl)methoxy)ethyl]phenyl]hexanoate

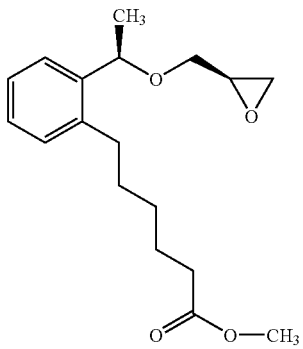

To methyl 5-hexenoate (608 mg) was added 0.5 M 9-bora bicyclo[3.3.1]nonane-tetrahydrofuran solution (9.5 ml) under ice-cooling and the mixture was stirred overnight at room temperature. The reaction mixture was added dropwise to a suspension of tetrahydrofuran (10 ml), (2R)-2-[[(1R)-1-(2-bromophenyl)ethoxy]methyl]oxirane (1.06 g) obtained in Example 1, Step 1, tri-potassium phosphate (1.32 g), [bis(diphenylphosphino)ferrocene]dichloropalladium(II) complex with dichloromethane (170 mg) and the mixture was heated under reflux for 7 hr. The reaction mixture was cooled to room temperature, water was added, and the mixture was extracted with ethyl acetate. The organic layer was washed with brine, dried over anhydrous sodium sulfate, and concentrated under reduced pressure. The obtained residue was purified by silica gel column chromatography (hexane:ethyl acetate=7:1) to give the title compound (621 mg).

Step 2

Methyl 6-[2-[(1R)-1-[(2R)-2-hydroxy-3-[[2-methyl-1-(naphthalen-2-yl)propan-2-yl]amino]propoxy]ethyl]phenyl]hexanoate

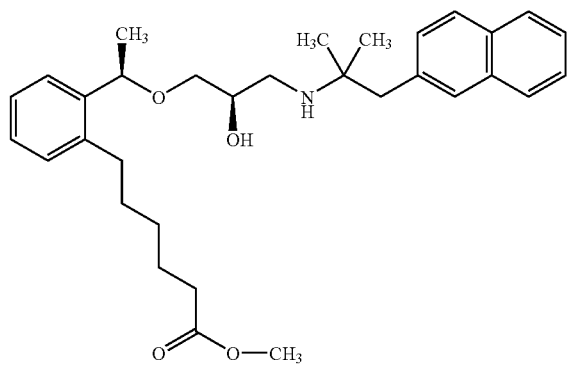

In the same manner as in Example 1, Step 4, the title compound (589 mg) was obtained from methyl 6-[2-[(1R)-1-(((2R)-oxiranyl)methoxy)ethyl]phenyl]hexanoate (616 mg) obtained in Step 1 and [2-methyl-1-(naphthalen-2-yl)propan-2-yl]amine (422 mg).

Step 3

6-[2-[(1R)-1-[(2R)-2-hydroxy-3-[[2-methyl-1-(naphthalen-2-yl)propan-2-yl]amino]propoxy]ethyl]phenyl]hexanoic acid

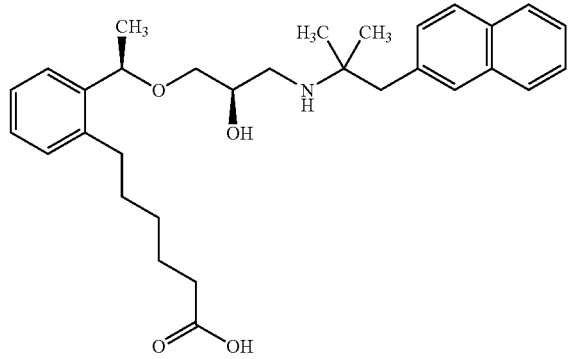

The title compound (483 mg) was obtained in the same manner as in Example 1, Step 5, from methyl 6-[2-[(1R)-1-[(2R)-2-hydroxy-3-[[2-methyl-1-(naphthalen-2-yl)propan-2-yl]amino]propoxy]ethyl]phenyl]hexanoate (583 mg) obtained in Step 2.

$^1$H-NMR (300 MHz, δppm, DMSO-$d_6$) 7.89-7.83 (3H, m), 7.72 (1H, s), 7.51-7.45 (2H, m), 7.36-7.34 (2H, m), 7.22-7.13 (3H, m), 4.74 (1H, q, J=5.7 Hz), 3.92-3.90 (1H, m), 3.32-3.30 (1H, m), 3.22-3.20 (1H, m), 3.06-3.04 (1H, m), 3.05 (2H, s), 2.81-2.79 (1H, m), 2.59 (2H, t, J=7.8 Hz), 2.19 (2H, t, J=7.3 Hz), 1.57-1.48 (4H, m), 1.40-1.38 (2H, m), 1.33 (3H, d, J=5.7 Hz), 1.18 (6H, s).

MS(ESI, m/z) 492(M+H)$^+$.

Example 3

(2R)-1-dicyclopropylmethoxy-3-[[2-methyl-1-(naphthalen-2-yl)propan-2-yl]amino]propan-2-ol Step 1 dicyclopropylmethanol

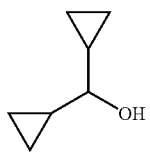

To a solution of dicyclopropylketone (1.21 g) in methanol (12 ml) was added sodium borohydride (407 mg), and the mixture was stirred at room temperature for 3 hr. The reaction mixture was concentrated under reduced pressure. Water was added to the obtained residue, and the mixture was extracted with ethyl acetate. The organic layer was washed successively with water and brine, dried over anhydrous sodium sulfate, and concentrated under reduced pressure to give the title compound (885 mg).

Step 2

(2R)-2-[(dicyclopropylmethoxy)methyl]oxirane

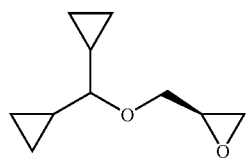

Dicyclopropylmethanol (880 mg) obtained in Step 1 and (R)-glycidyl nosylate (3.05 g) were dissolved in tetrahydrofuran (7.3 ml), sodium hydride (471 mg) and dimethyl sulfoxide (1.5 ml) were added under ice-cooling, and the mixture was stirred at room temperature for 5 hr. Water was poured into the reaction mixture, and the mixture was extracted with diethyl ether. The organic layer was washed successively with water and brine, dried over anhydrous sodium sulfate, and concentrated under reduced pressure. The obtained residue was purified by silica gel column chromatography (hexane:ethyl acetate=90:10) to give the title compound (760 mg).

Step 3

(2R)-1-dicyclopropylmethoxy-3-[[2-methyl-1-(naphthalen-2-yl)propan-2-yl]amino]propan-2-ol

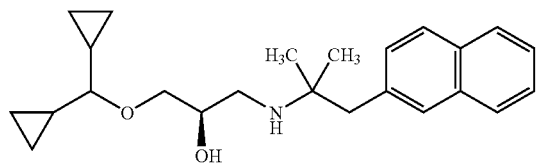

The title compound (548 mg) was obtained in the same manner as in Example 1, Step 4, from (2R)-2-[(dicyclopropylmethoxy)methyl]oxirane (420 mg) obtained in Step 2 and [2-methyl-1-(naphthalen-2-yl)propan-2-yl]amine (498 mg).

¹H-NMR (300 MHz, δppm, CDCl₃) 7.84-7.79 (3H, m), 7.70 (1H, s), 7.49-7.47 (2H, m), 7.35-7.32 (1H, m), 4.15-4.05 (1H, m), 3.70-3.68 (2H, d, J=5.5 Hz), 3.26-3.21 (1H, m), 3.11-3.02 (3H, m), 2.06-2.00 (1H, t, J=8.1 Hz), 1.36 (3H, s), 1.34 (3H, s), 0.80-0.75 (2H, m), 0.45-0.43 (4H, m), 0.23-0.12 (4H, m).

MS(ESI, m/z) 368(M+H)⁺.

Example 4

[2'-[(1R)-1-[(2R)-2-hydroxy-3-[[2-methyl-1-(naphthalen-2-yl)propan-2-yl]amino]propoxy]ethyl]biphenyl-3-yl]acetic acid Step 1 ethyl 3-bromophnylacetate

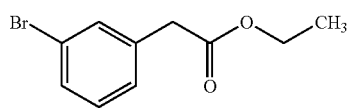

3-Bromophenylacetic acid (5.03 g) was dissolved in ethanol (40 ml), conc. sulfuric acid (0.5 ml) was added, and the mixture was stirred overnight at room temperature. The reaction mixture was concentrated under reduced pressure. Water was added to the obtained residue, and the mixture was extracted with ethyl acetate. The organic layer was washed successively with water, saturated aqueous sodium hydrogencarbonate and brine, dried over sodium sulfate, and concentrated under reduced pressure to give the title compound (5.4 g).

Step 2 ethyl [2'-[(1R)-1-(((2R)-oxiranyl)methoxy)ethyl]biphenyl-3-yl]acetate

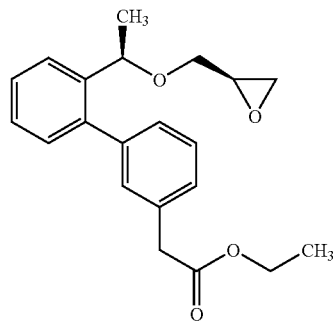

ethyl 3-bromophenylacetate (2.00 g) obtained in Step 1 was dissolved in dimethyl sulfoxide (42 ml), [bis(diphenylphosphino)ferrocene]dichloropalladium(II) complex with dichloromethane (202 mg), potassium acetate (2.42 g) and bispinacolatediboron (2.30 g) were added and the mixture was stirred at 80° C. for 5 hr. The reaction mixture was cooled to room temperature, water and ethyl acetate were added and, after filtration through Celite, the mixture was extracted with ethyl is acetate. The organic layer was washed successively with water and brine, dried over anhydrous sodium sulfate, and concentrated under reduced pressure. The obtained residue was dissolved in ethanol (17 ml), to a mixture of tetrakis(triphenylphosphine)palladium(0) (476 mg) and (2R)-2-[[(1R)-(2-bromophenyl)ethoxy]methyl]oxirane (2.12 g) obtained in Example 1, Step 1 in toluene (17 ml) was added, 2M-aqueous sodium carbonate (8.2 ml) was further added and the mixture was heated under reflux overnight. The reaction mixture was cooled to room temperature, water and ethyl acetate were added and, after filtration through Celite, the mixture was extracted with ethyl acetate. The organic layer was washed successively with water and brine, dried over sodium sulfate, and concentrated under reduced pressure. The obtained residue was purified by silica gel column chromatography (hexane:ethyl acetate=4:1) to give the title compound (1.38 g).

Step 3 ethyl [2'-[(1R)-1-[(2R)-2-hydroxy-3-[[2-methyl-1-(naphthalen-2-yl)propan-2-yl]amino]propoxy]ethyl]biphenyl-3-yl]acetate

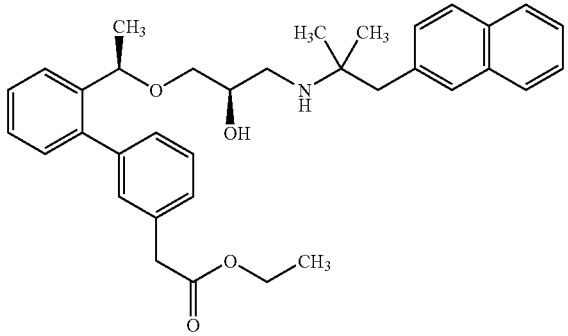

The title compound (410 mg) was obtained in the same manner as in Example 1, Step 4, from ethyl [2'-[(1R)-1-(((2R)-oxiranyl)methoxy)ethyl]biphenyl-3-yl]acetate (340 mg) obtained in Step 2 and [2-methyl-1-(naphthalen-2-yl)propan-2-yl]amine (199 mg).

Step 4

[2'-[(1R)-1-[(2R)-2-hydroxy-3-[[2-methyl-1-(naphthalen-2-yl)propan-2-yl]amino]propoxy]ethyl]biphenyl-3-yl]acetic acid

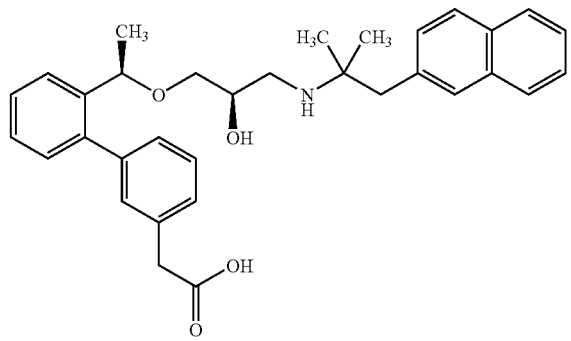

ethyl [2'-[(1R)-1-[(2R)-2-Hydroxy-3-[[2-methyl-1-(naphthalen-2-yl)propan-2-yl]amino]propoxy]ethyl]biphenyl-3-yl]acetate (400 mg) obtained in Step 3 was dissolved in methanol (2 ml) and tetrahydrofuran (4 ml), 1N-aqueous sodium hydroxide (1.5 ml) was added, and the mixture was stirred at room temperature for 6 hr. The reaction mixture was concentrated under reduced pressure. The obtained residue was diluted with water and neutralized with 10% aqueous citric acid. The precipitated white solid was collected by filtration and dried in vacuo to give the title compound (325mg).

$^1$H-NMR (300 MHz, δppm, DMSO-$d_6$) 7.90-7.82 (3H, m), 7.73 (1H, s), 7.53-7.23 (9H, m), 7.18 (1H, dd, J=7.7, 1.1 Hz), 7.11 (1H, d, J=7.7 Hz), 4.50 (1H, q, J=6.3 Hz), 3.87-3.80 (1H, m), 3.54 (1H, d, J=14 Hz), 3.47 (1H, d, J=14 Hz), 3.20 (2H, d, J=5.9 Hz), 3.02 (2H, s), 2.90 (1H, dd, J=12, 2.6 Hz), 2.67 (1H, dd, J=12, 8.6 Hz), 1.19 (3H, d, J=6.3 Hz), 1.14 (6H, s).

MS(ESI, m/z) 512(M+H)$^+$.

Example 5

N-[[2'-[(1R)-1-[(2R)-2-hydroxy-3-[[2-methyl-1-(naphthalen-2-yl)propan-2-yl]amino]propoxy]ethyl]biphenyl-4-yl]methyl]acetamide Step 1

N-(4-iodobenzyl)acetamide

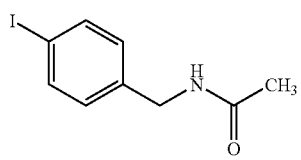

4-Iodobenzylamine (5.32 g) was dissolved in chloroform (50 ml), and, under ice-cooling, pyridine (2.76 ml) and acetic anhydride (2.58 ml) were added and the mixture was stirred for 4 hr. The reaction mixture was washed successively with water, 1N-hydrochloric acid, water and saturated brine, dried over anhydrous sodium sulfate, and concentrated under reduced pressure. The obtained residue was purified by silica gel column chromatography (hexane:ethyl acetate=1:2-1:3) to give the title compound (5.18 g).

Step 2

N-[[2'-[(1R)-1-(((2R)-oxiranyl)methoxy)ethyl]biphenyl-4-yl]methyl]acetamide

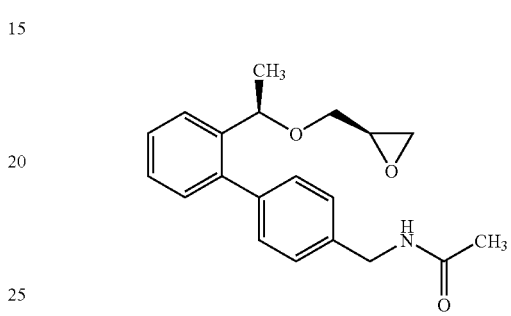

The title compound (706 mg) was obtained in the same manner as in Example 4, Step 2, from N-(4-iodobenzyl)acetamide (2.00 g) obtained in Step 1 and (2R)-2-[[(1R)-1-(2-bromophenyl)ethoxy]methyl]oxirane (1.87 g) obtained in Example 1, Step 1.

Step 3

N-[[2'-[(1R)-1-[(2R)-2-hydroxy-3-[[2-methyl-1-(naphthalen-2-yl)propan-2-yl]amino]propoxy]ethyl]biphenyl-4-yl]methyl]acetamide

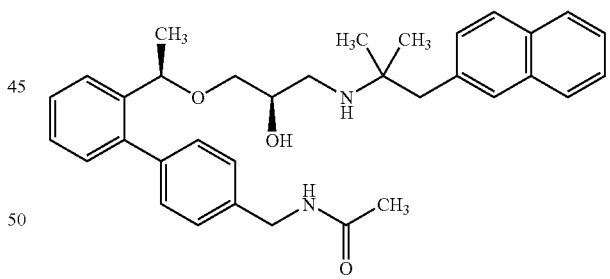

The title compound (510 mg) was obtained in the same manner as in Example 1, Step 4, from N-[[2'-[(1R)-1-(((2R)-oxiranyl)methoxy)ethyl]biphenyl-4-yl]methyl]acetamide (700 mg) obtained in Step 2 and [2-methyl-1-(naphthalen-2-yl)propan-2-yl]amine (428 mg).

$^1$H-NMR (300 MHz, δppm, DMSO-$d_6$) 8.41 (1H, t, J=5.9 Hz), 7.92-7.86 (3H, m), 7.74 (1H, s), 7.56-7.42 (4H, m), 7.39-7.33 (4H, m), 7.25(2H, d, J=8.0 Hz), 7.17 (1H, dd, J=7.7, 1.1 Hz), 4.49 (1H, q, J=6.2 Hz), 4.32 (2H, d, J=5.9 Hz), 3.80 (1H, brs), 3.16-3.06 (5H, m), 2.85-2.75 (1H, m), 1.90 (3H, s), 1.30 (3H, d, J=6.2 Hz), 1.20 (6H, s).

MS(ESI, m/z) 525(M+H)$^+$.

Example 6

(Z)-butenedioic acid mono-[(2R)-1-[(1R)-(cyclopropyl)-(2-methylphenyl)methoxy]-3-[[2-methyl-1-(naphthalen-2-yl)propan-2-yl]amino]propan-2-yl] ester

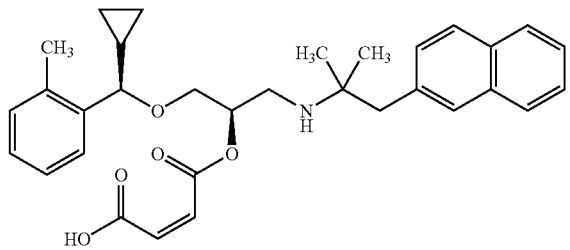

(2R)-1-[(1R)-(Cyclopropyl)-(2-methylphenyl)methoxy]-3-[[2-methyl-1-(naphthalen-2-yl)propan-2-yl]amino]propan-2-ol (1.25g) was dissolved in chloroform (10 ml) and, under ice-cooling, pyridine (0.485 ml) and maleic anhydride (294 mg) were added and the mixture was stirred for 4 hr. The reaction mixture was concentrated under reduced pressure, and diethyl ether was added to the obtained residue. The organic layer was washed successively with water and saturated brine, dried over anhydrous sodium sulfate, and concentrated under reduced pressure. The obtained residue was purified by silica gel column chromatography (chloroform:methanol=98:2-95:5) to give the title compound (1.40 g).

$^1$H-NMR (300 MHz, δppm, DMSO-$d_6$) 8.00-7.00 (11H, m), 6.32 (1H, d, J=11.7 Hz), 5.83 (1H, d, J=11.7 Hz), 5.20-5.00 (1H, m), 4.20-3.90 (1H, m), 3.60-3.10 (6H, m), 2.30 (3H, s), 1.40-1.00 (7H, m), 0.60-0.05 (4H, m).

MS(ESI, m/z) 510(M+H)$^+$.

Example 7

(R)-3-[[2-methyl-1-(naphthalen-2-yl)propan-2-yl]amino]-1-[1-[4'-(1H-tetrazol-5-yl)biphenyl-2-yl]ethoxy]propan-2-ol Step 1

2'-[1-(((2R)-oxiranyl)methoxy)ethyl]biphenyl-4-carbonitrile

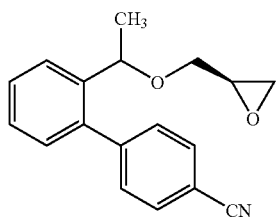

(R)-2-[1-(2-Bromophenyl)ethoxymethyl]oxirane (8.24 g) was dissolved in toluene (38 ml) and ethanol (150 ml), 2M-aqueous sodium carbonate (80 ml), 4-cyanophenylboronic acid (5.65 g) and tetrakis(triphenylphosphine)palladium(0) (1.85 g) were successively added, and the mixture was heated under reflux overnight. The reaction mixture was cooled to room temperature, and concentrated under reduced pressure. Water was added to the obtained residue, and the mixture was extracted 3 times with diethyl ether. The organic layer was washed successively with water and brine, dried over sodium sulfate, and concentrated under reduced pressure. The obtained residue was purified by silica gel chromatography (hexane:ethyl acetate=4:1) to give the title compound (2.40 g).

Step 2

2'-[1-[(2R)-2-hydroxy-3-[[2-methyl-1-(naphthalen-2-yl)propan-2-yl]amino]propoxy]ethyl]biphenyl-4-carbonitrile

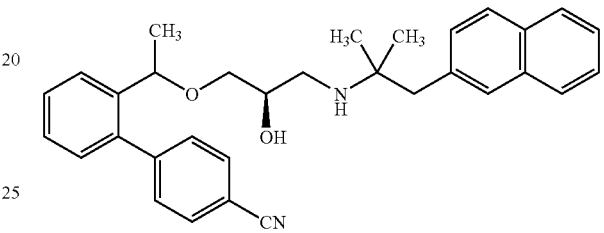

The title compound (3.18 g) was obtained in the same manner as in Example 1, Step 4, from 2'-[1-(((2R)-oxiranyl)methoxy)ethyl]biphenyl-4-carbonitrile (2.40 g) obtained in Step 1 and [2-methyl-1-(naphthalen-2-yl)propan-2-yl]amine (1.71 g).

Step 3

(R)-3-[[2-methyl-1-(naphthalen-2-yl)propan-2-yl]amino]-1-[1-[4'-(1H-tetrazol-5-yl)biphenyl-2-yl]ethoxy]propan-2-ol

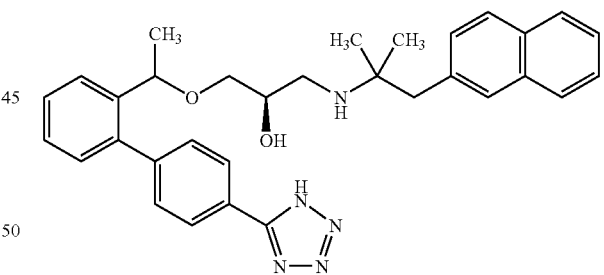

2'-[1-[(2R)-2-Hydroxy-3-[[2-methyl-1-(naphthalen-2-yl)propan-2-yl]amino]propoxy]ethyl]biphenyl-4-carbonitrile (500 mg) obtained in Step 2 was dissolved in N,N-dimethylformamide (6.0 ml), ammonium chloride (535 mg) and sodium azide (676 mg) were successively added and the mixture was stirred overnight at 115° C. Water was added to the reaction mixture, and the precipitated solid was collected by filtration. The solid was dissolved in methanol, water was added and the mixture was concentrated under reduced pressure. The precipitated solid was collected by filtration to give the title compound (280 mg).

$^1$H-NMR (300 MHz, δppm, DMSO-$d_6$) 8.08 (2H, d, J=8.2 Hz), 7.92-7.78 (3H, m), 7.74 (1H, s), 7.60-7.43 (4H, m), 7.40-7.35 (4H, m), 7.27-7.19 (1H, m), 4.57 (1H, q, J=6.3

Hz), 3.88-3.80 (1H, m), 3.24-3.04 (5H, m), 2.96-2.81 (1H, m), 1.36-1.33 (3H, m), 1.22 (6H, s).

MS(ESI, m/z) 522(M+H)$^+$.

Example 8

1-(cyclohexyloxycarbonyloxy)ethyl 2'-[1-[(2R)-2-hydroxy-3-[[2-methyl-1-(naphthalen-2-yl)propan-2-yl]amino]propoxy]ethyl]biphenyl-4-carboxylate Step 1

1-chloroethyl cyclohexyl carbonate

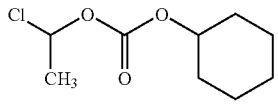

Cyclohexanol (4.58 g) was dissolved in chloroform (75 ml), pyridine (3.63 g) was added, and the mixture was cooled to −78° C. 1-Chloroethyl chlorocarbonate (5.0 ml) was added. The reaction mixture was gradually returned to room temperature and stirred for one day. Water was added to the reaction mixture to separate the organic layer. The organic layer was washed successively with water and brine, dried over sodium sulfate, and concentrated under reduced pressure to give the title compound (8.85 g).

Step 2

2'-[1-[(2R)-2-hydroxy-3-[[2-methyl-1-(naphthalen-2-yl)propan-2-yl]amino]propoxy]ethyl]biphenyl-4-carboxylic acid

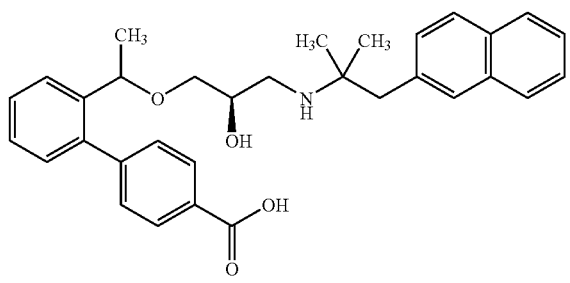

2'-[1-[(2R)-2-Hydroxy-3-[[2-methyl-1-(naphthalen-2-yl)propan-2-yl]amino]propoxy]ethyl]biphenyl-4-carbonitrile (1.0 g) obtained in Example 7, Step 2 was dissolved in ethylene glycol (15 ml). Potassium hydroxide (2.76 g) was added and the mixture was stirred overnight at 160° C. The reaction mixture was allowed to return to room temperature, a small amount of water was added and 10% aqueous citric acid was added to adjust the mixture to pH 4-5. The precipitated solid was collected by filtration to give the title compound (924 mg).

Step 3

1-(cyclohexyloxycarbonyloxy)ethyl 2'-[1-[(2R)-2-hydroxy-3-[[2-methyl-1-(naphthalen-2-yl)propan-2-yl]amino]propoxy]ethyl]biphenyl-4-carboxylate

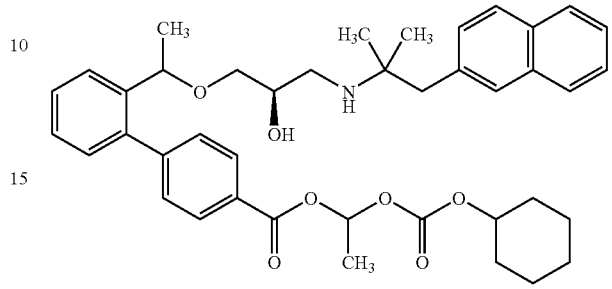

1-Chloroethyl cyclohexyl carbonate (149 mg) obtained in Step 1 was dissolved in N,N-dimethylformamide (5.0 ml), 2'-[1-[(2R)-2-hydroxy-3-[[2-methyl-1-(naphthalen-2-yl)propan-2-yl]amino]propoxy]ethyl]biphenyl-4-carboxylic acid (300 mg) obtained in Step 2, potassium carbonate (99 mg) and potassium iodide (50 mg) were successively added and the mixture was stirred at 60° C. for 1 day. Water was added to the reaction mixture and the mixture was extracted 3 times with ethyl acetate. The organic layer was washed successively with water (3 times) and brine, and dried over sodium sulfate. The organic layer was concentrated under reduced pressure and the obtained residue was purified by silica gel column chromatography (chloroform:methanol=15:1) to give the title compound (381 mg).

$^1$H-NMR (300 MHz, δppm, DMSO-d$_6$) 8.05 (2H, d, J=8.1 Hz), 7.87-7.76 (3H, m), 7.66 (1H, s), 7.60-7.55 (1H, m), 7.50-7.33 (7H, m), 7.21-7.19 (1H, m), 6.93-6.88 (1H, m), 4.62-4.53 (1H, m), 4.44-4.38 (1H, m), 3.60-3.52 (1H, m), 3.45-3.29 (1H, m), 3.13-3.09 (2H, m), 2.78 (2H, brs), 2.70-2.45 (2H, m), 1.88-1.76 (2H, m), 1.68-1.58 (5H, m), 1.50-1.12 (9H, m), 0.99-0.97 (6H, m).

MS(ESI, m/z) 668(M+H)$^+$.

Example 9

5-[2-[1-[(2R)-2-hydroxy-3-[[2-methyl-1-(naphthalen-2-yl)propan-2-yl]amino]propoxy]ethyl]phenyl]thiophene-2-carboxylic acid Step 1 ethyl 5-bromothiophene-2-carboxylate

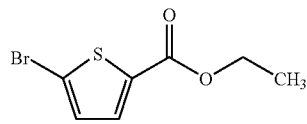

5-Bromothiophene-2-carboxylic acid (5.40 g) was dissolved in ethanol (50 ml), 4-dimethylaminopyridine (3.82 g) and 1-ethyl-3-(3-dimethylaminopropyl)carbodiimide (6.0 g) were successively added, and the mixture was stirred overnight at room temperature. Water was added to the reaction mixture, and the mixture was extracted 3 times with ethyl acetate. The organic layer was washed successively with water, 10% aqueous citric acid (twice), water, saturated aqueous sodium hydrogencarbonate and brine, and dried over sodium sulfate. The organic layer was concentrated under reduced pressure to give the title compound (5.99 g).

Step 2 ethyl 5-(2-acetylphenyl)thiophene-2-carboxylate

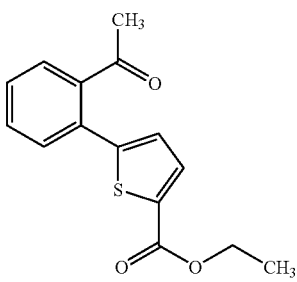

The title compound (3.52 g) was obtained in the same manner as in Example 7, Step 1, from ethyl 5-bromothiophene-2-carboxylate (3.06 g) obtained in Step 1 and 2-acetylphenylboronic acid (2.56 g).

Step 3 ethyl 5-[2-(1-hydroxyethyl)phenyl]thiophene-2-carboxylate

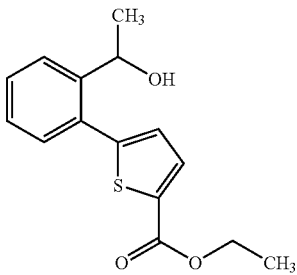

Ethyl 5-(2-acetylphenyl)thiophene-2-carboxylate (3.52 g) obtained in Step 2 was dissolved in ethanol (30 ml) and the mixture was cooled to 0° C. Sodium borohydride was added and the mixture was stirred overnight at 0° C.—room temperature. The reaction mixture was cooled to 0° C., 10% aqueous citric acid was added dropwise and ethanol was evaporated. The reaction mixture was extracted with ethyl acetate, washed successively with water, saturated aqueous sodium hydrogencarbonate and brine, and dried over sodium sulfate. The organic layer was concentrated under reduced pressure and the obtained residue was purified by silica gel column chromatography (hexane:ethyl acetate=3:1) to give the title compound (3.30 g).

Step 4 ethyl 5-[2-[1-(((2R)-oxiranyl)methoxy)ethyl]phenyl]thiophene-2-carboxylate

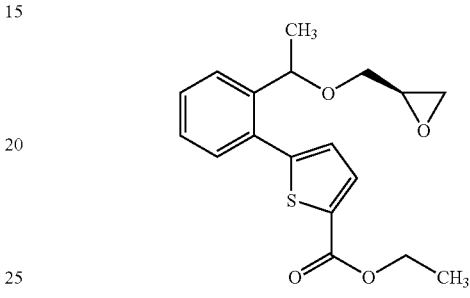

The title compound (1.99 g) was obtained in the same manner as in Example 1, Step 1, from ethyl 5-[2-(1-hydroxyethyl)phenyl]thiophene-2-carboxylate (3.30 g) obtained in Step 3 and (R)-glycidyl nosylate (4.64 g).

Step 5

Ethyl 5-[2-[1-[(2R)-2-hydroxy-3-[[2-methyl-1-(naphthalen-2-yl)propan-2-yl]amino]propoxy]ethyl]phenyl]thiophene-2-carboxylate

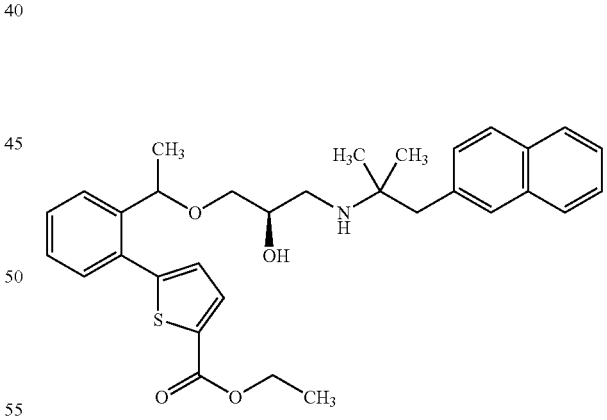

Ethyl 5-[2-[1-(((2R)-oxiranyl)methoxy)ethyl]phenyl]thiophene-2-carboxylate (499 mg) obtained in Step 4 was dissolved in toluene, [2-methyl-1-(naphthalen-2-yl)propan-2-yl]amine (299 mg) and lithium perchlorate (160 mg) were successively added, and the mixture was stirred overnight at room temperature. The reaction mixture was concentrated under reduced pressure and the obtained residue was purified by silica gel column chromatography (chloroform:methanol=30:1) to give the title compound (770 mg).

Step 6

5-[2-[1-[(2R)-2-hydroxy-3-[[2-methyl-1-(naphthalen-2-yl)propan-2-yl]amino]propoxy]ethyl]phenyl]thiophene-2-carboxylic acid

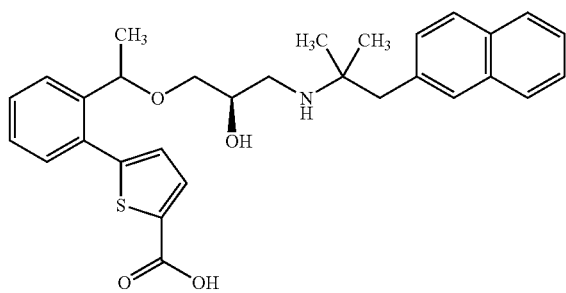

The title compound (672 mg) was obtained in the same manner as in Example 4, Step 4, from ethyl 5-[2-[1-[(2R)-2-hydroxy-3-[[2-methyl-1-(naphthalen-2-yl)propan-2-yl]amino]propoxy]ethyl]phenyl]thiophene-2-carboxylate (770 mg) obtained in Step 5.

$^1$H-NMR (300 MHz, δppm, DMSO-$d_6$) 7.89-7.83 (3H, m), 7.73 (1H, s), 7.60-7.55 (1H, m), 7.49-7.43 (4H, m), 7.39-7.33 (3H, m), 7.01 (1H, d, J=3.4 Hz), 4.82-4.74 (1H, m), 3.92-3.85 (1H, m), 3.22-3.19 (2H, m), 3.08-3.00 (3H, m), 2.89-2.74 (1H, m), 1.34 (3H, d, J=5.2 Hz), 1.18 (6H, s). MS(ESI, m/z) 504(M+H)$^+$.

Example 10

[2-[1-[(2R)-2-hydroxy-3-[[2-methyl-1-(naphthalen-2-yl)propan-2-yl]amino]propoxy]ethyl]phenyl]propynoic acid Step 1

(R)-2-[[1-(2-iodophenyl)ethoxy]methyl]oxirane

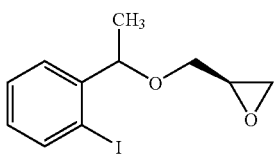

2-Iodoacetophenone (6.30 g) was dissolved in methanol (50 ml), sodium borohydride (726 mg) was added and the mixture was stirred at room temperature for 1.5 hr. 10% Aqueous citric acid was added to the reaction mixture and ethanol was evaporated. Water was added and the mixture was extracted 3 times with ethyl acetate. The organic layer was washed successively with saturated aqueous sodium hydrogencarbonate and brine, and dried over sodium sulfate. The organic layer was concentrated under reduced pressure and the obtained residue was dissolved in tetrahydrofuran (50 ml). The solution was cooled to 0° C., sodium hydride (1.54 g, 60% in oil), (R)-glycidyl nosylate (9.95 g) and dimethyl sulfoxide (10 ml) were successively added, and the mixture was stirred overnight at 0° C.—room temperature. 10% Aqueous citric acid was added to neutralize the reaction mixture, and extracted 3 times with ethyl acetate. The organic layer was washed successively with water (twice) and brine, and dried over sodium sulfate. The organic layer was concentrated under reduced pressure and the obtained residue was purified by silica gel column chromatography (hexane:ethyl acetate=4:1) to give the title compound (6.36 g).

Step 2 methyl [2-[1-(((2R)-oxiranyl)methoxy)ethyl]phenyl]propynoate

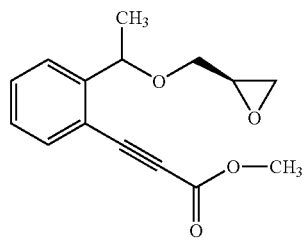

(R)-2-[[1-(2-Iodophenyl)ethoxy]methyl]oxirane (1.50 g) obtained in Step 1 was dissolved in tetrahydrofuran (15 ml), methyl propynoate (1.66 g), tetrakis(triphenylphosphine)palladium(0) (69.2 mg), copper iodide (37.5 mg) and potassium carbonate (2.72 g) were successively added, and the mixture was stirred overnight at 65° C. The reaction mixture was cooled to room temperature, water was added and, after filtration through celite, the filtrate was extracted with ethyl acetate. The organic layer was washed with brine, dried over anhydrous sodium sulfate, and concentrated under reduced pressure. The obtained residue was purified by silica gel column chromatography (hexane:ethyl acetate=4:1) to give the title compound (43 mg).

Step 3

Methyl [2-[1-[(2R)-2-hydroxy-3-[[2-methyl-1-(naphthalen-2-yl)propan-2-yl]amino]propoxy]ethyl]phenyl]propynoate

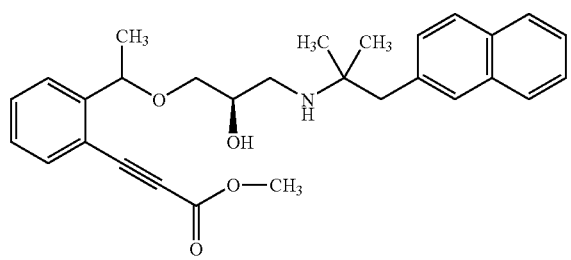

The title compound (20 mg) was obtained in the same manner as in Example 9, Step 5, from methyl [2-[1-(((2R)-oxiranyl)methoxy)ethyl]phenyl]propynoate (40.0 mg) obtained in Step 2 and [2-methyl-1-(naphthalen-2-yl)propan-2-yl]amine (30 mg).

Step 4

[2-[1-[(2R)-2-hydroxy-3-[[2-methyl-1-(naphthalen-2-yl)propan-2-yl]amino]propoxy]ethyl]phenyl]propynoic acid

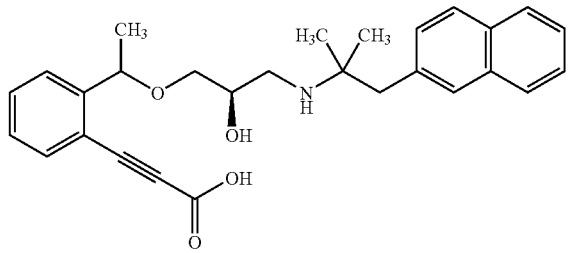

The title compound (5.8 mg) was obtained in the same manner as in Example 4, Step 4, from methyl [2-[1-[(2R)-2-hydroxy-3-[[2-methyl-1-(naphthalen-2-yl)propan-2-yl]amino]propoxy]ethyl]phenyl]propynoate (20 mg) obtained in Step 3.

$^1$H-NMR (300 MHz, δppm, DMSO-d$_6$) 7.92-7.86 (3H, m), 7.77 (1H, s), 7.54-7.38 (6H, m), 7.33-7.28 (1H, m), 4.97 (1H, q, J=6.3 Hz), 4.15-4.09 (1H, m), 3.48-3.18 (3H, m), 3.14 (2H, s), 3.01-2.94 (1H, m), 1.42 (3H, d, J=6.3 Hz), 1.25(6H, s).

MS(ESI, m/z) 446(M+H)$^+$.

Example 11

Monoethyl [2'-[(1R)-1-[(2R)-2-hydroxy-3-[[2-methyl-1-(naphthalen-2-yl)propan-2-yl]amino]propoxy]ethyl]biphenyl-4-yl]phosphonate Step 1

Diethyl (4-bromophenyl)phosphonate

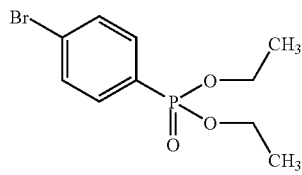

1,4-Dibromobenzene (2.36 g), diethyl phosphite (1.52 g) and triethylamine (1.53 ml) were dissolved in toluene, tetrakis(triphenylphosphine)palladium(0) (578 mg) was added, and the mixture was stirred at 80° C. for 2 hr. The reaction mixture was cooled to room temperature, and the mixture was extracted with ethyl acetate. The organic layer was washed successively with water and brine, dried over sodium sulfate, and concentrated under reduced pressure. The obtained residue was purified by silica gel column chromatography (hexane:ethyl acetate=1:1) to give the title compound (1.16 g).

Step 2

Diethyl [2-[(1R)-1-(((2R)-oxiranyl)methoxy)ethyl]phenyl]phosphonate

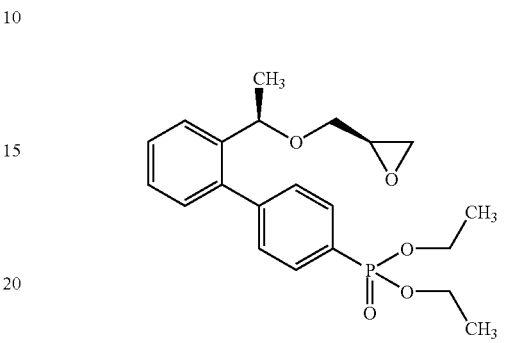

Diethyl (4-bromophenyl)phosphonate (1.16 g) obtained in Step 1 and bis(pinacolato)diboron (1.11 g) were dissolved in dimethyl sulfoxide (15 ml),

[bis(diphenylphosphino)ferrocene]dichloropalladium(II) (146 mg) and potassium acetate (1.17 g) were added and the mixture was stirred at 80° C. for 14 hr. Then, 2M-aqueous sodium carbonate solution (10 ml),

[bis(diphenylphosphino)ferrocene]dichloropalladium(II) (146 mg) and (2R)-2-[[(1R)-1-(2-bromophenyl)ethox]methyl]oxirane (1.02 g) obtained in Example 1, Step 1, were added and the mixture was stirred at 80° C. for 3 hr. The reaction mixture was cooled to room temperature and extracted with diethyl ether. The organic layer was washed successively with water and brine, dried over sodium sulfate, and concentrated under reduced pressure. The obtained residue was purified by silica gel column chromatography (hexane:ethyl acetate=3:1) to give the title compound (426 mg).

Step 3

Diethyl [2'-[(1R)-1-[(2R)-2-hydroxy-3-[[2-methyl-1-(naphthalen-2-yl)propan-2-yl]amino]propoxy]ethyl]biphenyl-4-yl]phosphonate

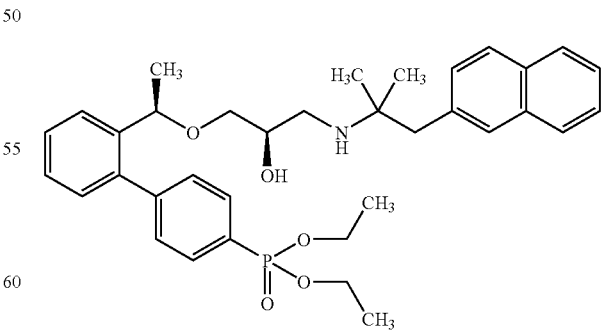

The title compound (580 mg) was obtained in the same manner as in Example 1, Step 4, from diethyl [2-[(1R)-1-(((2R)-oxiranyl)methoxy)ethyl]phenyl]phosphonate (420 mg) obtained in Step 2.

Step 4

Monoethyl [2'-[(1R)-1-[(2R)-2-hydroxy-3-[[2-methyl-1-(naphthalen-2-yl)propan-2-yl]amino]propoxy]ethyl]biphenyl-4-yl]phosphonate

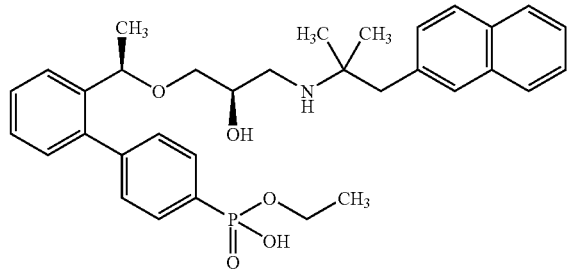

Diethyl [2'-[(1R)-1-[(2R)-2-hydroxy-3-[[2-methyl-1-(naphthalen-2-yl)propan-2-yl]amino]propoxy]ethyl]biphenyl-4-yl]phosphonate (574 mg) obtained in Step 3 was dissolved in dichloromethane (10 ml), and bis(trimethylsilyl)trifluoroacetamide (284 µl) and trimethylsilyl bromide (300 µl) were added. The mixture was stirred at 0° C. for 1 hr. The reaction mixture was washed with water and brine, and dried over magnesium sulfate. The organic layer was concentrated under reduced pressure and the obtained residue was dissolved in 1N-sodium hydroxide and acidified with 10% aqueous citric acid. The precipitated solid was collected by filtration to give the title compound (184 mg).

$^1$H-NMR (400 MHz, δppm, CD$_3$OD) 7.90-7.75 (6H, m), 7.55-7.15 (9H, m), 4.52 (1H, q, J=6.4 Hz), 3.90-3.80 (3H, m), 3.35-3.10 (5H, m), 3.00-2.90 (1H, m), 1.33 (6H, s), 1.30 (3H, d, J=6.4 Hz), 1.21 (3H, t J=9.2 Hz).

MS(ESI, m/z) 562(M+H)$^+$.

Example 12

Disodium [2'-[(1R)-1-[(2R)-2-hydroxy-3-[[2-methyl-1-(naphthalen-2-yl)propan-2-yl]amino]propoxy]ethyl]biphenyl-4-yl]phosphonate

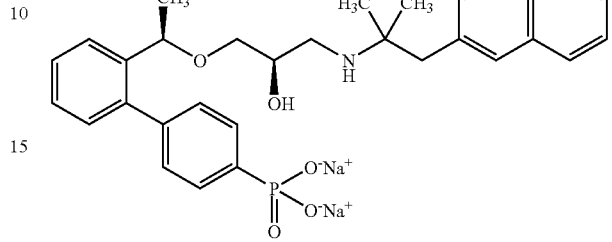

Diethyl [2'-[(1R)-1-[(2R)-2-hydroxy-3-[[2-methyl-1-(naphthalen-2-yl)propan-2-yl]amino]propoxy]ethyl]biphenyl-4-yl]phosphonate (627 mg) obtained in Example 11, Step 3 was dissolved in dichloromethane (10 ml), bis(trimethylsilyl)trifluoroacetamide (311 µl) and trimethylsilyl bromide (560 µl) were added and the mixture was stirred at 0° C. for 2 hr. The reaction mixture was extracted twice with 1N-aqueous sodium hydroxide, and the aqueous sodium hydroxide layer was acidified with 10% aqueous citric acid. The precipitated phosphonic acid (460 mg) was collected by filtration. The obtained phosphonic acid (200 mg) was dissolved in 2 equivalents of 1N-aqueous sodium hydroxide solution and the solution was freez-dried to give the title compound (217 mg).

$^1$H-NMR (400 MHz, δppm, CD$_3$OD) 7.95-7.90 (2H, m), 7.80-7.70 (3H, m), 7.65 (1H, s), 7.50-7.05 (9H, m), 4.52 (1H, q, J=6.0 Hz), 3.75-3.65 (1H, m), 3.14-3.12 (2H, m), 2.90-2.50 (4H, m), 1.27 (3H, d, J=6.0 Hz), 1.10 (3H, s), 1.07 (3H, s).

MS(ESI, m/z) 534(M+3H−2Na)$^+$.

Example 13-33

Examples 13-33 were obtained based on the method of any of Examples 1-12. The obtained results are shown in Tables 1-5.

TABLE 1

| Ex. | structural formula | property data |
|---|---|---|
| 13 | ![structure] | $^1$H-NMR(300MHz, δppm, DMSO-d$_6$) 7.92-7.86(3H, m), 7.74(1H, s), 7.59-7.43(4H, m), 7.38-7.33(4H, m), 7.26(2H, d, J=8.1Hz), 7.21-7.17(1H, m), 4.53-4.46(1H, m), 4.12(2H, q, J=7.0Hz), 3.85-3.75(1H, m), 3.74(2H, s), 3.21-3.01(4H, m), 2.96-2.75(2H, m), 1.31(1.5H, d, J=6.3Hz), 1.30(1.5H, d, J=6.3Hz), 1.24-1.19(9H, m). MS(ESI,m/z) 540(M+H)$^+$. |

TABLE 1-continued

| Ex. | structural formula | property data |
|---|---|---|
| 14 | 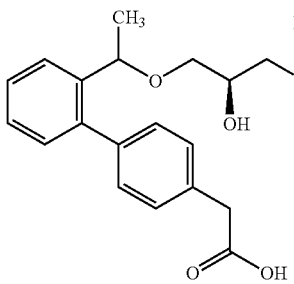 | $^1$H-NMR(300MHz, δppm, DMSO-$d_6$) 7.88-7.79(3H, m), 7.68(1H, s), 7.55-7.29(8H, m), 7.22(2H, d, J=7.9Hz), 7.15(1H, d, J=7.5Hz), 4.48(1H, q, J=6.3Hz), 3.68-3.58(1H, m), 3.59(2H, s), 3.16-3.06(2H, m), 2.87(2H, s), 2.81-2.77(1H, m), 2.68-2.54(1H, m), 1.26(3H, d, J=6.3Hz), 1.05(3H, s), 1.04(3H, s). MS(ESI, m/z) 512(M+H)$^+$. |
| 15 | 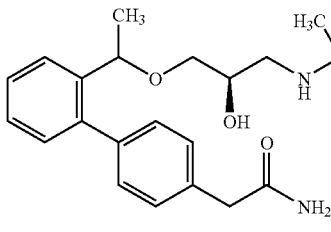 | $^1$H-NMR(300MHz, δppm, DMSO-$d_6$) 7.87-7.75(3H, m), 7.66(1H, s), 7.56-7.29(9H, m), 7.23-7.13(3H, m), 6.93-6.88(1H, m), 4.47(1H, q, J=6.2Hz), 3.58-3.50(1H, m), 3.43(2H, s), 3.12-3.07(2H, m), 2.76(2H, s), 2.68-2.61(1H, m), 2.56-2.45(1H, m), 1.25(1.5H, d, J=6.2Hz), 1.24(1.5H, d, J=6.2Hz), 0.98(1.5H, s), 0.97(1.5H, s), 0.95(3H, s). MS(ESI, m/z) 511(M+H)$^+$. |
| 16 | 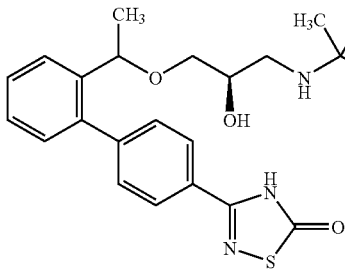 | $^1$H-NMR(300MHz, δppm, DMSO-$d_6$) 8.06(2H, d, J=8.5Hz), 7.91-7.85(3H, m), 7.73(1H, s), 7.60-7.43(4H, m), 7.40-7.31(4H, m), 7.25-7.22(1H, m), 4.53(1H, q, J=6.3Hz), 3.85-3.75(1H, m), 3.23-2.99(5H, m), 2.90-2.75(1H, m), 1.32(1.5H, d, J=6.3Hz), 1.31(1.5H, d, J=6.3Hz), 1.19(6H, s). MS(ESI, m/z) 554(M+H)$^+$. |
| 17 | 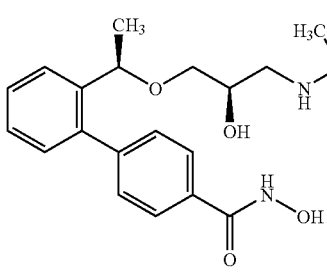 | $^1$H-NMR(300MHz, δppm, DMSO-$d_6$) 7.87-7.76(5H, m), 7.66(1H, s), 7.56-7.53(1H, m), 7.50-7.41(3H, m), 7.39-7.33(4H, m), 7.18(1H, dd, J=7.7, 1.3Hz), 4.43(1H, q, J=6.2Hz), 3.65-3.54(1H, m), 3.16-3.06(2H, m), 2.80(2H, s), 2.74-2.49(2H, m), 1.25(3H, d, J=6.2Hz), 1.01(3H, s), 0.98(3H, s) MS(ESI, m/z) 513(M+H)$^+$. |
| 18 | 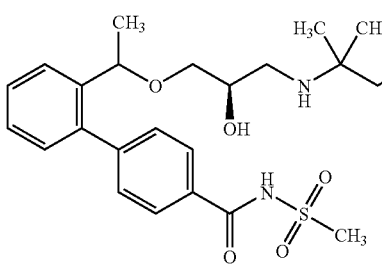 | $^1$H-NMR(300MHz, δppm, DMSO-$d_6$) 8.03(2H, d, J=8.0Hz), 7.92-7.87(3H, m), 7.75(1H, s), 7.58-7.43(4H, m), 7.38-7.34(2H, m), 7.27-7.21(3H, m), 5.60-5.43(1H, m), 4.50(1H, q, J=6.1Hz), 3.86-3.77(1H, m), 3.30-3.08(4H, m), 2.95-2.80(5H, m), 1.33-1.29(3H, m), 1.22(6H, s) MS(ESI, m/z) 575(M+H)$^+$. |

TABLE 1-continued

| Ex. | structural formula | property data |
|---|---|---|
| 19 | 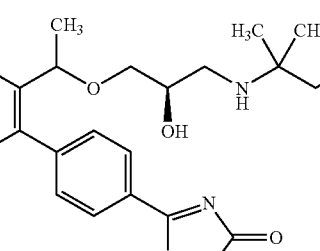 | $^1$H-NMR(400MHz, δppm, DMSO-d$_6$) 7.91-7.85(5H, m), 7.74(1H, s), 7.59-7.55(1H, m), 7.53-7.44(3H, m), 7.38-7.34(4H, m), 7.25-7.21(1H, m), 4.52(1H, q, J=6.3Hz), 3.85-3.77(1H, m), 3.22-3.12(2H, m), 3.10-3.02(3H, m) 2.89(0.5H, dd, J=12.0, 8.8Hz), 2.81(0.5H, dd, J=12.0, 9.6Hz), 1.32(1.5H, d, J=6.3Hz) 1.31(1.5H, d, J=6.3Hz), 1.20(6H, s) MS(ESI, m/z) 538(M+H)$^+$. |
| 20 | 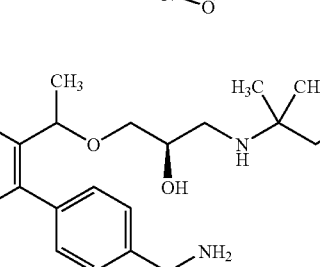 | $^1$H-NMR(400MHz, δppm, DMSO-d$_6$) 8.05(1H, s), 7.96(2H, d, J=7.4Hz), 7.87-7.76(3H, m), 7.66(1H, s), 7.58-7.53(1H, m), 7.49-1.1Hz), 4.44(1H, q, J=6.2Hz), 3.61-3.53(1H, m), 3.15-3.07(2H, m), 2.78(2H, s), 2.71-2.65(1H, m), 2.60-2.49(1H, m), 1.26(3H, d, J=6.2Hz), 1.00(1.5H, s), 0.99(1.5H, s) 0.98(3H, s) MS(ESI, m/z) 497(M+H)$^+$. |

TABLE 3

| | | |
|---|---|---|
| 21 | 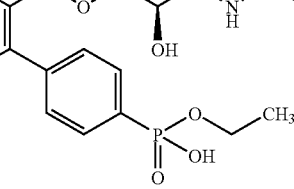 | $^1$H-NMR (300 MHz, δ ppm, CD$_3$OD) 7.84-7.20(15H, m), 4.48(1H, m), 3.88-3.81(3H, m), 3.23-3.16(3H, m), 3.04(2H, s), 3.03-2.89(1H, m), 1.31-1.18(12H, m). MS (ESI, m/z) 562 (M+H) |
| 22 | 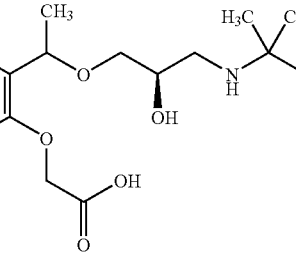 | $^1$H-NMR (400 MHz, δ ppm, DMSO-d$_6$) 7.88-7.81(3H, m), 7.70-7.68(1H, m), 7.50-7.44(2H, m), 7.35-7.28(2H, m), 7.18-7.13(1H, m), 6.92-6.85(2H, m), 5.07(0.5H, q, J=6.5 Hz), 5.01(0.5H, q, J=6.5 Hz), 4.47-4.32(2H, m), 4.10-4.04(0.5H, m), 3.91-3.85(0.5H, m), 3.43-3.32(2H, m), 3.01-2.91(3H, m), 2.82-2.78(1H, m), 1.33(1.5H, d, J=6.5 Hz), 1.32(1.5H, d, J=6.5 Hz), 1.13(3H, s), 1.10(1.5H, s), 1.09(1.5H, s). MS (ESI, m/z) 452 (M+H)$^+$. |
| 23 | 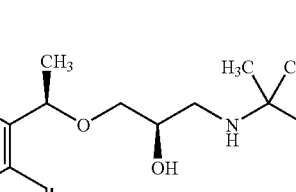 | $^1$H-NMR (300 MHz, δ ppm, DMSO-d6) 8.04(1H, d, J=14.2 Hz), 7.88-7.85(3H, m), 7.74-7.72(2H, m), 7.52-7.31(6H, m), 6.44 (1H, d, J=14.2 Hz), 4.85(1H, q, J=5.5 Hz), 4.02-4.00(1H, m), 3.42-3.09(3H, m), 3.11(2H, s), 2.85-2.83(1H, m), 1.40(3H, d, J=5.5 Hz), 1.23(6H, s). MS (ESI, m/z) 448 (M+H)$^+$. |

TABLE 3-continued

| 24 | 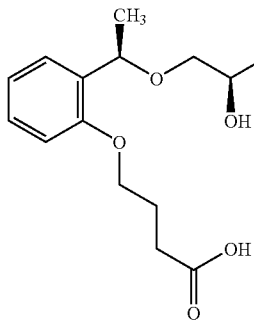 | ¹H-NMR (300 MHz, δ ppm, DMSO-d₆) 7.87-7.77(3H, m), 7.68(1H, s), 7.49-7.42(2H, m), 7.37-7.31(2H, m), 7.22-7.18(1H, m), 6.96-6.91(2H, m), 4.81(1H, q, J=6.3 Hz), 4.00(2H, t, J=6.0 Hz), 3.71(1H, brs), 3.30-3.23(2H, m), 2.82-2.72(3H, m), 2.66-2.50(1H, m), 2.38(2H, t, J=7.3 Hz), 2.00-1.92(2H, m), 1.27(3H, d, J=6.3 Hz), 1.02(3H, s), 1.01(3H, s).<br>MS (ESI, m/z) 480 (M+H)⁺. |
|---|---|---|

TABLE 4

| 25 | 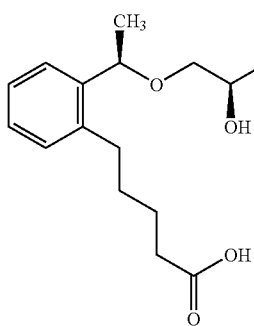 | ¹H-NMR (300 MHz, δ ppm, DMSO-d6) 7.92-7.85(3H, m), 7.75(1H, s), 7.54-7.47(2H, m), 7.39-7.36(2H, m), 7.25-7.15(3H, m), 4.75(1H, q, J=6.3 Hz), 3.96-3.94(1H, m), 3.34-3.32(1H, m), 3.19-3.17(1H, m), 3.10-3.08(1H, m), 3.09(2H, s), 2.82-2.80(1H, m), 2.63(2H, t, J=7.2 Hz), 2.26(2H, t, J=6.8 Hz), 1.61-1.54(4H, m), 1.34(3H, d, J=6.3 Hz), 1.21(6H, s).<br>MS (ESI, m/z) 478 (M+H)⁺. |
|---|---|---|
| 26 | 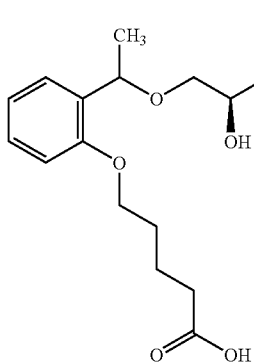 | ¹H-NMR (300 MHz, δ ppm, DMSO-d₆) 7.87-7.77(3H, m), 7.68(1H, s), 7.50-7.42(2H, m), 7.39-7.31(2H, m), 7.24-7.18(1H, m), 6.98-6.91(2H, m), 4.85-4.78(1H, m), 3.99(2H, t, J=6.1 Hz), 3.77-3.65(1H, m), 3.30-3.22(2H, m), 2.82(2H, s), 2.78-2.70(1H, m), 2.64-2.54(1H, m), 2.26(2H, t, J=7.0 Hz), 1.80-1.65(4H, m), 1.28(1.5H, d, J=6.2 Hz), 1.27(1.5H, d, J=6.6 Hz), 1.02(3H, s), 1.00(3H, s).<br>MS (ESI, m/z) 494 (M+H)⁺. |
| 27 | 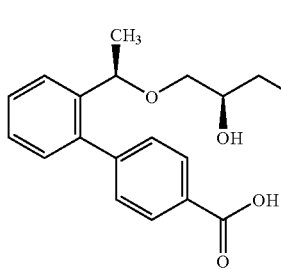 | ¹H-NMR (300 MHz, δ ppm, DMSO-d₆) 8.03 (2H, d, J=8.5 Hz), 7.58-7.55(1H, m), 7.48-7.46(1H, m), 7.39-7.28(5H, m), 7.23-7.15(3H, m), 6.70(1H, dd, J=11.0, 18.0 Hz), 5.79(1H, dd, J=1.1, 18.0 Hz), 5.23(1H, dd, J=1.1, 11.0 Hz), 4.49(1H, q, J=6.2 Hz), 3.73(1H, m), 3.15(2H, d, J=5.5 Hz), 2.88-2.83(1H, m), 2.78(2H, s), 2.65-2.59(1H, m), 1.27(3H, d, J=5.5 Hz), 1.07(3H, s), 1.06(3H, s).<br>MS (ESI, m/z) 474 (M+H)⁺. |

TABLE 5

| 28 | 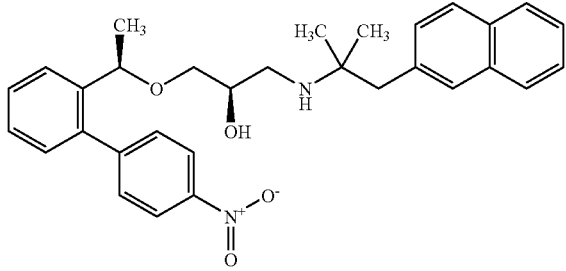 | ¹H-NMR(300MHz, δppm, DMSO-d$_6$) 8.31-8.28(2H, m), 7.86-7.82(1H, m), 7.79-7.74(2H, m) 7.64(1H, s), 7.61-7.56(3H, m), 7.50-7.37(4H, m), 7.33(1H, dd, J=8.4, 1.6Hz), 7.22(1H, dd, J=7.6, 1.1Hz), 4.62(1H, brs), 4.41(1H, q, J=6.3Hz), 3.55-3.48(1H, m), 3.15-3.07(2H, m), 2.75(1H, d, J=13Hz), 2.72(1H, d, J=13Hz), 2.60(1H, dd, J=11.0, 4.5Hz), 2.47(1H, dd, J=11.0, 7.0Hz), 1.27(3H, d, J=6.3Hz), 0.96(3H, s), 0.94(3H, s). MS(ESI, m/z) 499 (M+H)$^+$. |
| --- | --- | --- |
| 29 | 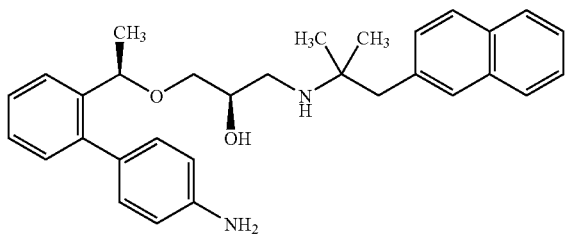 | ¹H-NMR(400MHz, δppm, DMSO-d$_6$) 7.86-7.75(3H, m), 7.65(1H, s), 7.48-7.41(3H, m), 7.35-7.23(3H, m), 7.10(1H, dd, J=7.7, 1.4Hz), 6.94-6.91(2H, m), 6.64-6.60(2H, m), 5.16(2H, s), 4.59(1H, brs), 4.55(1H, q, J=6.3Hz), 3.57-3.52(1H, m), 3.08(2H, d, J=5.8Hz), 2.75(2H, s), 2.66-2.62(1H, m), 2.48-2.44(1H, m) 1.25(3H, d, J=6.3Hz), 0.97(3H, s), 0.95(3H, s) MS(ESI, m/z) 469(M+H)$^+$. |
| 30 | 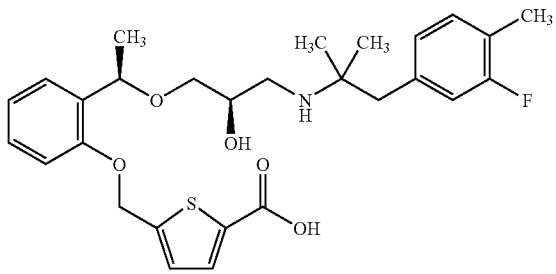 | ¹H-NMR(400MHz, δppm, DMSO-d$_6$) 7.34(1H, dd, J=7.7, 1.6Hz), 7.30(1H, d, J=3.6Hz), 7.24(1H, ddd, J=8.2, 7.7, 1.6Hz), 7.18(1H, dd, J=8.2, 8.2Hz), 7.11(1H, d, J=8.2Hz), 7.06(1H, d, J=3.6Hz), 7.00-6.96(2H, m), 6.93(1H, dd, J=1.3, 7.7Hz), 5.28(2H, s), 4.84(1H, q, J=6.4Hz), 3.91(1H, m), 3.28-3.22(2H, m), 3.01(1H, m), 2.73(1H, dd, J=12.0, 8.6Hz), 2.18(3H, s), 1.31(3H, d, J=6.4Hz), 1.12(6H, s) MS(ESI, m/z) 516(M+H)$^+$. |
| 31 | 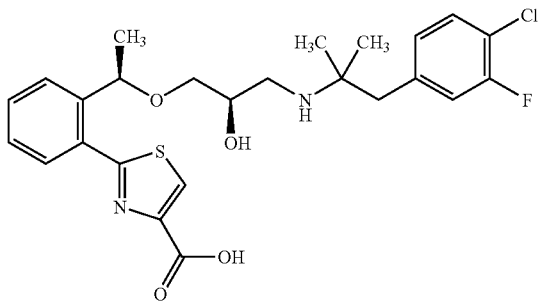 | ¹H-NMR(400MHz, δppm, DMSO-d$_6$) 8.06(1H, s), 7.61(1H, dd, J=7.6, 0.9Hz), 7.56(1H, dd, J=7.6, 0.9Hz), 7.52(1H, ddd, J=7.6, 7.6, 1.3Hz), 7.44(1H, dd, 8.1, 8.1Hz), 7.40(1H, ddd, J=7.6, 7.6, 1.3Hz), 7.25(1H, dd, J=10.7, 1.8Hz), 7.05(1H, dd, J=8.1, 1.8Hz), 5.31(1H, q, J=6.3Hz), 4.04-3.96(1H, m), 3.38(1H, dd, J=10.3, 5.3Hz), 3.25(1H, dd, J=10.3, 6.7Hz), 2.89-2.78(3H, m), 2.72-2.65(1H, m), 2.49(3H, s), 1.30(3H, d, J=6.3Hz) 1.06(3H, s), 1.05(3H, s). MS(ESI, m/z) 507(M+H)$^+$. |

TABLE 5-continued

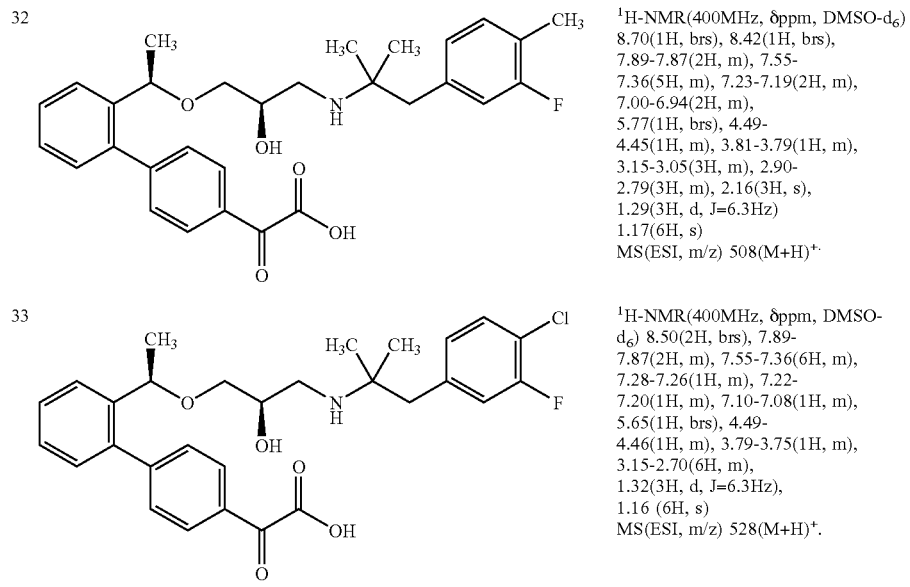

| | | |
|---|---|---|
| 32 | (structure) | $^1$H-NMR(400MHz, δppm, DMSO-d$_6$) 8.70(1H, brs), 8.42(1H, brs), 7.89-7.87(2H, m), 7.55-7.36(5H, m), 7.23-7.19(2H, m), 7.00-6.94(2H, m), 5.77(1H, brs), 4.49-4.45(1H, m), 3.81-3.79(1H, m), 3.15-3.05(3H, m), 2.90-2.79(3H, m), 2.16(3H, s), 1.29(3H, d, J=6.3Hz) 1.17(6H, s) MS(ESI, m/z) 508(M+H)$^+$ |
| 33 | (structure) | $^1$H-NMR(400MHz, δppm, DMSO-d$_6$) 8.50(2H, brs), 7.89-7.87(2H, m), 7.55-7.36(6H, m), 7.28-7.26(1H, m), 7.22-7.20(1H, m), 7.10-7.08(1H, m), 5.65(1H, brs), 4.49-4.46(1H, m), 3.79-3.75(1H, m), 3.15-2.70(6H, m), 1.32(3H, d, J=6.3Hz), 1.16(6H, s) MS(ESI, m/z) 528(M+H)$^+$. |

Experimental Examples

The bioactivity of the compound of the present invention was examined by tests.

Experimental Example 1

Evaluation of Antagonistic Action on Calcium Receptor Using Reporter Gene

Luciferase cDNA and human calcium receptor cDNA were introduced into a cell strain derived from rat adrenal to transform the cells, and the transformed cells were cultured in a medium (80 μl, F12 medium containing 0.5% dialyzed horse serum and 0.25% dialyzed bovine fetal serum). A dimethyl sulfoxide solution containing a test compound at 0.1-10000 μM was diluted 100-fold with the medium and added to the test compound group at 10 μl per well (final concentration of dimethyl sulfoxide is 0.1%). In the same manner as in test compound group, dimethyl sulfoxide diluted 100-fold with medium was added to a control group and a blank group. Then, 50 mM calcium chloride-containing medium was added to every well except the blank group at 10 μl per well (final concentration is 5 mM). A medium alone was added to the blank group. After culture for 4 hrs, luciferase substrate was added and the luciferase activity was measured with a photoluminometer. The inhibitory rate (%) was calculated from the obtained measured values according to the following formula.

$$\text{Inhibitory rate (\%)} = 100 - \frac{\text{measured value of compound group} - \text{measured value of blank group}}{\text{measured value of control group} - \text{measured value of blank group}} \times 100$$

Based on the results, the concentration (IC$_{50}$) showing 50% inhibitory rate was determined. The results are shown in Table 6.

TABLE 6

| test compound | IC$_{50}$ (μM) |
|---|---|
| 1 | 0.025 |
| 2 | 0.014 |
| 3 | 0.023 |
| 4 | 0.011 |
| 5 | 0.024 |
| 6 | 0.079 |
| 7 | 0.011 |
| 8 | 0.021 |
| 9 | 0.014 |
| 10 | 0.023 |
| 11 | 0.008 |
| 12 | 0.029 |
| 13 | 0.160 |
| 14 | 0.119 |
| 15 | 0.145 |
| 16 | 0.135 |
| 17 | 0.104 |
| 18 | 0.022 |
| 19 | 0.018 |
| 20 | 0.030 |
| 21 | 0.015 |
| 22 | 0.237 |
| 23 | 0.016 |
| 24 | 0.246 |
| 25 | 0.018 |
| 26 | 0.190 |
| 27 | 0.014 |
| 28 | 0.254 |
| 29 | 0.055 |
| 30 | 0.183 |

Experimental Example 2

PTH Secretagogue Action

The test compound was orally administered to 5 to 9-week-old male SD rats (Charles River Japan, Inc.) fasted for 20 hr, using a solvent (0.5% aqueous methyl cellulose solution) at a dose of 3 mg/5 ml/kg or 30 mg/5 ml/kg. A solvent alone was orally administered to the control group at a dose of 5 ml/kg. The blood was drawn from the tail vein 15 min, 30 min, 60 min and 120 min after the administration of the test compound, and serum was obtained. The serum PTH concentration was measured using rat PTH ELISA kit (Amersham Biosciences). The results are shown in Table 7.

TABLE 7

| test compound (dose) | serum PTH concentration (pg/ml) | | | |
|---|---|---|---|---|
| | 15 min later | 30 min later | 60 min later | 120 min later |
| | control group | | | |
| | test compound administration group | | | |
| 1 | 14.22 ± 2.79 | 14.27 ± 1.57 | — | — |
| (3 mg/kg) | 24.86 ± 3.59 | 18.58 ± 2.15 | — | — |
| 4 | 16.15 ± 3.08 | 16.84 ± 1.40 | 9.58 ± 1.37 | 12.76 ± 1.31 |
| (3 mg/kg) | 22.71 ± 2.52 | 22.83 ± 2.91 | 13.69 ± 2.09 | 11.76 ± 1.24 |
| 6 | — | 4.9 ± 0.90 | 4.74 ± 0.9 | — |
| (30 mg/kg) | — | 14.45 ± 1.45 | 13.91 ± 1.62 | — |
| 25 | 5.65 ± 1.12 | 16.64 ± 3.15 | — | — |
| (3 mg/kg) | 19.16 ± 4.05 | 18.15 ± 3.15 | — | — |

Experimental Example 3

Metabolic Enzyme CYP2D6 Inhibitory Activity

Using a metabolic enzyme CYP2D6 inhibition measurement kit (BD Bioscience) and following the manual of the kit, the inhibitory activity of the test compound was measured. With the enzyme activity free of the test compound as 100%, the concentration ($IC_{50}$) showing 50% inhibition was determined. The results are shown in Table 8, wherein ">10" means over 10 μM.

TABLE 8

| test compound | $IC_{50}$ (μM) |
|---|---|
| 1 | 9.5 |
| 12 | >10 |
| 18 | 8.0 |

When osteoporosis is to be treated by increasing the blood PTH concentration based on inhibition of the action of calcium receptor, the compound to be used for this end should have at least the following properties.

(i) The compound has a sufficient antagonistic action on calcium receptors. In other words, the compound has a sufficiently low $IC_{50}$ value. In the specification of WO99/51241, it is described, "In general, a compound showing a low $IC_{50}$ value in the assay of calcium receptor inhibitor is a more superior compound. A compound showing an $IC_{50}$ value of not lower than 50 μM is considered to be inactive. A preferable compound shows an $IC_{50}$ value of not more than 10 μM, more preferably 1 μM, and most preferably not more than 0.1 μM."

(ii) Administration of the compound results in a sufficient increase in the blood. PTH concentration.

(iii) The time-course concentrations in blood after administration of the compound are not sustainable. Desirably, the PTH concentration returns to the level before administration in 3-4 hr after administration of the compound.

From the foregoing test results, it is clear that the compounds of the present invention satisfies the above-mentioned properties.

As regards (i); as shown in Table 6, the $IC_{50}$ value of the every compound of the present invention is not more than 1 μM, and the compound has a sufficient antagonistic action on calcium receptors. The every compound of the present invention is considered to be preferable in view of the $IC_{50}$ value.

As regards (ii); as shown in Table 7, the serum PTH concentration 15 min later was 1.4-3.4 times higher (only when the test compound was Example 6, comparison was made 30 min later) than the control, and every compound of the present invention was confirmed to have a superior PTH secretion promoting action.

As regards (iii); as shown in Table 7, PTH secretion by the compound of the present invention reached a peak at 15 min or 30 min after administration, sharply decreased thereafter and returned to the blood PTH concentration before administration in about 1-2 hr. It is clear from this aspect that the compound of the present invention is superior. In contrast, as a result of the reproductive test of NPS-2143 of the reference, the sustained PTH secretion promoting action of NPS-2143 was confirmed.

INDUSTRIAL APPLICABILITY

As is clear from the above-mentioned Experimental Example 1, the compound of the formula (1) or (1') of the present invention has a superior calcium receptor antagonistic action. Accordingly, the compound is expected to be useful as a therapeutic drug for diseases accompanied by abnormal calcium homeostasis, such as osteoporosis, hypoparathyreosis, osteosarcoma, periodontal disease, bone fracture, osteoarthrisis, chronic rheumatoid arthritis, Paget's disease, humoral hypercalcemia, autosomal dominant hypocalcemia and the like. As is clear from Experimental Examples 2 and 3, the is compound of the present invention has a temporary PTH secretion promoting action, and as is clear from Experimental Example 4, it has weak metabolic enzyme CYP2D6 inhibitory activity. Accordingly, the compound is particularly useful as a therapeutic agent for osteoporosis.

This application is based on a patent application No. 151610/2003 filed in Japan, the contents of which are hereby incorporated by reference.

The invention claimed is:

1. A compound represented by the following formula (1), an optically active form thereof, or a pharmaceutically acceptable salt thereof:

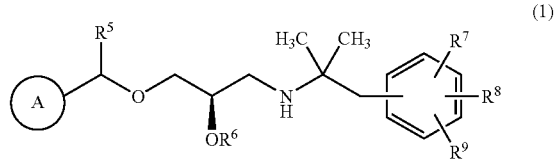

(1)

ring A is a $C_{3-6}$ cycloalkyl group,

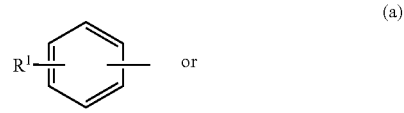

(a)

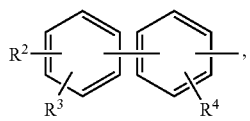
(b)

wherein R₁ is a $C_{1-6}$ alkyl group or $R^4O—C(=O)—X—(O)n-$, wherein $R^A$ is a hydrogen atom, a $C_{1-6}$ alkyl group or $R^BO—C(=O)O—C_{1-6}$ alkylene- (wherein $R^B$ is a $C_{1-6}$ alkyl group or a $C_{3-6}$ cycloalkyl group), X is a $C_{1-6}$ alkylene group, a $C_{2-4}$ alkenylene group, a $C_{2-4}$ alkynylene group,

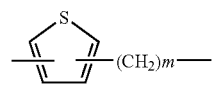

(wherein m is an integer of 0 to 6) or

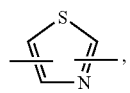

and n is 0 or 1,

R² is a carboxy-$C_{1-6}$ alkyl group, a $C_{1-6}$ alkoxy-carbonyl-$C_{1-6}$ alkyl group, a carbamoyl-$C_{1-6}$ alkyl group, a $C_{1-7}$ acylamino-$C_{1-6}$ alkyl group, a hydroxycarbamoyl group, a $C_{1-6}$ alkylsulfonyl-carbamoyl group, an oxalo group, a phosphoric acid group optionally esterified by a $C_{1-6}$ alkyl group, $R^AO—C(=O)—$ ($R^A$ is as defined above) or a 5- or 6-membered heterocyclic residue having 1 to 4 hetero atoms selected from the group consisting of a nitrogen atom, an oxygen atom and a sulfur atom (said heterocyclic residue is optionally substituted by an oxo group), R³ and R⁴ are the same or different and each is a hydrogen atom, a cyano group, a halogen atom, a $C_{1-6}$ alkyl group, a $C_{1-6}$ alkoxy group, a halo $C_{1-6}$ alkyl group or a halo $C_{1-6}$ alkoxy group, R⁵ is a $C_{1-6}$ alkyl group or a $C_{3-6}$ cycloalkyl group, R⁶ is a hydrogen atom or $R^C$ (wherein $R^C$ is a $C_{1-7}$ acyl group optionally substituted by a carboxyl group), R⁷, R⁸ and R⁹ are the same or different and each is a hydrogen atom, a $C_{1-6}$ alkyl group, a $C_{2-4}$ alkenyl group, a halogen atom, a halo $C_{1-6}$ alkyl group, a $C_{1-6}$ alkoxy group, a halo $C_{1-6}$ alkoxy group, or a carboxyl group, or the adjacent R⁷ and R⁸ are joined to form —CH=CH—CH=CH—, provided that (1) when ring A is a group of the formula (a) and R¹ is a $C_{1-6}$ alkyl group, then R⁶ is $R^C$, (2) when ring A is a group of the formula (b) and R² is a carboxyl group or a $C_{1-6}$ alkoxy-carbonyl group, then R⁷ is a $C_{2-4}$ alkenyl group, (3) when ring A is a group of the formula (b) and R² is a hydroxycarbamoyl group, then R³ is a hydrogen atom, or (4) when ring A is a group of the formula (a), R¹ is $R^4O—C(=O)—X—(O)n-$ and X is

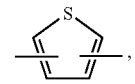

then n is 0.

2. The compound of claim 1, wherein ring A is

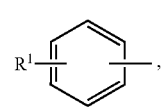
(a)

R¹ is a $C_{1-6}$ alkyl group or $R^4O—C(=O)—X—(O)n-$, wherein $R^A$ is a hydrogen atom, X is a $C_{1-6}$ alkylene group, a $C_{2-4}$ alkenylene group, a $C_{2-4}$ alkynylene group,

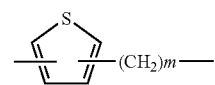

(wherein m is an integer of 0 to 6) or

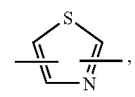

and n is 0,

R⁵ is a $C_{1-6}$ alkyl group or a $C_{3-6}$ cycloalkyl group,

R⁶ is a hydrogen atom,

R⁷, R⁸ and R⁹ are the same or different and each is a hydrogen atom, a $C_{1-6}$ alkyl group, a $C_{2-4}$ alkenyl group, a halogen atom, a halo $C_{1-6}$ alkyl group, a $C_{1-6}$ alkoxy group, a halo $C_{1-6}$ alkoxy group, or a carboxyl group, or the adjacent R⁷ and R⁸ are joined to form —CH=CH—CH=CH—, an optically active form thereof, or a pharmaceutically acceptable salt thereof.

3. The compound of claim 1, wherein ring A is

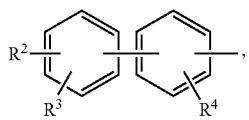
(b)

R² is a carboxy-$C_{1-6}$ alkyl group, a $C_{1-6}$ alkoxy-carbonyl-$C_{1-6}$ alkyl group, a carbamoyl-$C_{1-6}$ alkyl group, a $C_{1-7}$ acylamino-$C_{1-6}$ alkyl group, or a hydroxycarbamoyl group, R³ and R⁴ are the same or different and each is a hydrogen atom, a cyano group, a halogen atom, a $C_{1-6}$ alkyl group, a $C_{1-6}$ alkoxy group, a halo $C_{1-6}$ alkyl group or a halo $C_{1-6}$ alkoxy group, R⁵ is a $C_{1-6}$ alkyl group or a $C_{3-6}$ cycloalkyl group, R⁶ is a hydrogen atom, R⁷, R⁸ and R⁹ are the same or different and each is a hydrogen atom, a $C_{1-6}$ alkyl group, a $C_{2-4}$ alkenyl group, a halogen atom, a halo $C_{1-6}$ alkyl group, a $C_{1-6}$ alkoxy group, a halo $C_{1-6}$ alkoxy group, or a carboxyl group, or the adjacent R⁷ and R⁸ are joined to form —CH=CH—CH=CH—, an optically active form thereof, or a pharmaceutically acceptable salt thereof.

4. The compound of claim 1, which is selected from the group consisting of the following structural formulas, an optically active form thereof, or a pharmaceutically acceptable salt thereof:

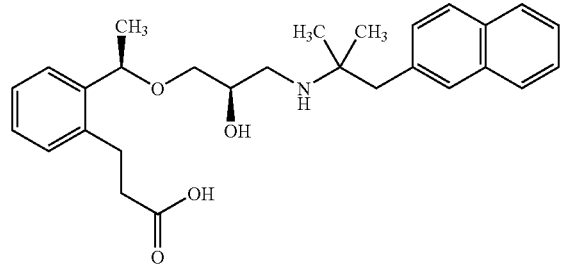

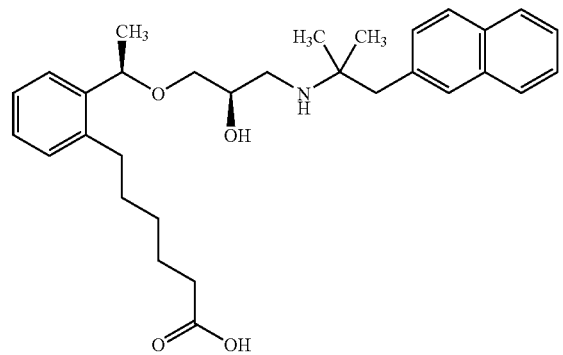

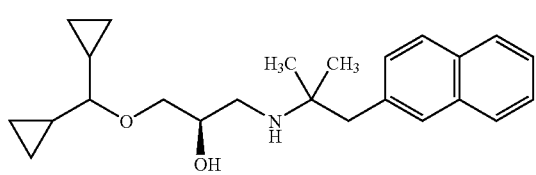

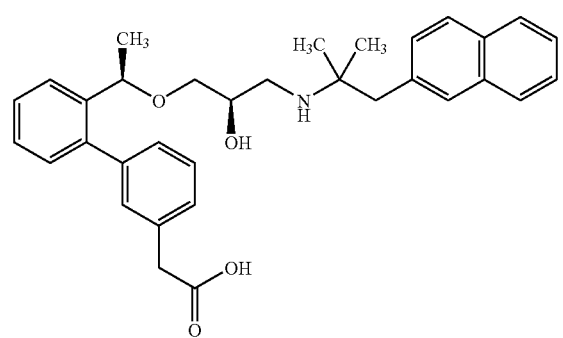

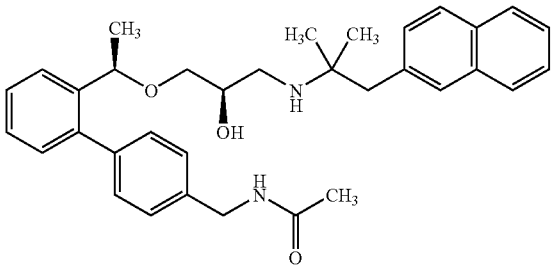

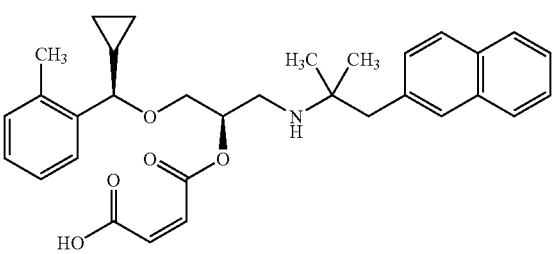

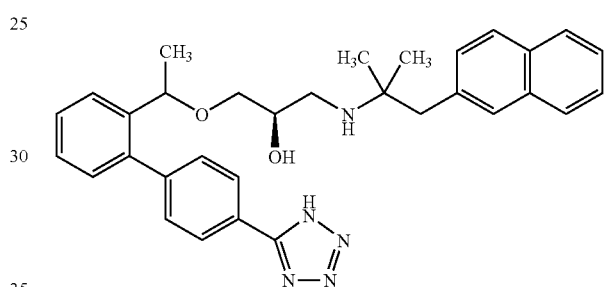

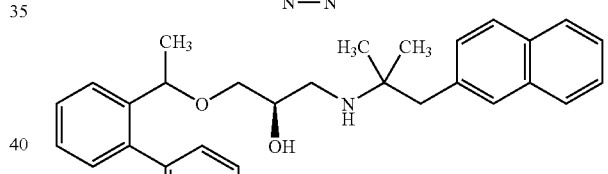

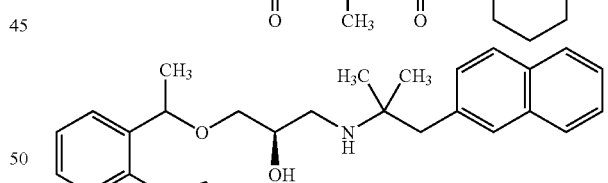

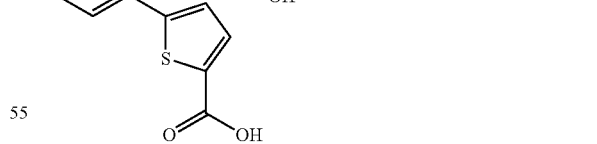

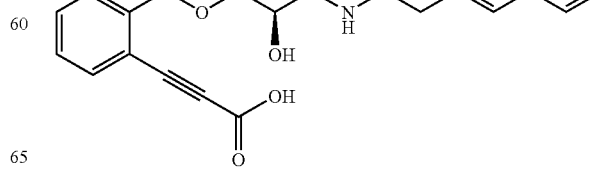

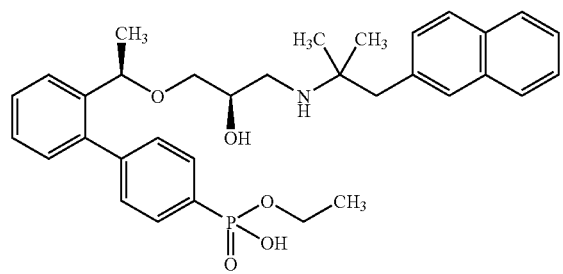
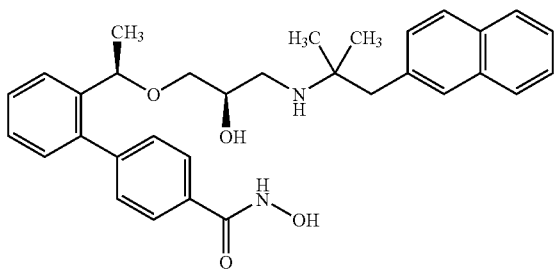
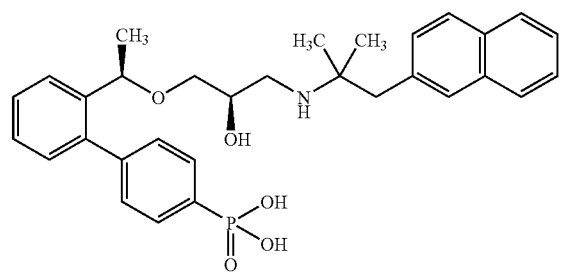
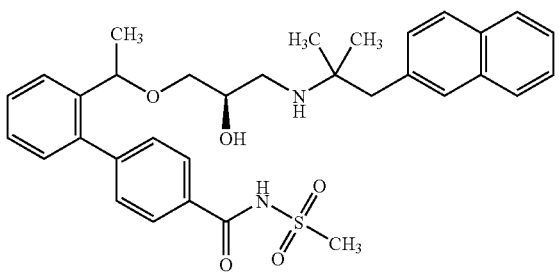
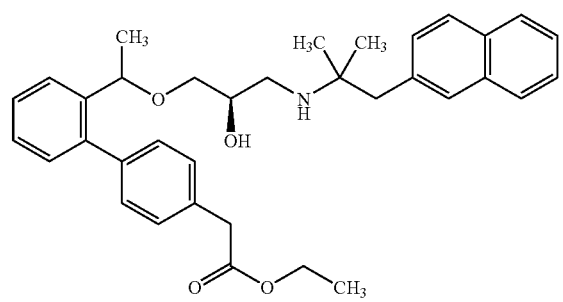
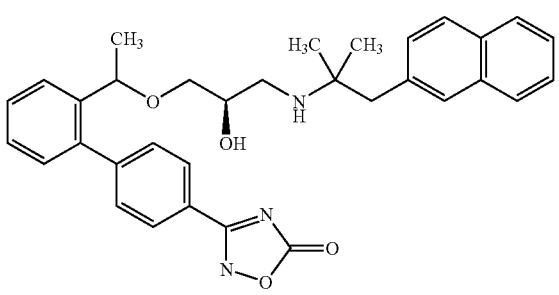
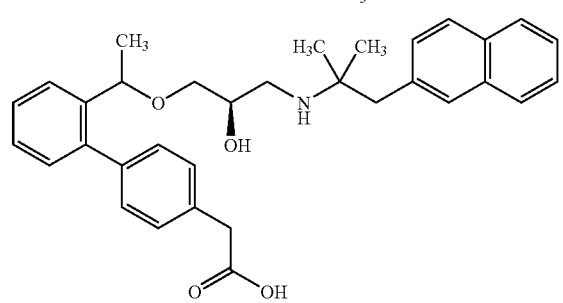
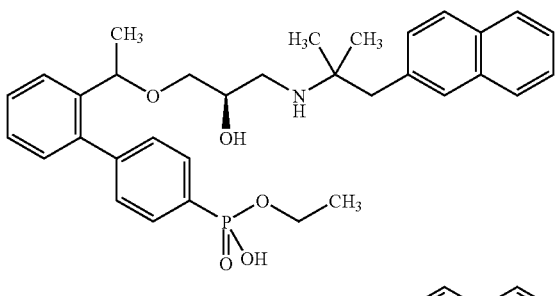
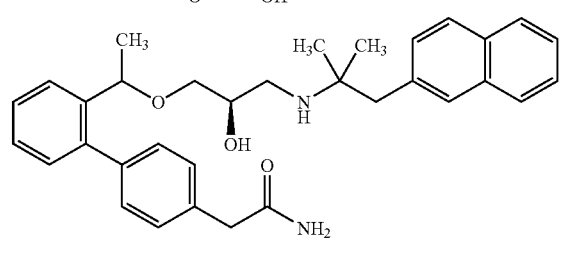
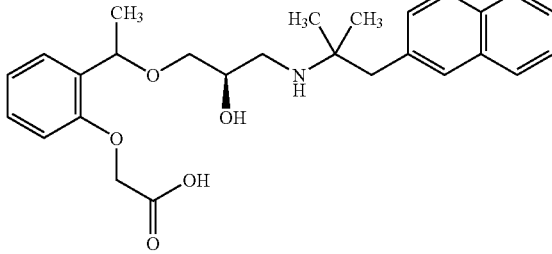
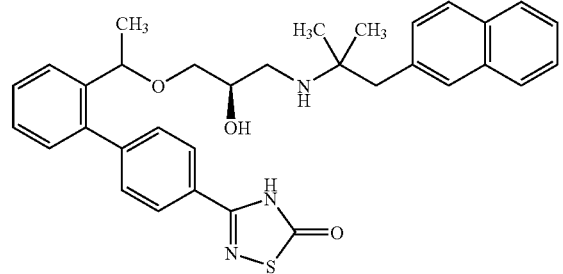
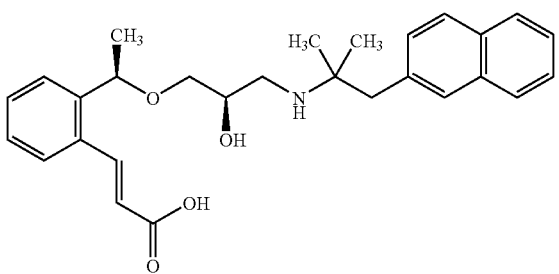

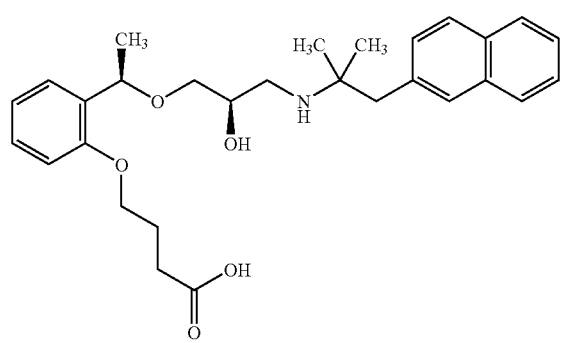
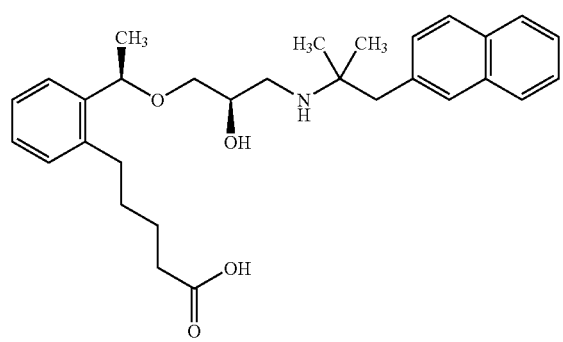
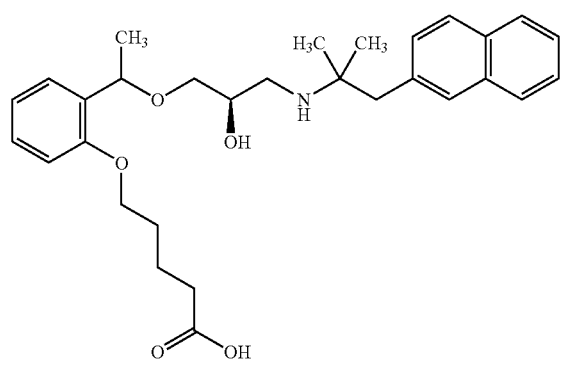
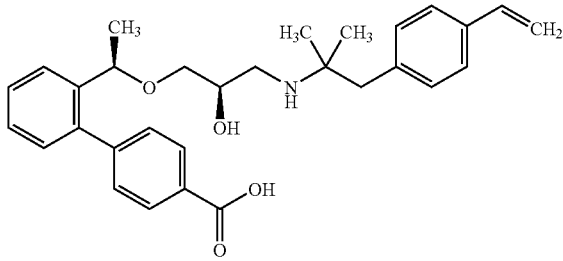
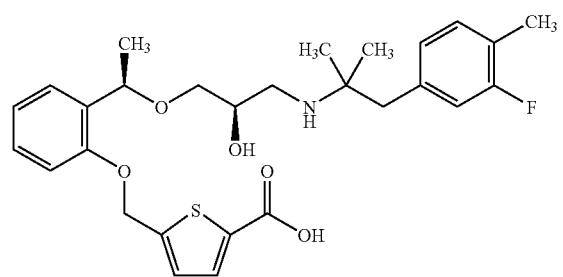
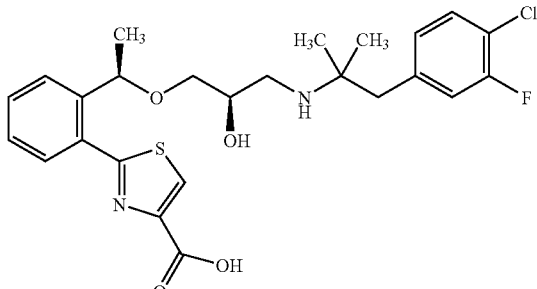
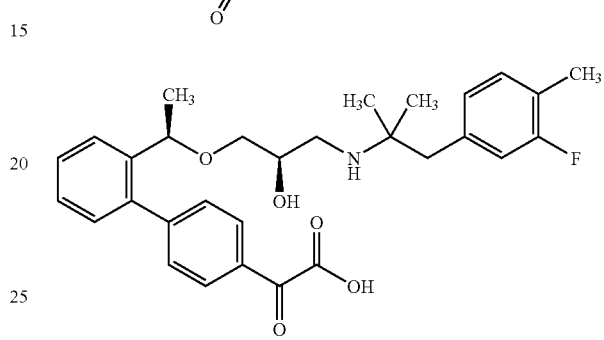
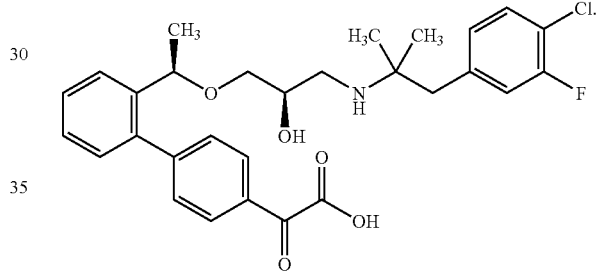
5. A compound represented by the following formula (1'), a pharmaceutically acceptable salt thereof or an optically active form thereof:
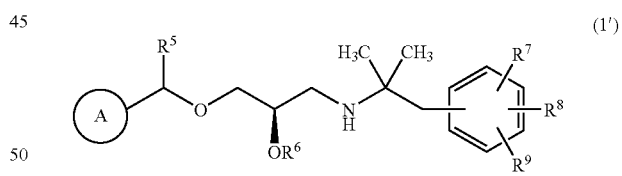
ring A is a $C_{3-6}$ cycloalkyl group,
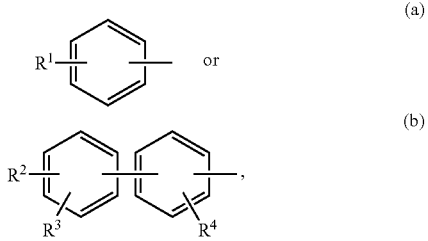

$R^1$ is a $C_{1-6}$ alkyl group or $R^4O-C(=O)-X-(O)n-$, wherein $R^4$ is a hydrogen atom, a $C_{1-6}$ alkyl group or $R^BO-C(=O)O-C_{1-6}$ alkylene- (wherein $R^B$ is a $C_{1-6}$ alkyl group or a $C_{3-6}$ cycloalkyl group), X is a $C_{1-6}$ alkylene group, a $C_{2-4}$ alkenylene group, a $C_{2-4}$ alkynylene group, or

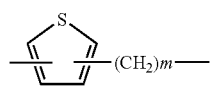

(wherein m is an integer of 0 to 6), and n is 0 or 1, $R^2$ is a carboxy-$C_{1-6}$ alkyl group, a $C_{1-6}$ alkoxy-carbonyl-$C_{1-6}$ alkyl group, a carbamoyl-$C_{1-6}$ alkyl group, a $C_{1-7}$ acylamino-$C_{1-6}$ alkyl group, a hydroxycarbamoyl group, a $C_{1-6}$ alkylsulfonyl-carbamoyl group, a phosphoric acid residue optionally esterified by a $C_{1-6}$ alkyl group, $R^4O-C(=O)-$ ($R^4$ is as defined above) or a 5- or 6-membered heterocyclic residue having 1 to 4 hetero atoms selected from the group consisting of a nitrogen atom, an oxygen atom and a sulfur atom (said heterocyclic residue is optionally substituted by an oxo group), $R^3$ and $R^4$ are the same or different and each is a hydrogen atom, a cyano group, a halogen atom, a $C_{1-6}$ alkyl group or a $C_{1-6}$ alkoxy group, $R^5$ is a $C_{1-6}$ alkyl group or a $C_{3-6}$ cycloalkyl group, $R^6$ is a hydrogen atom or $R^C$ (wherein $R^C$ is a $C_{1-7}$ acyl group optionally substituted by a carboxyl group), $R^7$, $R^8$ and $R^9$ are the same or different and each is a hydrogen atom, a $C_{1-6}$ alkyl group, a $C_{2-4}$ alkenyl group, a halogen atom, a halo $C_{1-6}$ alkyl group, a $C_{1-6}$ alkoxy group, a halo $C_{1-6}$ alkoxy group, or a carboxyl group, or the adjacent $R^7$ and $R^8$ are joined to form $-CH=CH-CH=CH-$, provided that (1) when ring A is a group of the formula (a) and $R^1$ is a $C_{1-6}$ alkyl group, then $R^6$ is $R^C$, (2) when ring A is a group of the formula (b) and $R^2$ is a carboxyl group or a $C_{1-6}$ alkoxy-carbonyl group, then $R^7$ is a $C_{2-4}$ alkenyl group, (3) when ring A is a group of the formula (b) and $R^2$ is a hydroxycarbamoyl group, then $R^3$ is a hydrogen atom, or (4) when ring A is a group of the formula (a), $R^1$ is $R^4O-C(=O)-X-(O)n-$ and X is

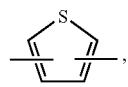

then n is 0.

6. A pharmaceutical composition comprising a pharmaceutically acceptable carrier and a compound according to claim 1, an optically active form thereof, or a pharmaceutically acceptable salt thereof as an active ingredient.

7. A method for treatment of osteoporosis, which comprises administering an effective amount of a compound according to claim 1, an optically active form thereof, or a pharmaceutically acceptable salt thereof to a patient in need thereof.

8. The method of claim 7, wherein said compound according to claim 1, optically active form thereof or pharmaceutically acceptable salt thereof is administered in combination with other therapeutic drug for osteoporosis.

9. The method of claim 8, wherein said other therapeutic drug for osteoporosis is selected from the group consisting of a calcium agent, a vitamin D preparation, a vitamin K preparation, a female hormone preparation, an estrogen antagonist preparation, a anabolic steroid preparation, a parathyroid hormone preparation, a calcitonin preparation, a bisphosphonate preparation and an ipriflavone preparation.

10. A compound according to claim 1, an optically active form thereof, or a pharmaceutically acceptable salt thereof having calcium receptor antagonist activity evidenced by an $IC_{50}$ concentration of less than 1 μM.

* * * * *